(12) United States Patent
Seul et al.

(10) Patent No.: US 7,977,050 B2
(45) Date of Patent: Jul. 12, 2011

(54) NUCLEIC ACID AMPLIFICATION WITH INTEGRATED MULTIPLEX DETECTION

(75) Inventors: Michael Seul, Fanwood, NJ (US); Nataliya Korzheva, Somerville, NJ (US); Jiacheng Yang, Hillsborough, NJ (US); Yi Zhang, Hillsborough, NJ (US)

(73) Assignee: Bioarray Solutions, Ltd., Warren, NJ (US)

( * ) Notice: Subject to any disclaimer, the term of this patent is extended or adjusted under 35 U.S.C. 154(b) by 33 days.

(21) Appl. No.: 11/218,838

(22) Filed: Sep. 2, 2005

(65) Prior Publication Data
US 2006/0188896 A1    Aug. 24, 2006

Related U.S. Application Data

(60) Provisional application No. 60/606,666, filed on Sep. 2, 2004, provisional application No. 60/628,464, filed on Nov. 16, 2004.

(51) Int. Cl.
*C12Q 1/68* (2006.01)

(52) U.S. Cl. ............................................. 435/6

(58) Field of Classification Search ................. None
See application file for complete search history.

(56) References Cited

U.S. PATENT DOCUMENTS

| | | | | |
|---|---|---|---|---|
| 5,512,439 A | * | 4/1996 | Hornes et al. | 435/6 |
| 5,545,522 A | * | 8/1996 | Van Gelder et al. | 506/26 |
| 5,587,128 A | * | 12/1996 | Wilding et al. | 422/50 |
| 6,077,669 A | * | 6/2000 | Little et al. | 435/6 |
| 6,132,997 A | * | 10/2000 | Shannon | 435/91.21 |
| 6,277,579 B1 | | 8/2001 | Lazar et al. | |
| 2003/0082531 A1 | | 5/2003 | Soderlund et al. | |

FOREIGN PATENT DOCUMENTS

WO    WO 9740385 A1 * 10/1997
WO    WO 9740875 A2 * 11/1997

OTHER PUBLICATIONS

Kwoh, "Transcription-based amplification system & detection of human immunodeficiency virus type1 with a hybridization format" Proc. Natl. Acad. Sci.USA,1989,vol. 86:1173-1177.

Nygren, "Molecular Diagnostics of Infectious Diseases" Royal Institute of Technology Department of Biotechnology, Stockholm 2000, pp. 1-68.

T. Pastinen, et al., "A system for specific, high-throughput genotyping by allele-specific primer extension on microarrays" Genome res. 10:1031-42 (2000).

* cited by examiner

*Primary Examiner* — Christopher M. Babic
(74) *Attorney, Agent, or Firm* — Womble Carlyle Sandridge & Rice, PLLC

(57) ABSTRACT

A method mediated with in-vitro transcription ("IVT") which permits miniaturization of multiplexed DNA and RNA analysis, and in which elongation-mediated multiplexed analysis of polymorphisms (eMAP®) is used as the analysis step, is described. Also described is a method mediated with IVT is for selecting a designated strand from T7-tagged double stranded DNA: wherein, the selected strand forms the template for RNA synthesis. In one embodiment, double stranded DNA incorporating the T7 (or other) promoter sequence at the 3' end or the 5' end is produced, for example, by amplification of genomic DNA using the Polymerase Chain Reaction (PCR). Also disclosed are nested PCR designs permitting allele analysis in combination with strand selection by IVT. Further, in one embodiment of a homogeneous format for transcription-mediated amplification and multiplexed detection (which may be particularly suited for viral or pathogen detection), encoded microparticles display "looped" capture probe configurations permitting the generation of a signal upon capture of RNA product and real-time assay monitoring.

17 Claims, 43 Drawing Sheets

Fig. 6: On-chip IVT-RT-eMAP design

Figure 7: One-step on-chip RT-eMAP assay

Figure 8: Two-step on-chip IVT-RT-eMAP assay

Figure 9: One-step on-chip IVT-RT-eMAP assay

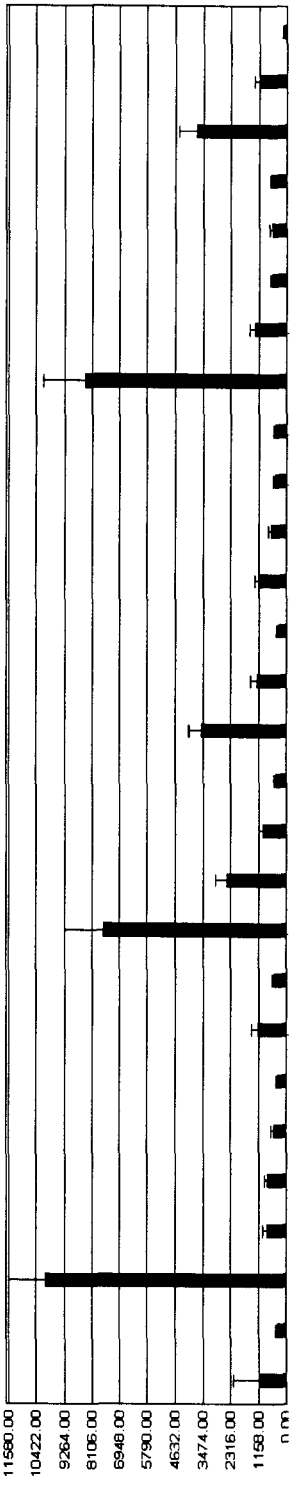
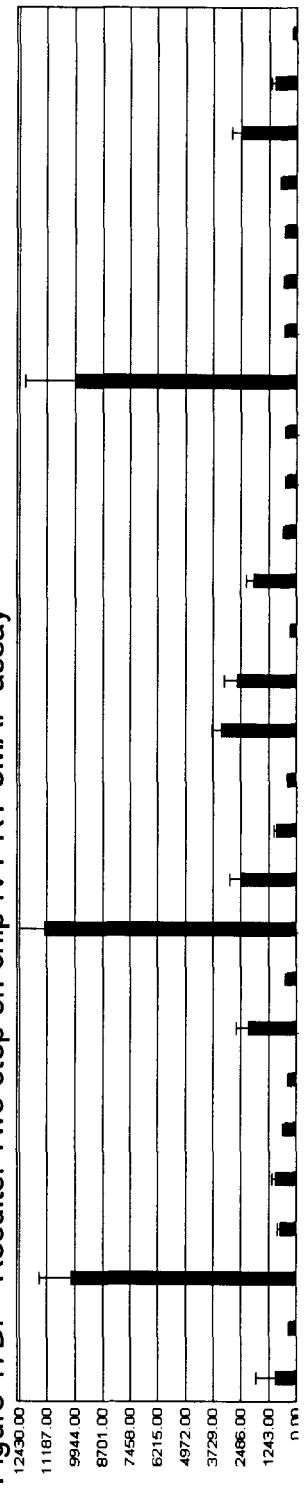
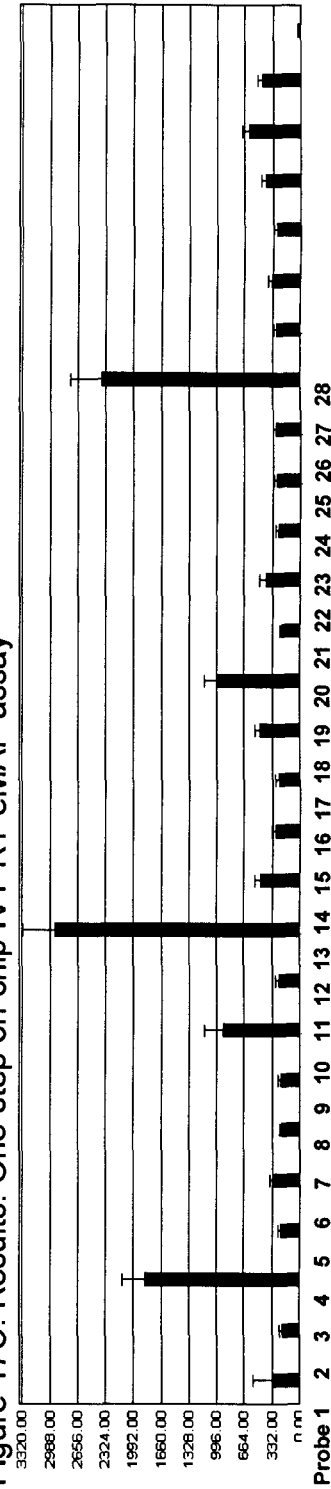
Figure 17A: Results: On-chip multiplex RT-eMAP assay
Figure 17B: Results: Two-step on-chip IVT-RT-eMAP assay
Figure 17C: Results: One-step on-chip IVT-RT-eMAP assay

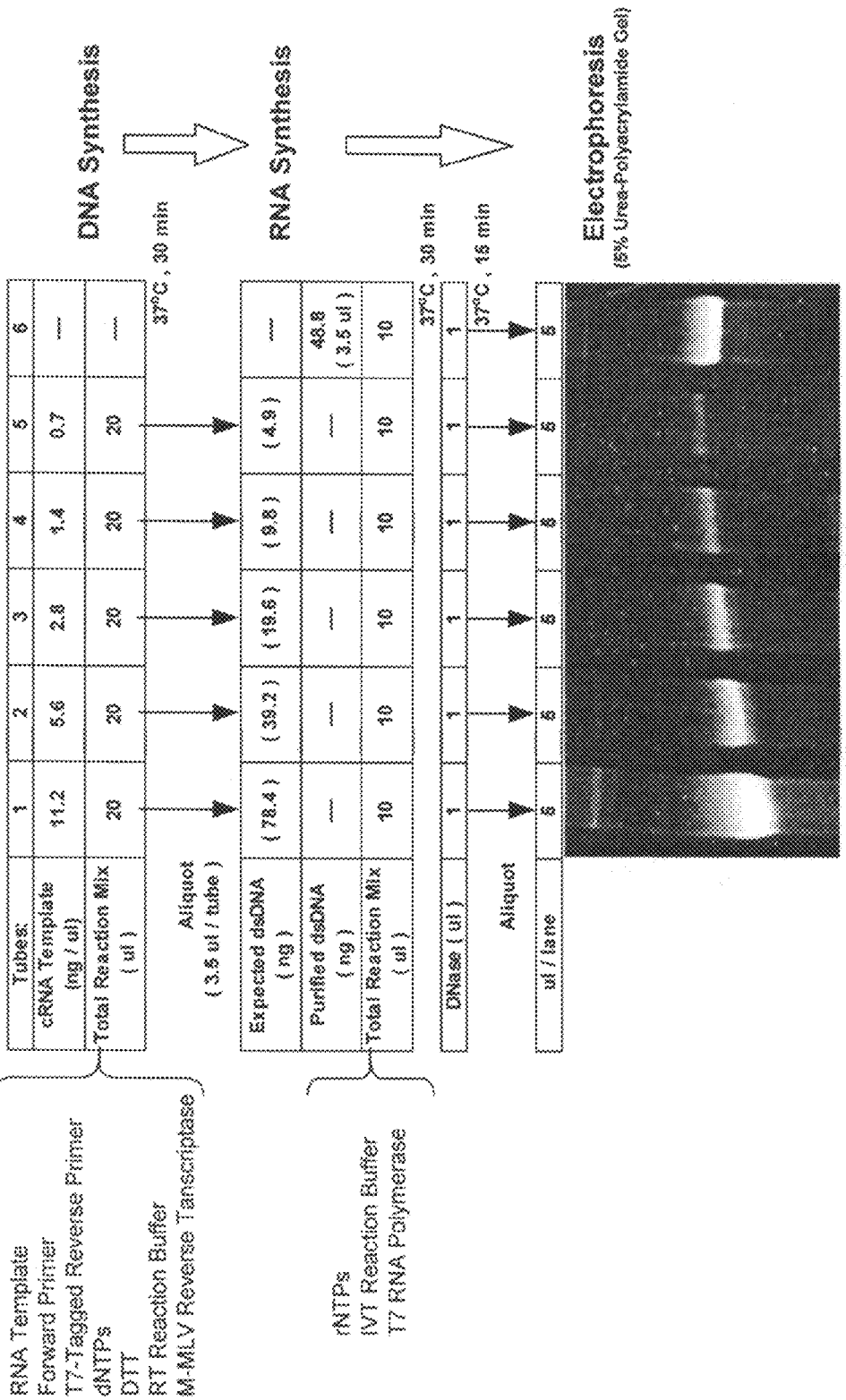
Fig. 18: In-tube Reaction: IVT w RNA Template

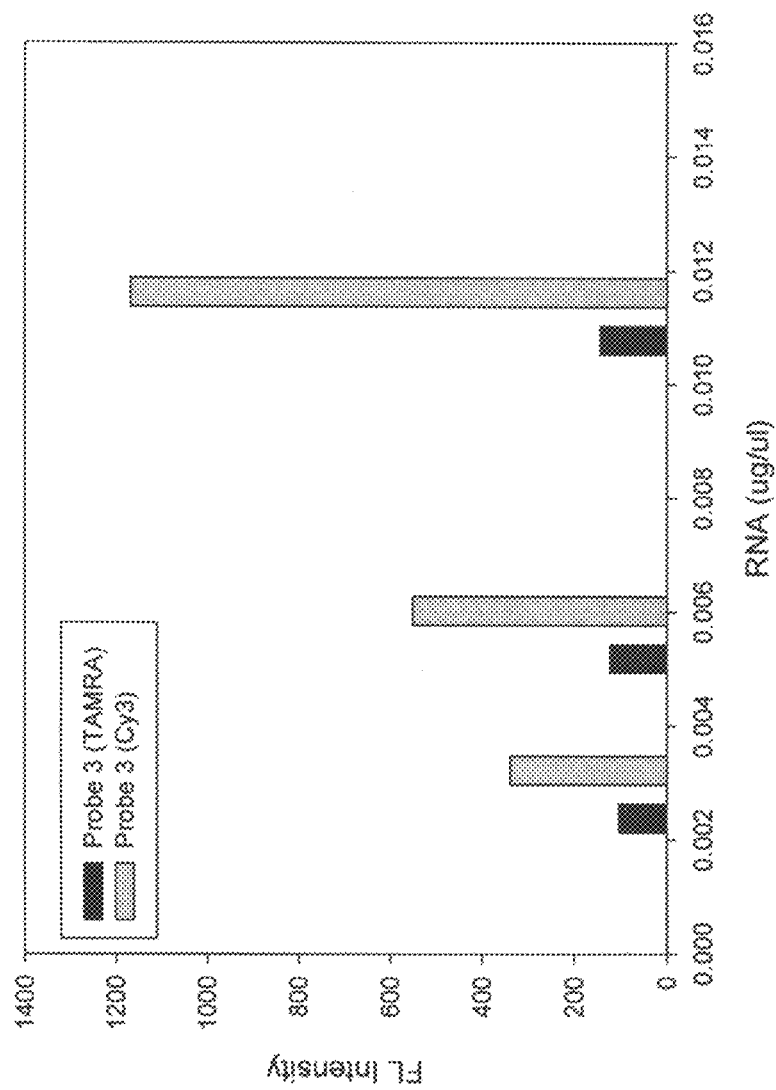

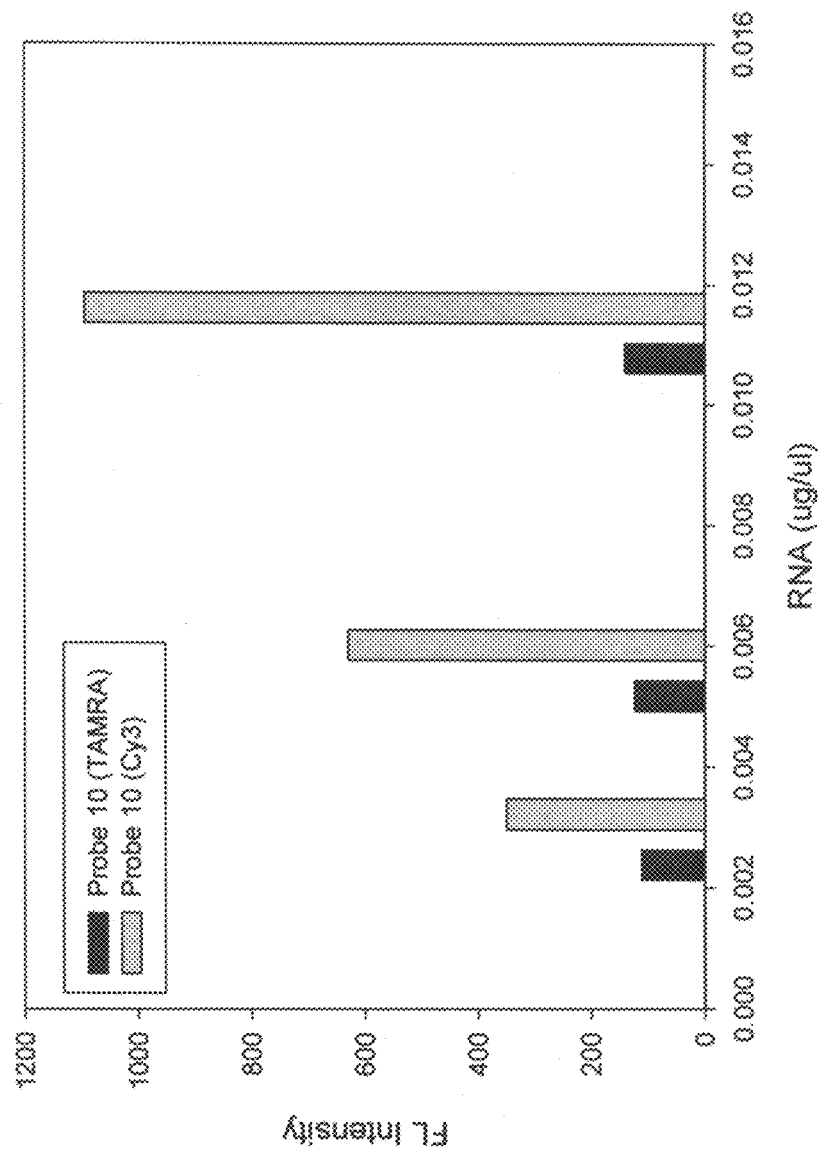

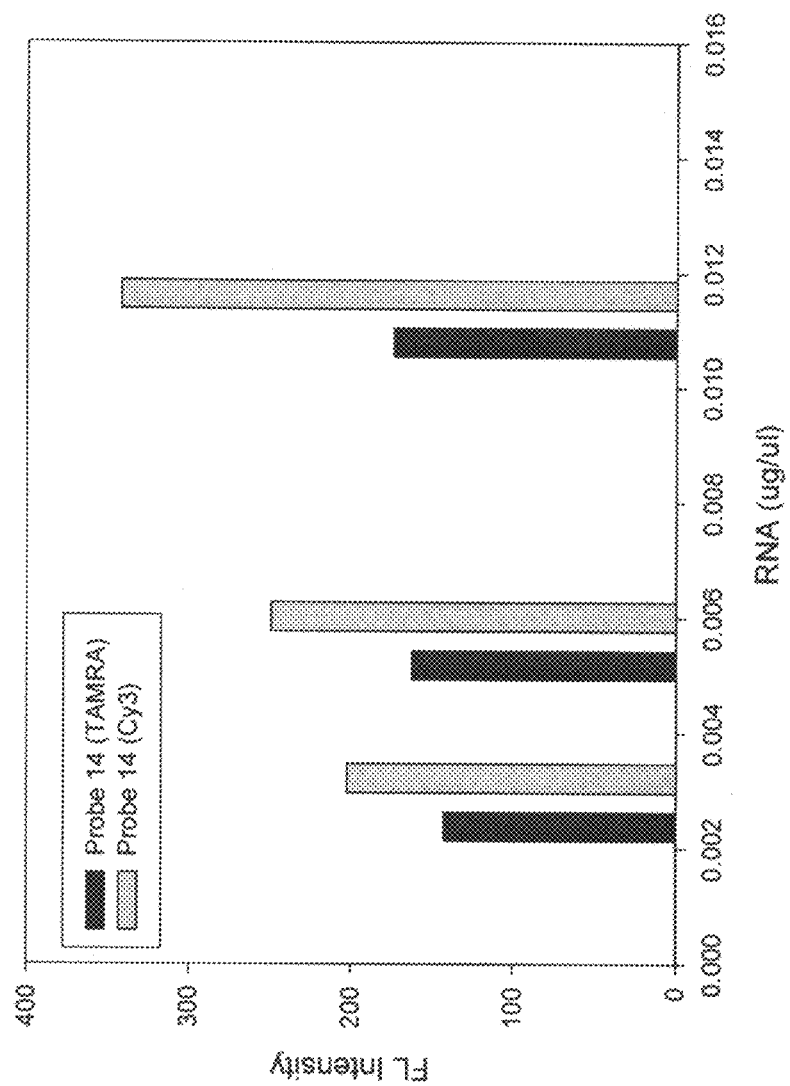

On-Chip IVT-RT-eMAP Assay (081104)
(SuperScript III Reverse Transcriptase Buffer Titration)
(One Reaction Mix, Two Temperature 37°C & 50°C)

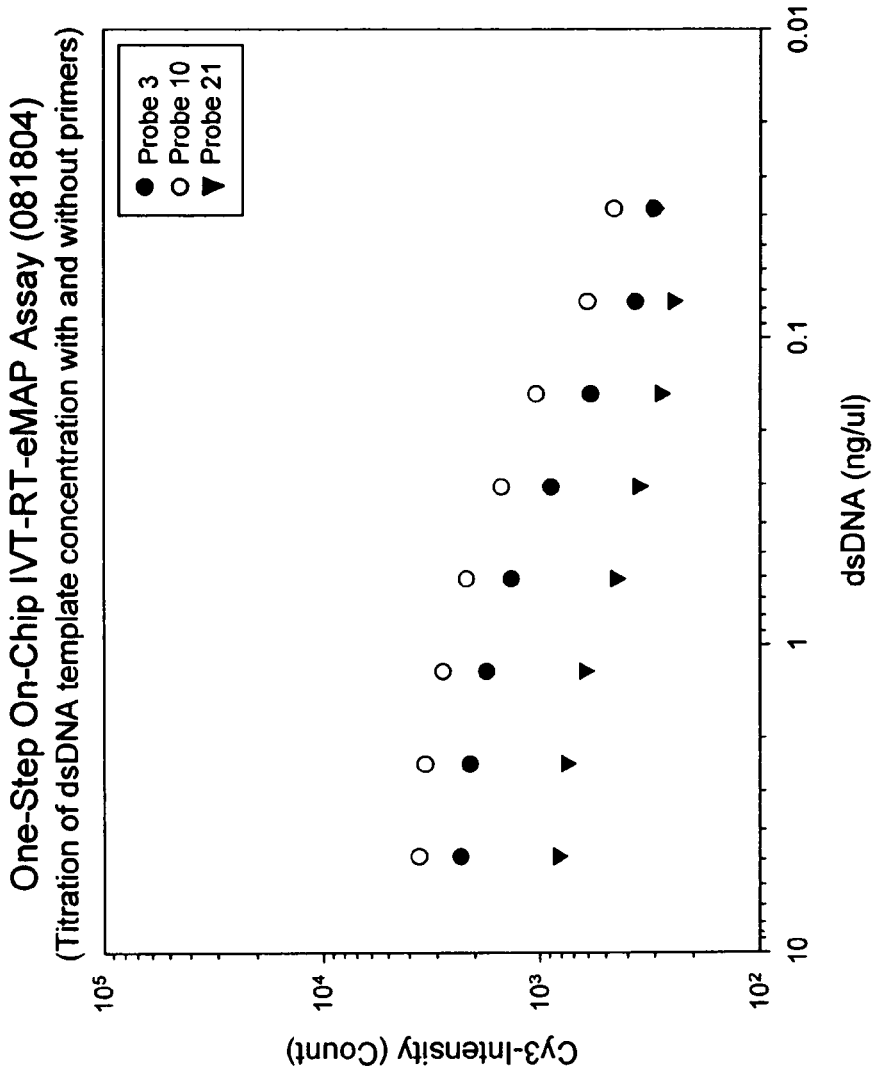

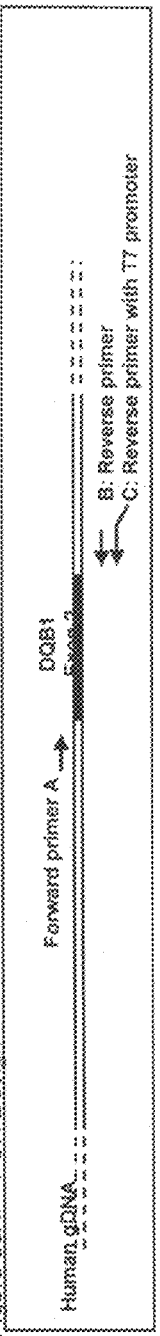
Figure 30A: PCR Design
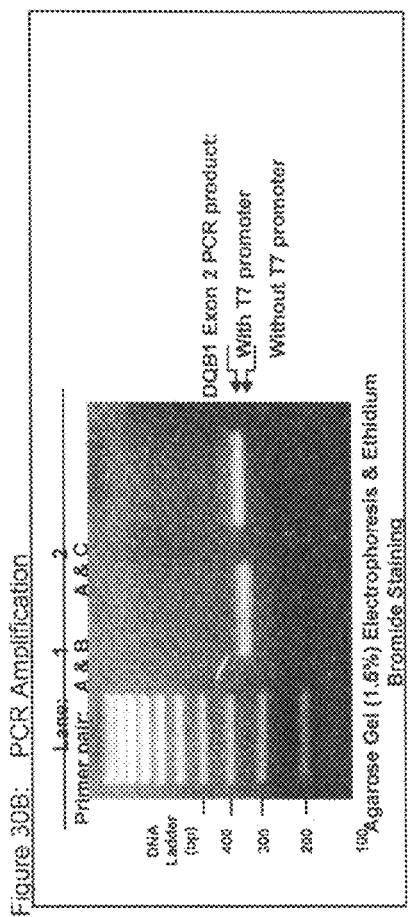
Figure 30B: PCR Amplification
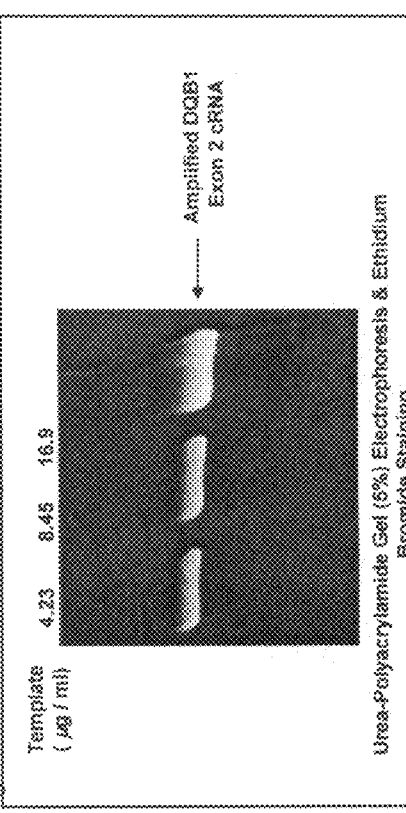
Figure 30C: In vitro transcription

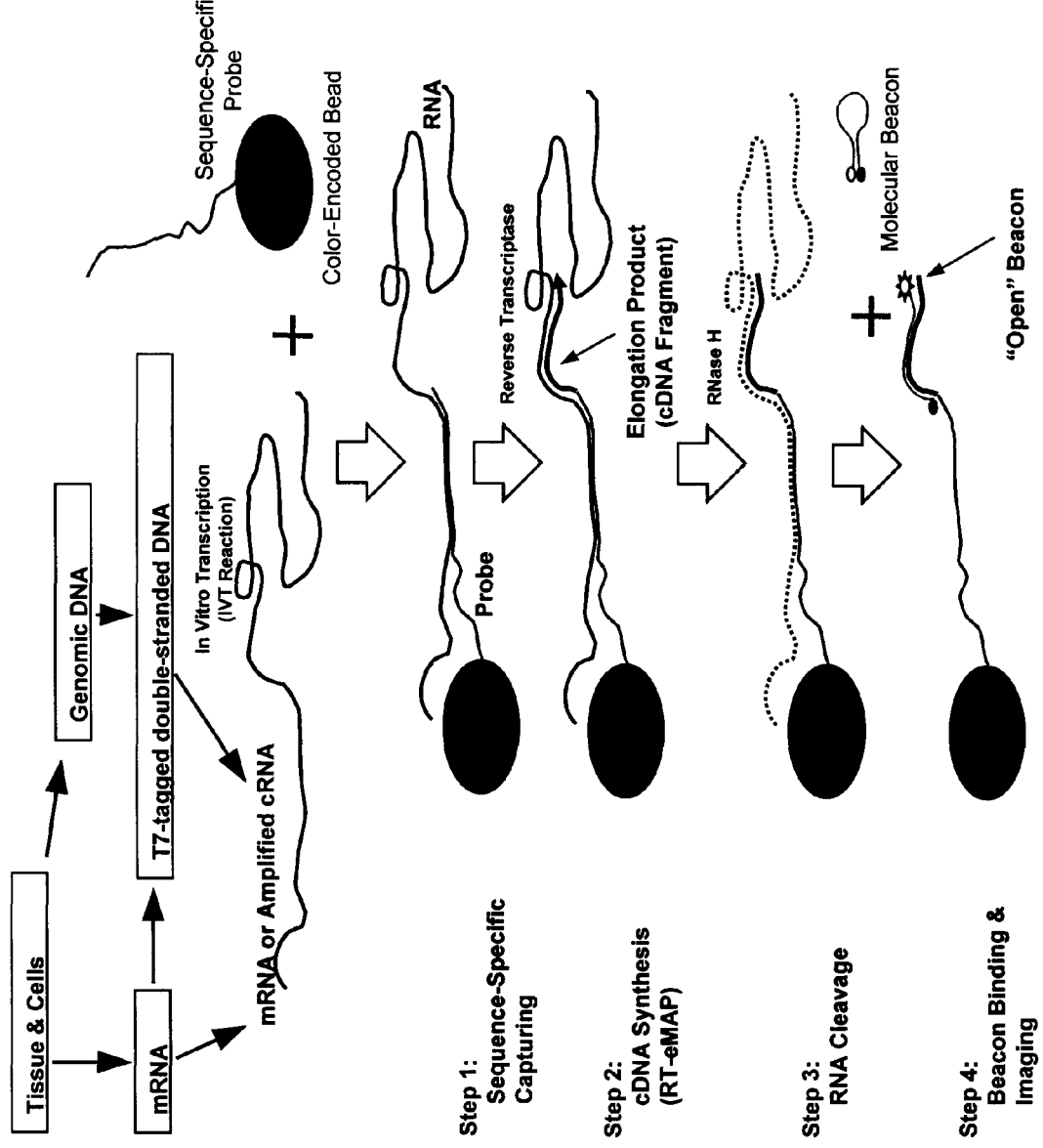
Figure 31: Molecular beacon detection of cDNA fragments in homogeneity RT-eMAP assay

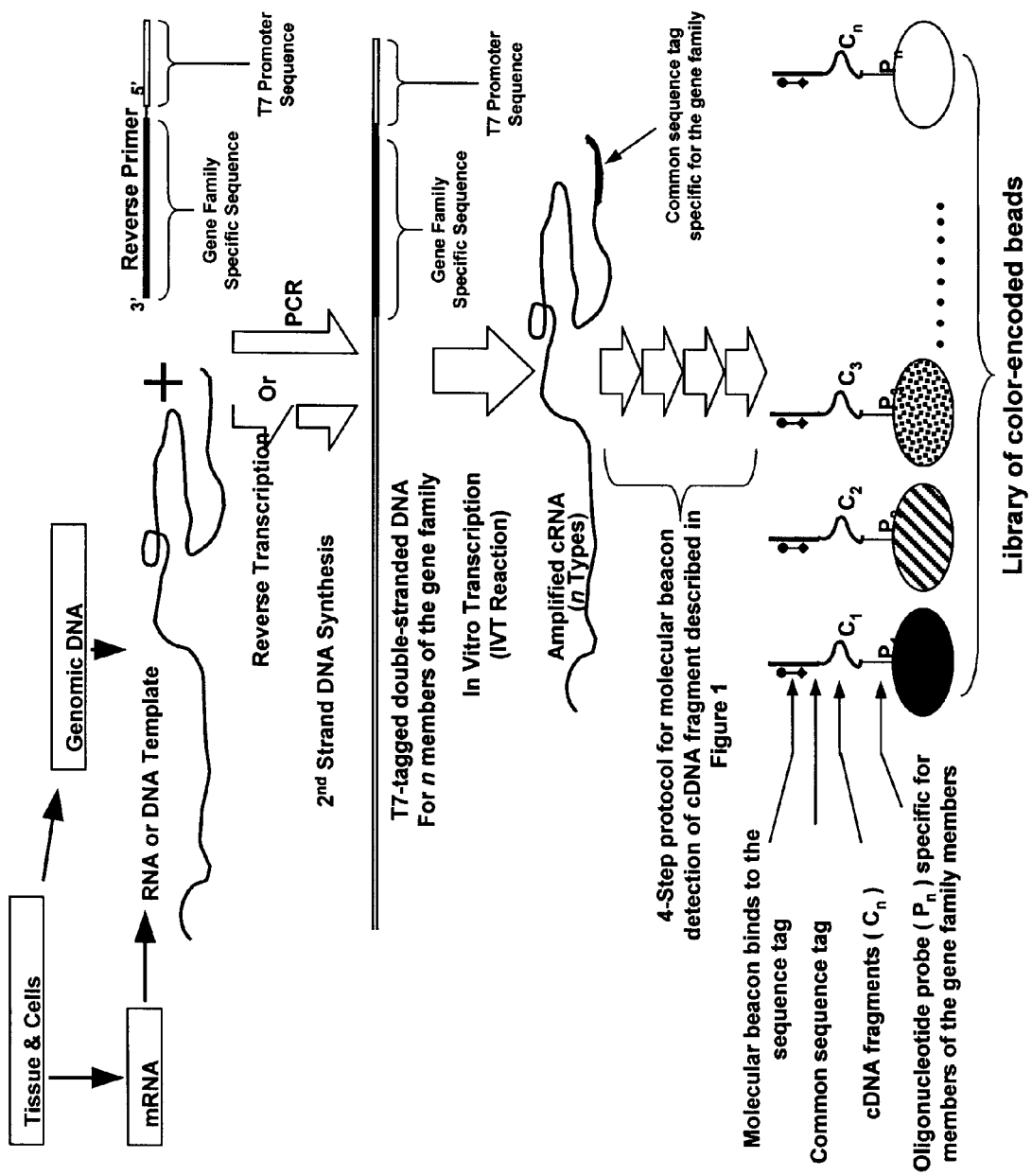
Figure 32: Molecular beacon detection of cDNA fragments amplified from a gene family

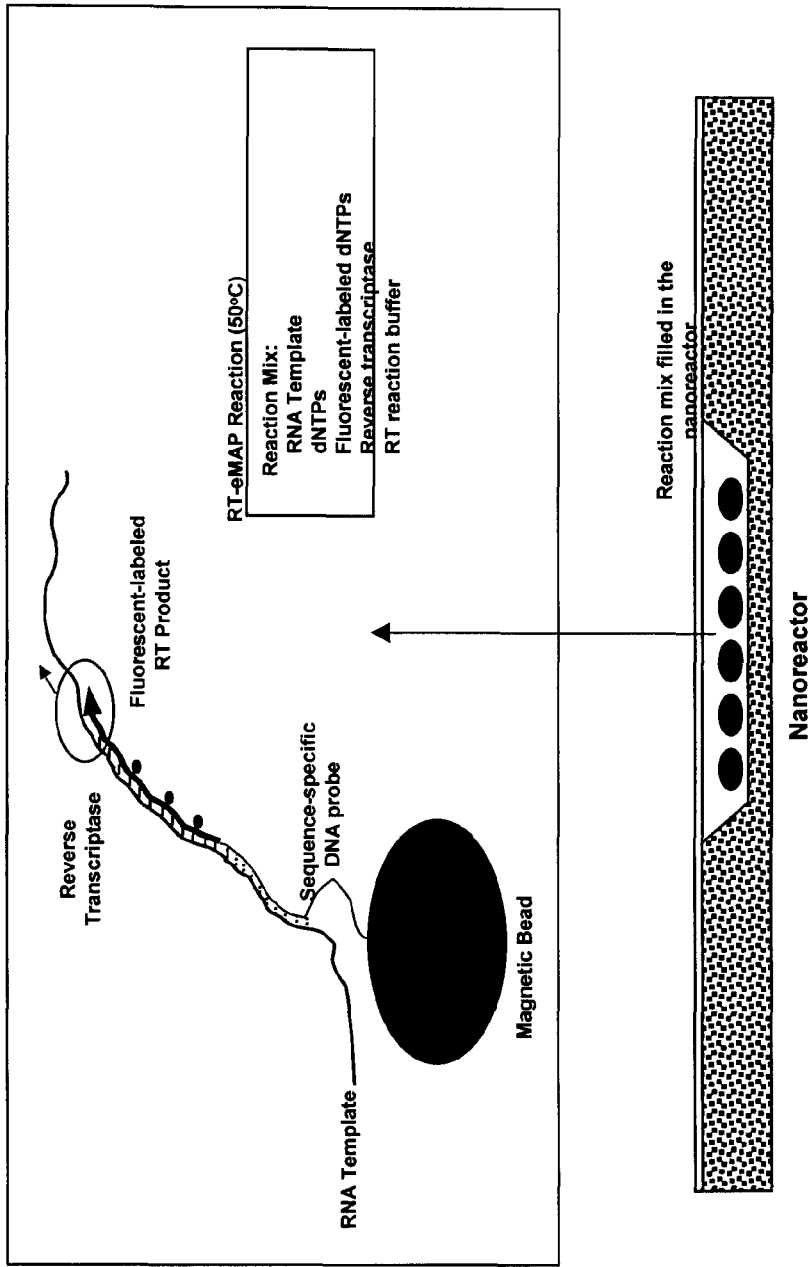
Figure 33: One-step on-chip RT-eMAP assay

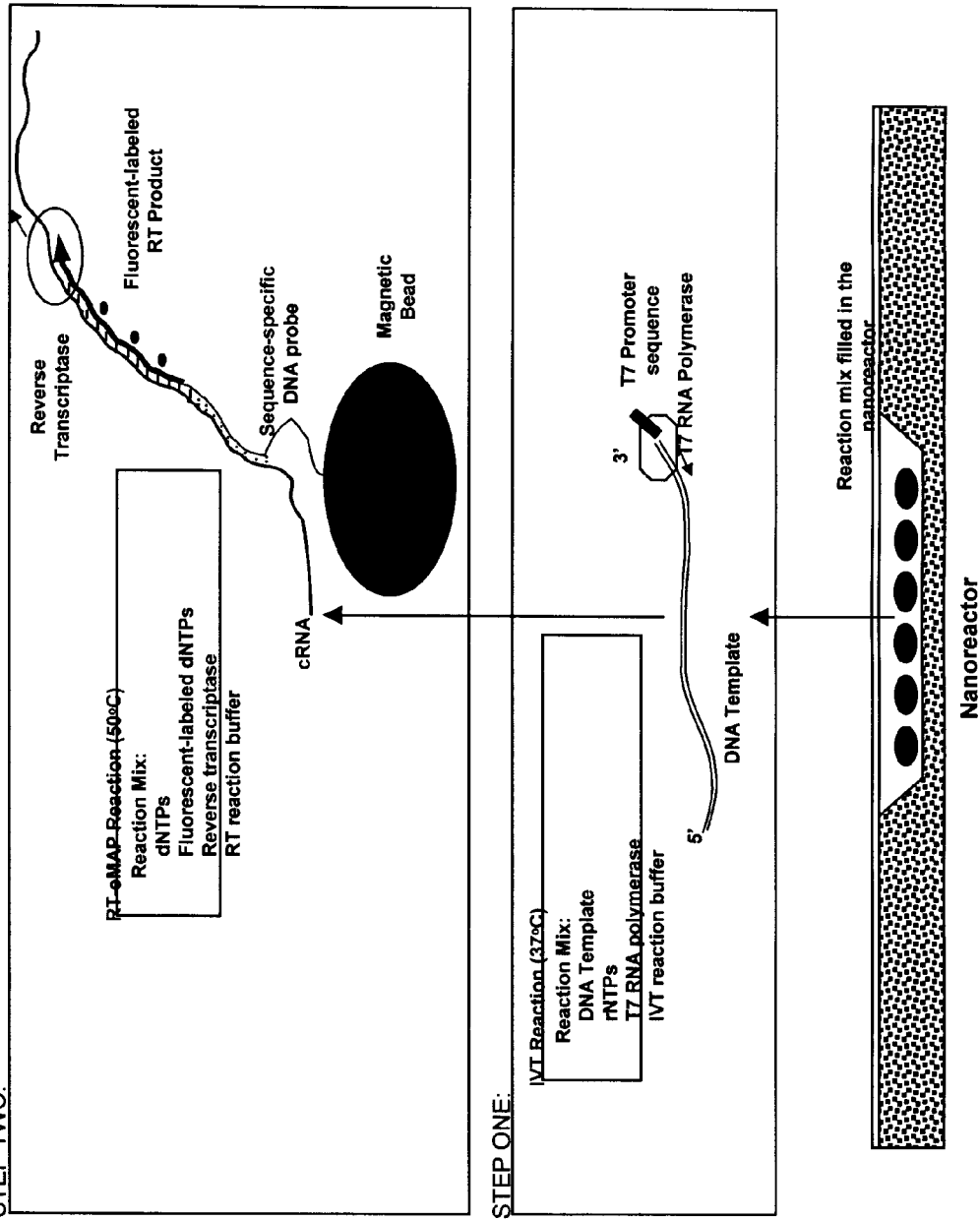
Figure 34  Two-step on-chip IVT-RT-eMAP assay

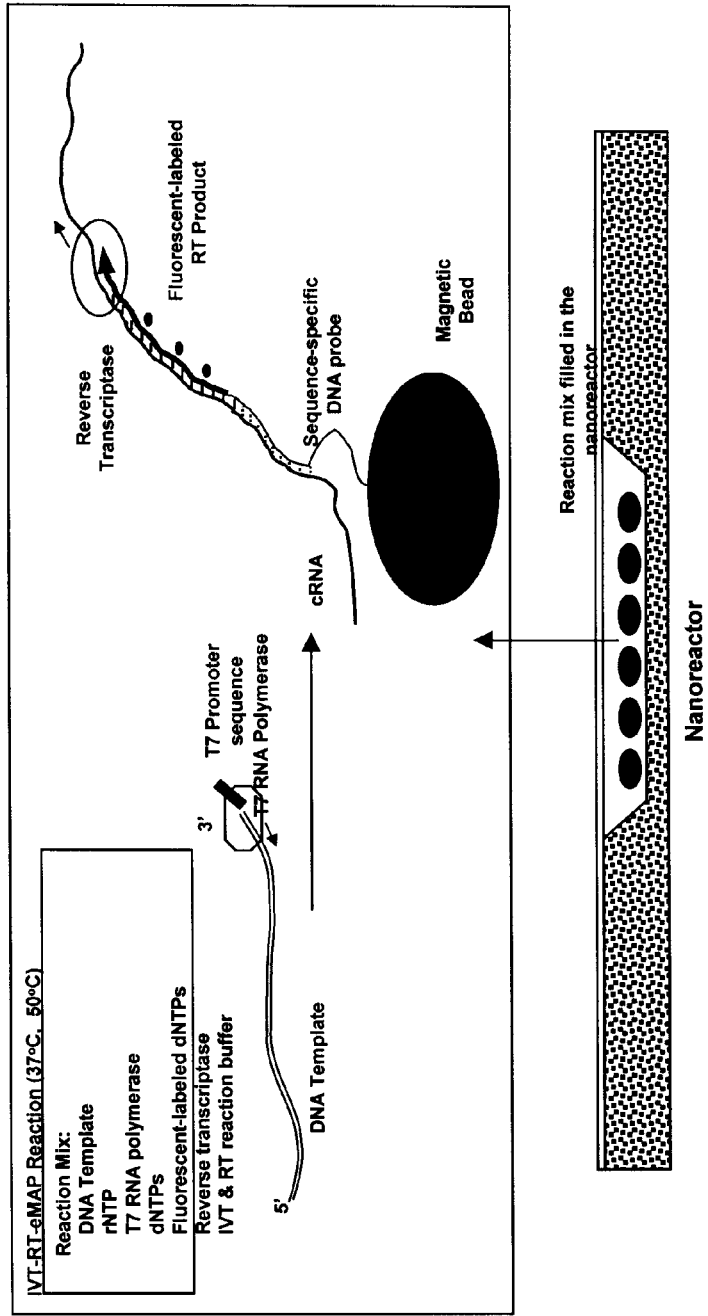
Figure 35: One-step on-chip IVT-RT-eMAP assay

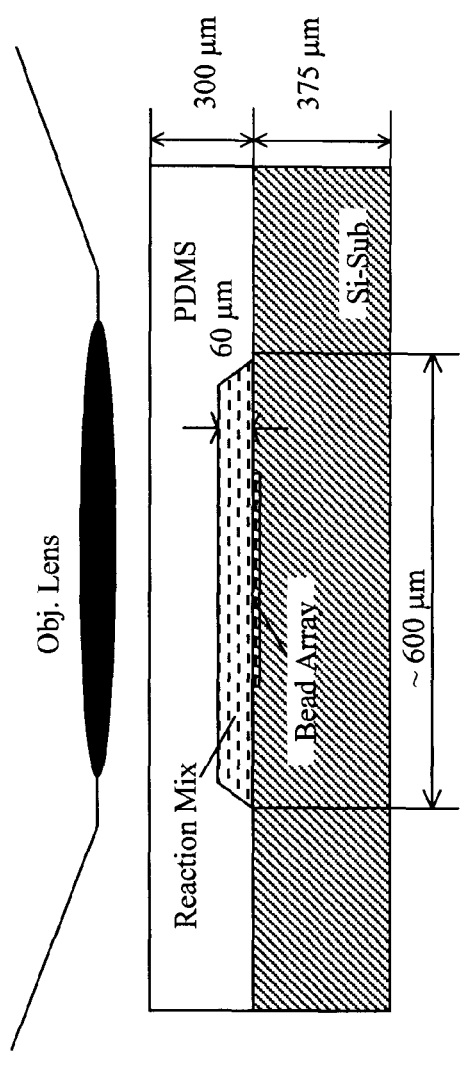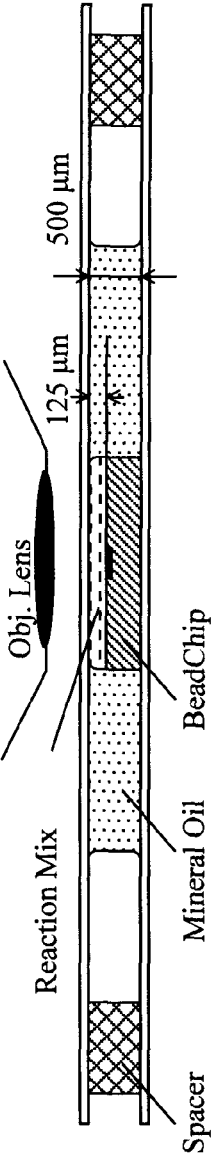
Fig. 38A: 30-nL Reactor
Fig. 38B: 0.5-ml Reactor

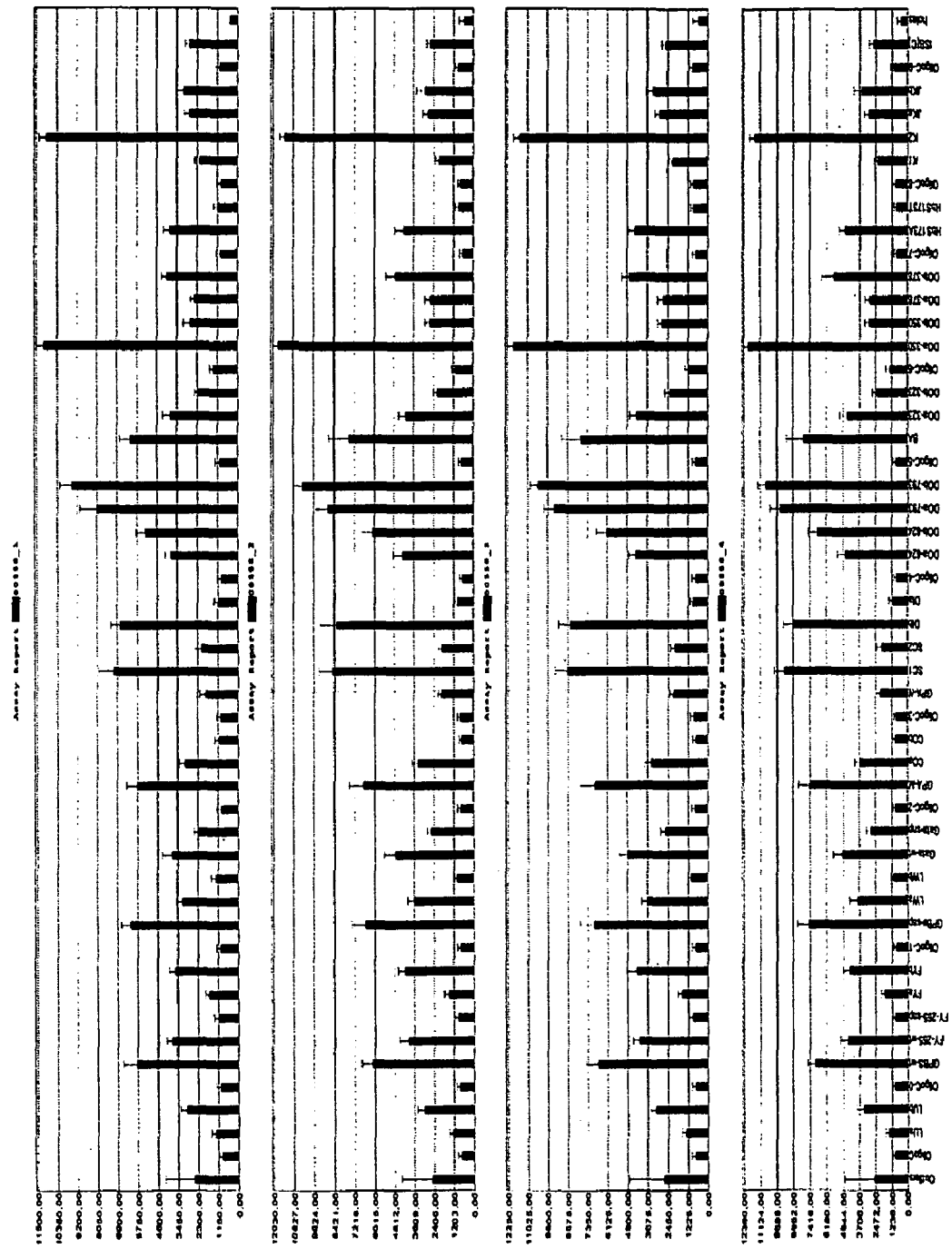
FIG 39: Assay Barchart of Chip No. 1 ~ 4

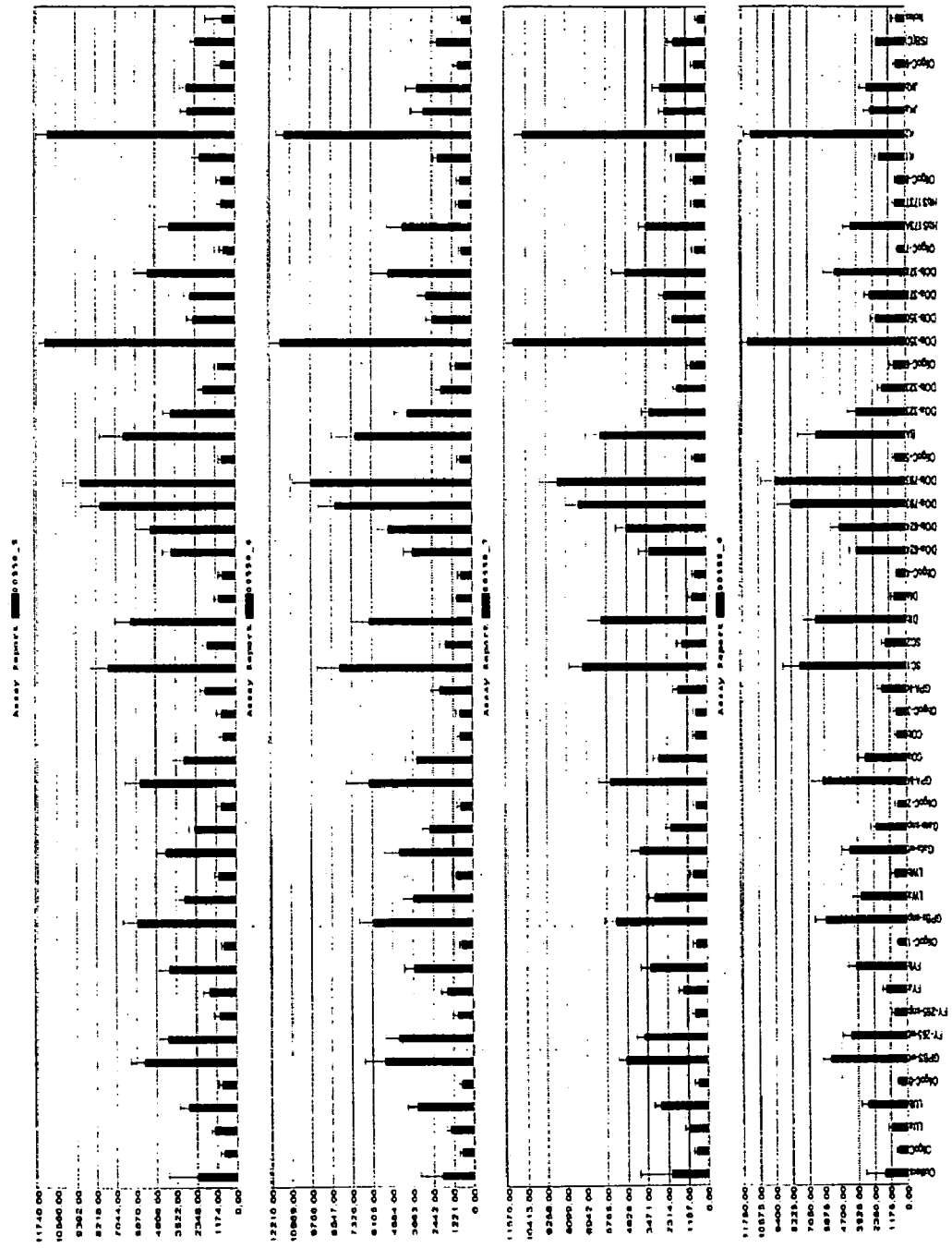
FIG 40: Assay Barchart of Chip No. 5~8

NUCLEIC ACID AMPLIFICATION WITH INTEGRATED MULTIPLEX DETECTION

RELATED APPLICATIONS

This application claims priority to two U.S. Provisional Applications, both assigned No. 60/606,666, and both filed Sep. 2, 2004, and to Provisional Application No. 60/628,464, filed Nov. 16, 2004, all of which are incorporated by reference.

BACKGROUND

1. References (All Incorporated by Reference)

The following can be referred to as background in order to aid in understanding of certain of the terms and expressions below.

- U.S. Patent Application (BioArray Solutions, hereinafter sometimes referred to as "eMAP®"): "Multiplexed Analysis of Polymorphic Loci by Concurrent Interrogation and Enzyme-Mediated Detection" filed Oct. 15, 2002; Ser. No. 10/271,602;
- U.S. Patent Application (BioArray Solutions): "Multianalyte Molecular Analysis Using Application-Specific Random Particle Arrays" filed on Aug. 23, 2002, Ser. No. 10/204,799 (discussing Random Encoded Array Detection, READ™);
- U.S. patent application (BioArray Solutions): "Multianalyte Molecular Analysis Using Application Specific Random Particle Arrays" filed on Dec. 28, 2001; Ser. No. 10/032,657
- U.S. Patent Application (BioArray Solutions, hereinafter sometimes referred to as "Multiplexed Expression Profiling"): "Optimization of Gene Expression Analysis using Immobilized Capture Probes," filed Oct. 26, 2004, Ser. No. 10/974,036, (including discussion therein relating to subtractive differential gene expression analysis; in the disclosure in the present application, sense and anti-sense strands are produced by incorporation of RNA pol promoter sequences);
- U.S. Patent Application (BioArray Solutions): "Arrays of Microparticles and Methods of Preparation Thereof," filed on Jul. 9, 2002; Ser. No. 10/192,352
- U.S. Patent Application (BioArray Solutions hereinafter sometimes referred to as "PARSE™"): "System and Method for Programmable Illumination Pattern Generation," filed Jan. 24, 2001, Ser. No. 09/768,414
- U.S. Pat. No. 6,251,691 (BioArray Solutions, hereinafter sometimes referred to as "LEAPS"): "Light Controlled Electrokinetic Assembly of Particles Near Surfaces": see especially FIG. 8;
- U.S. Patent Application (BioArray Solutions hereinafter sometimes referred to as "Solvent Tuning"): "Method for controlling solute loading of polymer microparticles" filed Jan. 21, 2003, Ser. No. 10/348,165
- U.S. Pat. No. 5,759,820 (Dynal AS) "Process for Producing cDNA"
- European Patent No. 0 368 906 B2 (Gingueras et al.; discussing isothermal, exponential amplification ("3SR"))
- Guatelli et al, "Isothermal, in vitro amplification of nucleic acids by a multienzyme reaction modeled after retroviral amplification", *Proc. Nat'l Acad. Sci. USA* 87, 1874-1878 (March 1990) (discusses invoking RNAseH activity)
- Kwoh et al, "Transcription-based amplification system and detection of amplified human immunodeficiency virus type 1 with a bead-based sandwich hybridization format", *Proc. Nat'l Acad. Sci. USA* 86, 1173-1177 (February 1989) (discussing transcription-mediated amplification using thermal cycling)
- U.S. Pat. No. 5,399,491 (Kacian et al.; discussing isothermal, exponential amplification) T Kievits et al., J Virological Meth 35 (Issue 3), December 1991, pp 273-286; EP 273086 (discussing NASBA)
- U.S. Pat. Nos. 5,716,785 and 5,891,636 (Van Gelder et al.); Van Gelder et al, "Amplified RNA synthesized from limited quantities of heterogeneous cDNA", PNAS 87, 1663-1667 (March 1990);
- Krieg & Melton, Functional messenger RNAs are produced by SP6 in vitro transcription of cloned cDNAs, Nucleic Acids Res 12, 7057-707 (1984) (discussing use of SP6, T4, T7 promoter sequences)
- Fermentas Life Sciences Website and references listed there (referred to in Ex. 1) include:
- Melton, D. A., et al., Efficient in vitro synthesis of biologically active RNA and RNA hybridization probes from plasmids containing a bacteriophage SP6 promoter, Nucleic Acids Res.,12, 7035-7056, 1984.
- Church, G. M., Gilbert, W., Genomic sequencing, Proc. Natl. Acad. Sci. USA, 81, 1991-1995, 1984.
- Peebles, C. L., et al., A self-splicing RNA excises an intron lariat, Cell, 44, 213-223, 1986.
- Melton, D. A., Injected antisense RNAs specifically block messenger RNA translation in vivo, Proc. Natl. Acad. Sci. USA, 82, 144-148, 1985.
- Krainer, A. R., et al., Normal and mutant human beta-globin pre-mRNAs are faithfully and efficiently spliced in vitro, Cell, 36, 993-1005, 1984.
- Witherell, G. W., et al., Cooperative binding of R17 coat protein to RNA, Biochemistry, 29, 11051-11057, 1990.
- Bernstein, E., et al., Role for bidentate ribonuclease in the initiation step of RNA interference, Nature, 409, 363-366, 2001.
- U.S. Pat. No. 6,013,431 (Soderlund, Syvanen)
- Pastinen T., et al., A system for specific, high-throughput genotyping by allele-specific primer exrtension on microarrays. Genome Research 2000 10:1031-1042

2. Discussion

Existing protocols for multiplexed interrogation of nucleic acid configurations—for example, those discussed in patent application Ser. No. 10/032,657 which use the Random Encoded Array Detection (READ™) format, where a bead array is formed on a substrate (a "BeadChip™")—generally invoke the conventional sequence of assay steps, i.e., separate DNA extraction and capture, amplification, post-amplification "clean-up" and finally, analysis by hybridization-mediated detection or capture-mediated probe elongation. In the READ format, assay signals reflecting the interaction of target(s) with an array of bead-displayed probes are generated on-chip and are recorded, by "snapshot" imaging of the array, without intervening sample transfers. This combination of analysis and read-out simplifies the protocol, decreases the time to completion of the assay and increases sample throughput.

The READ™ format is well-suited for the realization of miniaturized assays permitting rapid multiplexed analysis because an array of 10,000 microparticles (or "beads"), each of 3 micron diameter, occupies an approximate volume of only 300×300×5 $\mu m^3$ or ~0.5 nanoliters. Reducing assay volumes to nanoliter scale provides the advantage of requiring only small amounts of reagents generally, and requiring only a small number of target molecules for analysis. However, a significant set of problems arise on such miniaturization, notably including the design of functionally integrated assay protocols that combine multiple reaction steps in a single reaction without requiring intervening steps of sample manipulation.

Changing assay temperature, if needed to accommodate PCR for example, can cause significant evaporation and a correspondingly negative effect on the assay conditions. Methods of isothermal amplification, including the Transcription Amplification System ("TAS") described by Gingeras et al. and others (see references above) have the advantage of largely eliminating design constraints arising from the variation in effective "melting"-temperatures of the amplification products (see U.S. Ser. No. 10/974,036, Multiplexed Expression Profiling, for discussion regarding effective melting temperatures). Isothermal amplification also eliminates the need for carefully controlled heating and rapid cooling of the reaction in each cycle to avoid excessive evaporation and unacceptable increases in solute concentration in the reaction mixture. The elimination of the rapid cooling step eliminates a cumbersome constraint from the design of the reaction vessel for integrated reaction protocols, which otherwise must provide for rapid heat transfer to an active cooling device while permitting optical access to the reaction, so as to permit recording or real-time monitoring of the reaction products and assay results. However, for TAS and related methods of exponential isothermal amplification, performance critically depends on maintaining strict assay conditions including (constant) temperature, pH and ionic strength, including allowing only a limited range of probe and primer lengths. When contemplating homogeneous multiplexed formats of TAS, capture probess and primers for reverse transcription and second strand cDNA synthesis both bind to RNA generated in the IVT step, and this can reduce the amount of the anti-sense RNA product detected. These limitations make the TAS difficult to multiplex, as is needed in commercial applications.

With linear IVT amplification, performed in the conventional formats which typically call for tens of microliters of analyte solution, it is questionable if, in a reasonable timeframe, a sufficient amount of product is generated to obtain a detectable assay signal. One would generally have a sample of genomic DNA sample for the IVT assay, in low concentration, meaning that in a small volume, there would be relatively few molecules in total. Thus, a miniaturized format presents a special set of problems, which must be solved to have an effective process for use in a commercial setting.

Other problems with miniaturization of an IVT or TAS system relate to the mixing of the assay reagents, which cannot be accomplished with conventional mechanical methods due to the small volume involved. Diffusion alone must be relied upon to provide sufficient mixing in a sufficiently short period of time to bring assay reagents into contact such that they can react and form a detectable amount of product in the available time for completion of the assay.

An additional challenge arises because in a miniaturized format, the assay system needs to be "closed" to minimize contamination and evaporation. Thus, for a miniaturized assay, as it is difficult to monitor the reaction and correctly time subsequent addition of reagents throughout reaction, and with conventional apparatus, it is impractical to add nanoliter quantities of reagents in the course of the reaction. This can be accomplished with an integrated homogeneous assay format conducted in a hermetically sealed reactor, in which reagents are not added during the reaction process, but rather are all placed in the reaction solution at the start of the reaction process.

Assay integration in hermetically sealed reactors is desirable to minimize the number of manipulations, hence risk of operator error, and to minimize assay contamination risk, and the risk of contamination of the assay operator (which is especially significant in viral load assays).

SUMMARY OF THE INVENTION

A method mediated with in-vitro transcription ("IVT") which permits the miniaturization of multiplexed DNA and RNA analysis, and in which elongation-mediated multiplexed analysis of polymorphisms (eMAP™) is used as the analysis step, is described. The method relates more particularly to the integration of linear amplification and multiplexed analysis of amplification products.

A method mediated with IVT is further disclosed herein for selecting a designated strand from T7-tagged double stranded DNA: wherein, the selected strand forms the template for RNA synthesis. In one embodiment, double stranded DNA incorporating the T7 (or other) promoter sequence at the 3' end or the 5'end is produced, for example, by amplification of genomic DNA using the Polymerase Chain Reaction (PCR). An IVT reaction produces as many as $10^3$ copies of sense or anti sense RNA from each double stranded T7-tagged amplicon, depending on the placement of the promoter sequence. Selection of one strand is desirable in order to minimize re-annealing of targets into a double-stranded configuration, a process that competes with capture of the target to a probe (as needed for analysis). In multiplexed analysis, involving the analysis of multiple variable sites on one or more targets with a set of probes in the same reaction, the selection criteria for the selected strand may include minimizing cross-reactivity with probes other than the probe designed to capture that strand. In addition, strand selection is desirable in order to minimize potential deleterious effects arising from the close proximity of multiple variable sites such as Single Nucleotide Polymorphisms (SNPs) on the same strand; but not present on the other strand (see e.g. U.S. application Ser. No. 10/271,602, filed Oct. 15, 2002, entitled: "Multiplexed Analysis of Polymorphic Loci by Concurrent Interrogation and Enzyme-Mediated Detection.").

Also disclosed are nested PCR designs permitting allele analysis in combination with strand selection by IVT; the advantage being that a clean-up step is not required. As described herein, PCR is conducted to amplify a double-stranded genomic DNA sample, using conventional "outside" forward and reverse primers, as well as "inside" (or "nested") forward and reverse primers which include the T7 promoter sequence. The nested primers are allele-specific so that each primer contains, at or near its 3' terminus, a "stop-go" nucleotide which is complementary to either the normal or variant form of the respective primer's target DNA strand. Only nested primers matching the target DNA strand at the "stop-go" nucleotide form T7-tagged products, which are then detected following strand selection using an IVT reaction. The strands detected with this method reflect the allele configuration in the sample: for example, the presence of both RNAs (transcribed from both T7-tagged strands) represents a heterozygote. In this manner, a combination of IVT and RT-eMAP, following PCR, can be used to detect single nucleotide polymorphisms (SNPs) and permit a determination of the allele configuration at a particular site of interest without requiring "clean-up," so long as the PCR reaction is adjusted not to leave a large excess of unconsumed primers.

In an embodiment of the assay system, multiple copies of an anti-sense or a sense RNA product are selectively produced by IVT and analyzed—preferably concurrently as described herein—using a set of encoded reverse transcription (RT) primers, preferably displayed on color-encoded microparticles ("beads"). In this reaction, a set of amplicons are first generated by PCR, and these amplicons are the ones which serve a template for RNA polymerase, to generate the anti-sense or a sense RNA, as desired. This selection step is accomplished by selecting a set of PCR primers, one of which includes a transcription promoter sequence (e.g., T7) and one of which does not. In the amplicons generated, one will serve as a template strand. Detection can be accomplished using RT primers matching their captured RNA targets are elongated to form cDNA strands attached to the encoded beads (using an eMAP® reaction).

Also disclosed are formats of integrating the step of nucleic acid (RNA and DNA) amplification, preferably by in-vitro Transcription (IVT) of a double-stranded T7-tagged DNA template, with the step of multiplexed analysis of amplification products, preferably by way of eMAP, preferably realized, as described herein, by way of reverse transcription ("RT")-mediated elongation ("RT-eMAP") under substantially isothermal conditions, i.e., without temperature cycling. Amplification and detection can be performed concurrently, in what is also referred to herein as a homogeneous format. The functional integration of amplification and analysis as disclosed herein permits the miniaturization of the assay configuration to volumes as low as 30 nl and generally to volumes in the range of 1-100 nl. Confinement of the amplification reaction to a small volume brings the significant advantage of reducing the number of target molecules required to produce a detectable assay signal. As described herein, IVT performed at nanoliter scale, suffices to generate product from typical initial concentrations of genomic material to attain nanomolar target concentrations, readily detectable in the READ™ format of multiplexed analysis (U.S. Pat. No. 6,797,524). For example, if one starts with a sample having about $10^5$ molecules in a volume of 1 μl, which is $10^3$ molecules in 10 nl, following IVT amplification (the IVT reaction generates about $10^3$ products per template), one obtains about $10^6$ molecules in 10 nl, which is within assay detection limits (see for example the "Multiplexed Expression Profiling" Application for experimental results relating to detection limits).

These RT-eMAP protocols are well-suited for miniaturized assay formats of genotyping and expression monitoring, permitting the delivery of complex assays in a self-contained, disposable fluidic -cartridge, obviating the need for exponential amplification. The advantages of the IVT RT-eMAP protocol described herein include the fact that the reactions can be conducted isothermally, and are suitable for use in a "closed" environment (i.e., pipetting, which can open the system to contamination, is not required).

Given their comparative simplicity, IVT designs and protocols are preferable to the complex protocols and designs of the known variants of a Transcription Amplification System (TAS). However, when desirable, sensitivity can be enhanced by exponential nucleic acid amplification (RNA or DNA). In one embodiment of a homogeneous format for TAS and multiplexed detection, encoded beads display "looped" capture probe configurations permitting the generation of a signal upon capture of RNA product and real-time assay monitoring.

Single-tube and homogeneous assay formats, like IVT-RTeMAP, permit automation and functional integration of multiple steps in an assay protocol or in a reaction sequence. Especially for a homogeneous assay format—carried out in "one-step" where all reagents are present in a reaction mixture at the start of the reaction—one minimizes sample handling, thereby simplifying and accelerating the procedure while reducing the risk of exposure to infectious agents as well as the risk of operator error. In addition, the time required to complete the assay, as well as the requisite consumption of reagents, are minimized.

BRIEF DESCRIPTION OF THE FIGURES

FIGS. 17A to 17C show a comparison of results from an on-chip multiplex RT-eMAP assay with a two-step on chip IVT RT-eMAP assay and a one-step on chip IVT RT-eMAP assay. Here and, unless otherwise indicated, in other bar chart displays, the bars represent average fluorescence signals associated with cDNA products produced by RT-mediated on-bead probe elongation, and the error bars represent the standard deviation of the mean intensities across the set of beads displaying the same probe.

FIG. 18 shows an in tube reaction demonstrating IVT where cRNA is used as the template. The gel shows that amplification took place.

FIGS. 22A to 22C show an RT-eMAP assay with TAMRA dye or Cy3 dye on the dNTPs which are incorporated into the elongated primers (Cy3-labeled dNTPs are preferentially incorporated for each of the primers).

FIG. 29 shows a two-step two-temperature on-chip IVT-RT eMAP assay, where dsDNA is the starting material for generating an amplified RNA template for the RT-eMAP assay.

FIG. 30A to 30C depict the PCR design where dsDNA is the starting material for the IVT-RT-eMAP assay, and results in a gel, and IVT results.

FIG. 31: depicts molecular beacon detection of cDNA fragments in an RT-eMAP assay.

FIG. 32: depicts molecular beacon detection of cDNA fragments, amplified from a gene family, in an RT-eMAP assay.

FIG. 33 depicts a homogeneous assay, i.e., a one-step on-chip RT-eMAP assay, carried out in a nanoreactor under isothermal conditions.

FIG. 34 depicts a two-step on-chip IVT RT-eMAP assay, carried out in a nanoreactor.

FIG. 35 depicts a homogeneous assay, i.e., a one-step on-chip IVT RT-eMAP assay, carried out in a nanoreactor at two different temperatures.

FIG. 38A depicts a cross-sectional view of an exemplary 30 nl reactor.

FIG. 38B depicts a cross-sectional view of an exemplary 0.5 ml reactor.

FIGS. 39 & 40 show the assay results of various BeadChips (as indicated) following reaction in the reactors (such as those shown in FIGS. 38A & 38B).

DETAILED DESCRIPTION

Figure 1:
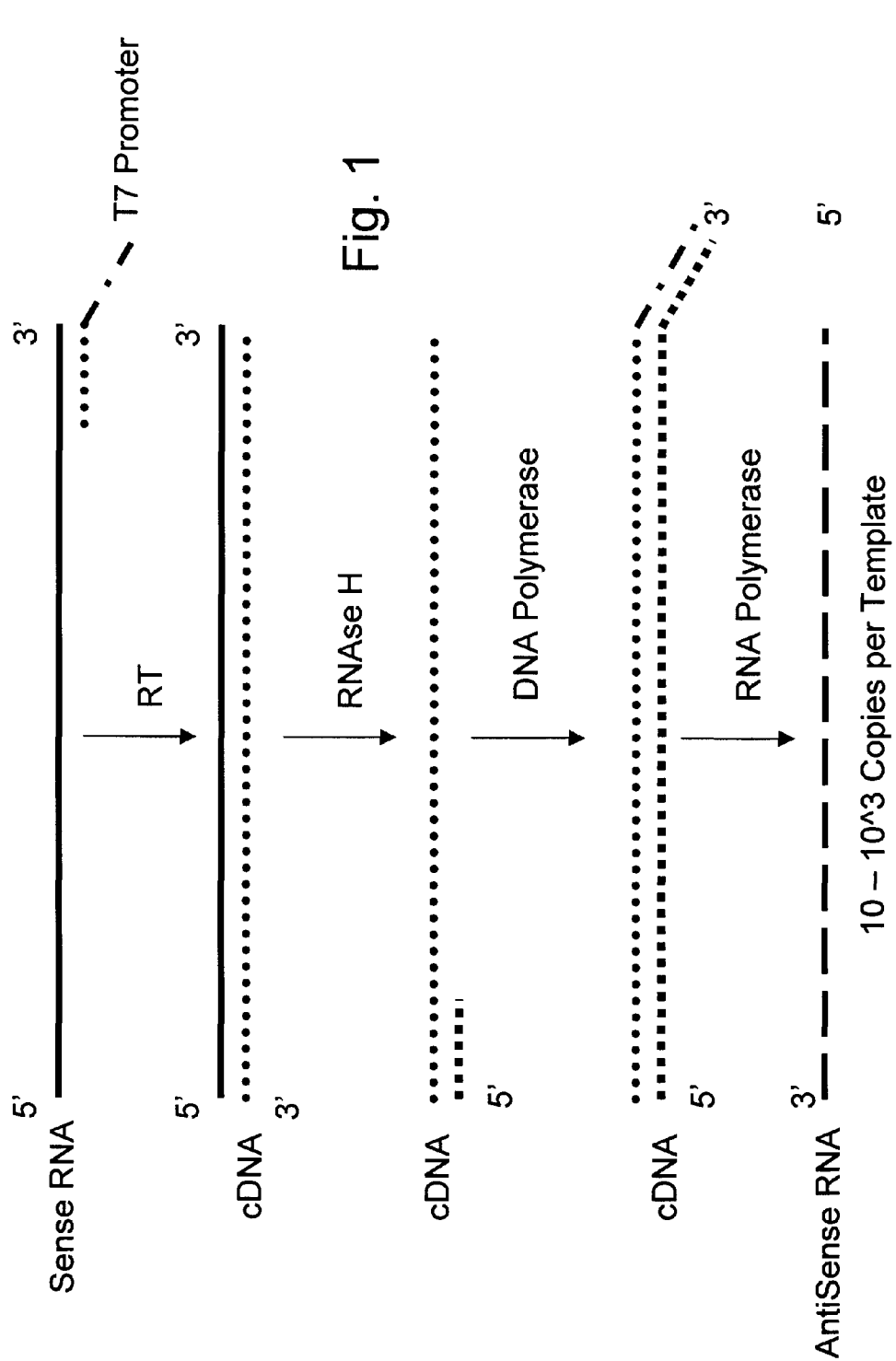
FIG. 1 depicts production of antisense RNA from sense RNA with linear amplification using the IVT method.

The methods and compositions disclosed herein represent several substantial improvements to elongation-mediated multiplexed analysis of polymorphisms (eMAP®), as disclosed in Ser. No. 10/271,602; namely: miniaturization of eMAP, strand selection by way of In Vitro Transcription (IVT) of the selected ("template") strand, and several assay formats permitting the functional integration of IVT with a reverse transcription catalyzed probe elongation, also referred to herein as RT-eMAP, equivalent to on-bead cDNA synthesis, for allele-specific detection.

Detection and identification of multiple specific subsequences can be performed using, e.g., eMAP, which invokes the 5'→3' elongation of sequence-specific probes immobilized on color-encoded or otherwise decodable beads, by a DNA polymerase or reverse transcriptase, using, respectively, DNA or RNA as a template. The embodiment of eMAP using RNA as a template is referred to as RT-eMAP®. This embodiment generates cDNA as an elongation product, and RT-eMAP can be used for the multiplexed analysis of polymorphisms and mutations within the RNA template, as well as for multiplexed gene expression analysis.

The integrated, miniaturized assay formats disclosed herein can be used for a variety of DNA or RNA analysis by multiplexed genotyping or gene expression analysis, including a wide variety of assays for diagnosis of disease or other condition, prognosis of disease progression and treatment response, based on the genomic materials, and the screening for, and genotyping of, viral or bacterial pathogens including but not limited to those listed in Table II. Elongation-mediated multiplexed analysis (eMAP) of nucleic acids can be performed concurrently with amplification of genomic material, and is useful for detection and analysis with the amplification system disclosed herein. Methods of combining amplification and multiplexed detection to the quantitative analysis of gene expression levels, a methodology of increasing utility in furthering the fundamental understanding of the molecular mechanisms of complex diseases such as cancer, is disclosed in greater detail in provisional application Nos. 60/606,666.

Random Encoded Array Detection (READ)—In one embodiment using color-coded beads, bead-displayed cDNA products formed by RT can be detected, either subsequent to completion of the IVT-RT-eMAP assay, or in the course of the assay ("real time"), using the READ format. In the READ assay format, microparticles are employed for the sequence-specific capture of selected RNA or gDNA subsequences, for example from a cell lysate (See U.S. Pat. No. 6,797,524; WO 01/98765; U.S. Ser. No. 10/032,657). With miniaturization, the functionally integrated sequence of reaction steps involved in IVT-eMAP assay are performed in a homogeneous manner; that is, without intervening separation or washing steps. When using READ for detection in a miniaturized assay format, the results are recorded in one pass, for example, by imaging the entire bead array in one field under an objective lens.

1—Miniaturization of eMAP Reaction to Submicroliter Volumes

Disclosed are methods and devices for miniaturization of eMAP, and alternative eMAP designs also disclosed herein and referred to as RT-eMAP designs, to reaction volumes of 1-100 nanoliters so as to obviate the need for exponential amplification and associated temperature cycling. These methods include designs for the fabrication of such a reactor by "micromachining" of silicon, and processes and protocols for performing molecular analysis in such a reactor including a method of post-assay ("real-time") assembly of planar assemblies of magnetic microparticles displaying RT primers.

Miniaturization of Integrated Assays: Obviating the Need for Exponential Amplification—In the READ or PARSE™ formats, depending on the fluorescent dyes used, the nature of the CCD or other detection elements employed, and the magnitude of the relevant affinity constants governing analyte capture, $\sim 10^3$ molecules suffice to produce a readily detectable optical signature. Thus, in a sequence-specific amplification format, sensitivity—which is related directly to the extent of the proliferation of templates—is less important than specificity—which is related to the enhancement of the subsequence of interest over the potentially interfering subsequences represented in the original target material, which may also be amplified.

In conventional assay formats, amplified target is released into a finite reaction volume; typically of the order of 10 μl. Given that the typical effective affinity constants of oligonucleotide probe-target interactions are about $10^8$/M (see Multiplexed Expression Profiling), it is the capture of amplified subsequences ("templates") to solid phase carrier-displayed probes which limits the sensitivity of such "reverse dot-blot" assay designs. Thus, in conventional designs, such as those disclosed in the Background of application Ser. No. 10/847,046 (hMAP), and in the Background of the eMAP application, a large number of templates are produced to overcome the inefficiency of the capture step, inasmuch as the capture step is performed in "macroscopic" volumes of about 1-10 μl.

Integration of target amplification and multiplexed detection, with concomitant miniaturization of the reaction to typical volumes of 1-10 nl, directly reduces the degree of requisite target amplification. That is, if 1 femtomole ($10^9$ copies) of amplified target is required in a 10 μl reaction (see discussion of this topic in Multiplexed Expression Profiling) to ensure capture of $\sim 10^3$ copies to carrier-displayed probes for detection, then about $10^6$ copies should suffice in a 10 nl reaction given typical quantities of genomic material of 100 ng/ml, linear amplification with a gain of $10^3$ will suffice to produce a requisite number of templates, obviating the need for exponential amplification. The formula for determining the number of molecules required for the assay is as follows: C min (detection limit)=N (number of molecules)/Vmax.

One method of miniaturization disclosed herein places the homogeneous IVT-RT-eMAP assay format, disclosed herein below, or, more generally, a capture-amplification-detection reaction sequence, into the nanoliter reaction volume including RT primers displayed on color-coded beads. The nanoliter reaction volume ("nanoreactor") is fabricated by micromachining a recess in a silicon chip (see, e.g., Ser. Nos. 10/032,657; 10/192,352). Details of the fabrication methods, and methods of charging the nanoreactor are described in Example IV below.

Figure 6:
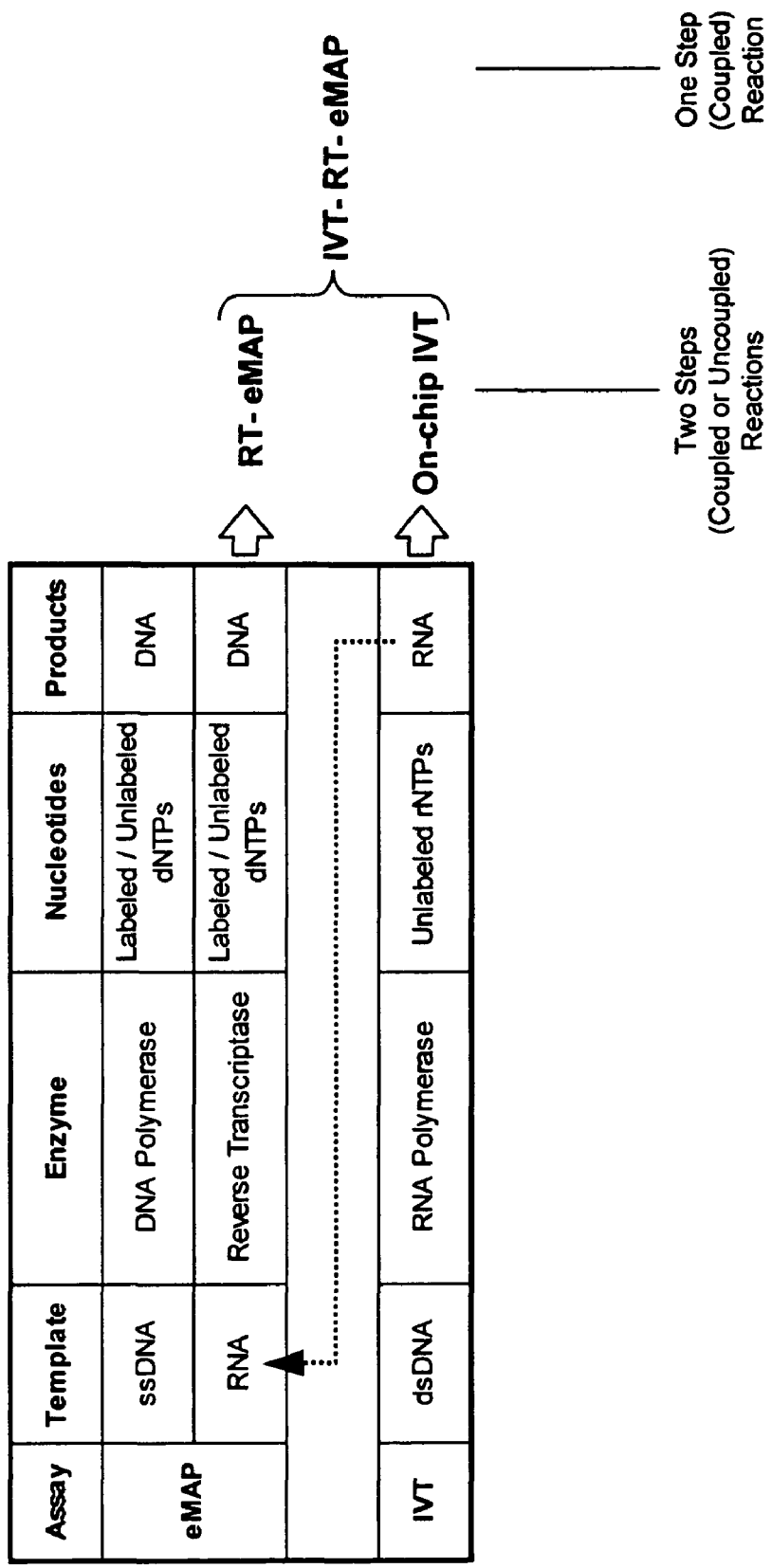
FIG. 6 the design of various on chip IVT RT-eMAP assays, both two step and one-step.

In FIG. 6, a sequence of steps for integrated nucleic acid analysis is illustrated which invokes the post-array assembly of a planar array of color-encoded particles (see LEAPS; U.S. Pat. No. 6,797,524). In the capture step, sequence-specific probes immobilized on color-encoded beads bind to target RNA isolated from tissue and cells, or generated from the IVT reaction. In the transformation step, complementary DNAs are synthesized by RT with the captured RNA acting as templates. In the array assembly step, color-encoded beads displaying the complementary DNA are assembled into planar arrays. In the detection assay step, signals from the set of beads on the chips are detected, and the bead identities are decoded, using known methods.

2—Combination of IVT and Reverse Transcription Catalyzed eMAP (RT-eMAP)

IVT is a well-known method for large-scale synthesis of RNA molecules and provides an efficient method for nucleic acid amplification. In an IVT reaction, double-stranded DNA containing a bacterial phage promoter sequence, e.g., the T7 promoter, at the 5' end serves as a template to synthesize multiple copies of complementary RNA (cRNA) in an RNA-polymerase catalyzed reaction. Suitable RNA polymerases and their corresponding promoter sequences, have been previously identified, e.g., TA, T7, Sp6. Like DNA polymerase, RNA polymerase uses one of the strands of the double-stranded DNA as a template for synthesis of new strand of nucleic acid. However, unlike DNA polymerase, RNA polymerase, under isothermal conditions, generates multiple new strands of RNA which are not attached to the DNA template. Typically, RNA polymerase, using, for example, the T7 promoter, produces several hundred copies of RNA from one dsDNA template, resulting in linear amplification of the template.

In the IVT reaction, reagents typically include DNA templates containing a promoter sequence such as T7 and SP6 promoters (RNA can also function as the template), ribonucleotide triphosphates (rNTPs), a buffer system that includes DTT and magnesium ions, and an appropriate RNA polymerase, derived from phage. Unlike PCR which requires thermal cycling, the IVT reaction is performed under isothermal conditions at a pre-selected temperature, and this facilitates the coupling of IVT to other enzymatic reactions, such as eMAP, as described herein. To transcribe RNA into DNA in vitro using a homogeneous format, the additional necessary reagents are included in the initial reaction mixture and the procedure outlined in FIGS. 1 and 2 is performed.

In step 1, a T7-promoter-tagged (anti-sense) reverse transcription primer anneals to a complementary sequence at the 3' region of a (sense) RNA strand of interest. Reverse transcriptase catalyzed reverse transcription generates complementary DNA (cDNA), by elongating the 3' end of the T7-tagged primer, using the sense RNA as a template.

In step 2, RNAse H degrades the RNA within the RNA-DNA heteroduplex formed in Step 1 which is thereby converted into single-stranded cDNA. This conversion can be brought about by adding RNase H, or by using a reverse transcriptases, e.g., Moloney Murine Leukemia Virus (M-MLV) reverse transcriptase, having RNase H activity. Following conversion, a forward primer (having a sense sequence) which can anneal to a specific selected sequence within the 3' region of the cDNA, is used to initiate $2^{nd}$ strand DNA synthesis, catalyzed by the DNA polymerase activity of reverse transcriptase, using the cDNA as a template. Each initial RNA sequence is thus "copied", in a 1:1 ratio, into one copy of double-stranded DNA having a T7 promoter region at the 5' end.

Figure 2:
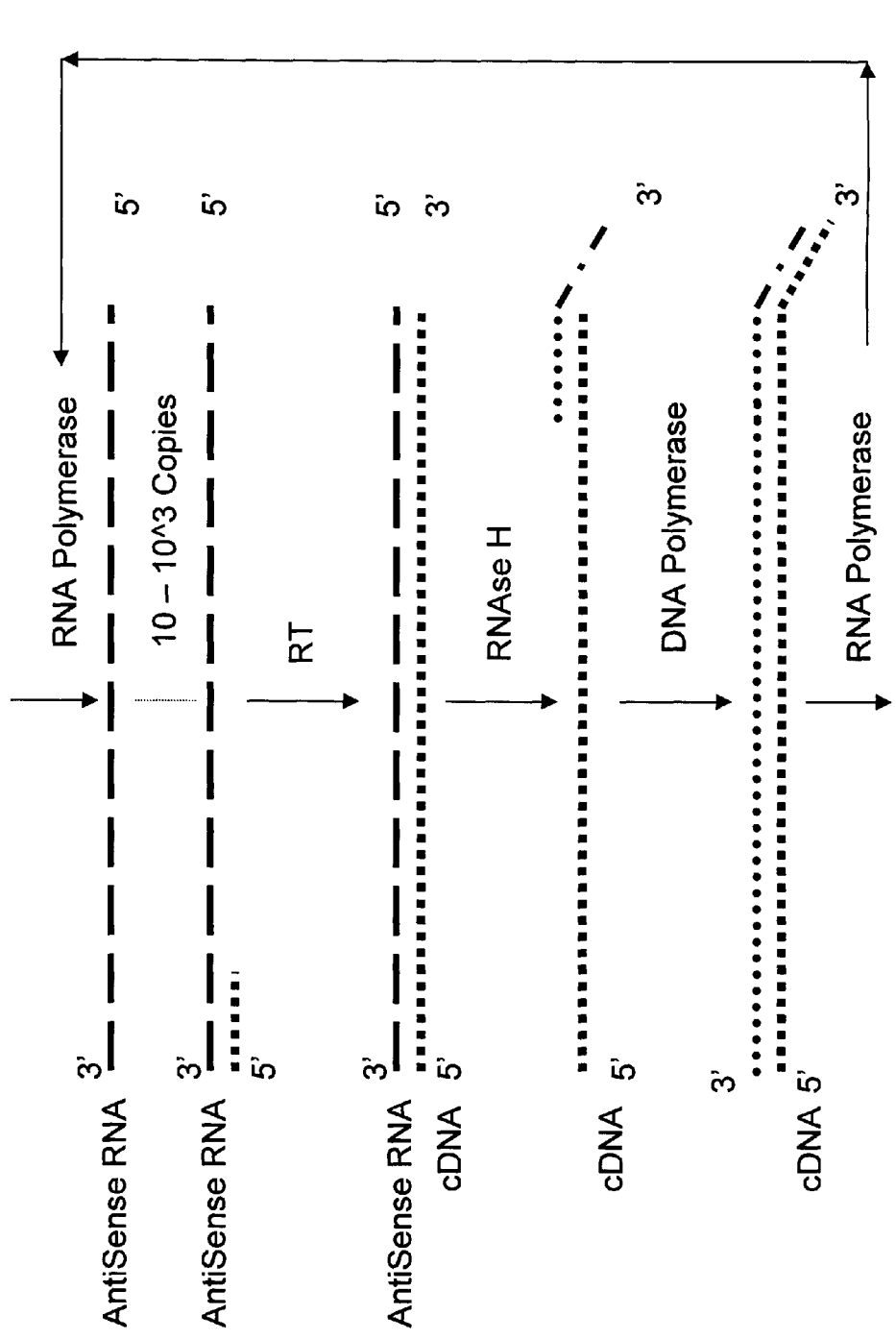
FIG. 2 depicts exponential amplification of RNA with the IVT method.

In step 3, transcription of each of the T7-tagged double-stranded DNAs produces typically up to $10^3$ copies of anti-sense RNA, catalyzed by T7 RNA polymerase (see FIG. 1).

For exponential amplification, in accordance with one of the versions of a Transcription Amplification Systems (TAS), two additional steps are performed.

In step 4, forward primer (Step 2) anneals to each of the antisense RNAs as the initiation step for synthesis of new sense cDNA. The product is a RNA-DNA complex in a 1:1 ratio relative to the antisense RNA formed in Step 3 (see FIG. 2). The forward primer(s) can be tagged for identification, as can the reverse primer(s).

In step 5, following degradation of RNA within RNA-DNA hybrids by the RNAse H activity of reverse transcriptase, T7-tagged reverse transcription primer (Step 1) anneals to the newly synthesized sense cDNA formed in Step 4, to initiate synthesis of a first, and then, via the forward primer (Step 2), double-stranded cDNA. As for the cDNA product formed in Step 2, the resulting double-stranded DNA has a T7 promoter region at the 5' end and thus serves as a template for synthesis of additional antisense RNA (as in Step 3)

Facilitating Miniaturization by Functional Integration—Amplification preferably is performed in a nano-reactor using an isothermal method, such as one of the variety of Transcription Amplification Systems (TAS) producing exponential amplification, or In-vitro Transcription (IVT) producing linear amplification. The starting genetic material could be DNA or RNA templates, which may or may not have a T7 promoter sequence flanking the target sequence of interest. In case of using templates without the T7 promoter, the promoter sequence can be introduced in -a single pass "copy" step using DNA and/or RNA polymerase, analogous to the "labeling step." In addition, the T7 promoter sequence can also be treated as an adapter, which can be linked to a template of interest by using ligase. Incorporation of T7 promoter into the target of interest is performed as part of template preparation.

2.1—Strand Selection and Linear Amplification by Way of In-Vitro Transcription

One aspect of eMAP protocols as previously disclosed (see eMAP application), is the step of strand selection, generally guided by certain design considerations (see eMAP, HMAP application, Ser. No. 10/847,046). One method of selecting a specific strand from a PCR amplicon is that of digesting a phosphorylated strand using an exonuclease, leaving the undigested strand for on-chip analysis of polymorphisms or mutations by way of DNA polymerase catalyzed elongation of allele-specific probes (see eMAP app).

An alternative to that method of strand selection is the application of IVT to produce either sense RNA or anti-sense RNA, as directed by the incorporation of a T7 (or other promoter) sequence into the PCR product. This method accommodates the design rules for strand selection previously disclosed (hMAP application) but requires detection and allele analysis of the resulting product by elongation of allele-specific RT primers, preferably displayed on color-encoded microparticles, as illustrated in Examples and figures provided herein.

The advantages of applying IVT as a method strand selection include the following:
- protocol simplification: only a single enzyme, namely an RNA polymerase, is required, with minimal post-PCR "clean-up" (see Section 2.1, below);
- the additional (asymmetric) amplification of RNA product reduces the requisite number of PCR cycles required to produce a desired amount of detectable target;
- combinations of nested PCR and IVT permit allele-discrimination to be incorporated into steps other than the last step, namely allele-specific probe elongation, thereby providing greater design flexibility (see also Example VI below)
- IVT and on-bead RT-mediated probe elongation can be combined in concurrent formats, notably permitting multiplexed linear amplification and product analysis to be performed on chip, as disclosed herein (see Section 2.2)—this functional integration in turn permits miniaturization by means of the methods described in Section 1

In an IVT-RT-eMAP assay, performed subsequent to, or concurrently with IVT-mediated target amplification, as described in detail below, an RNA is captured to a complementary RT primer, and the primer is elongated by way of reverse transcription (RT) using the captured RNA as a template for on-bead cDNA synthesis (see FIG. 6). In a preferred embodiment, sequence-specific RT primers are encoded by attaching them to color-coded microparticles ("beads").

Elongation products formed on beads, can be labeled by incorporation of labeled dNTPs (or ddNTPs) or rNTPs during elongation. Alternatively, elongation products can be labeled following elongation and removal of the RNA template, by capture of labeled olignucleotide probe directed to a downstream portion of the elongation product (see "phasing," described in eMAP Application). In one embodiment, this probe is a looped probe, generating signal only when annealed to the elongation product (see also U.S. Provisional Application No. 60/628,464, incorporated by reference). The latter embodiment is well-suited for real-time monitoring of the reaction. Labeled elongation products are detected with known methods, including READ™, as described in U.S. Ser. No. 10/032,657 and U.S. Pat. No. 6,797,524 (incorporated by reference), wherein the assay can be carried out on a solid surface, e.g., a BeadChip™ (see FIG. 3 for an illustration of detection using a looped probe).

2.1.1 Strand Selection by "In-Tube" IVT, Followed by "On-Chip" RT-eMAP

Following PCR, performed with T7-tagged reverse (or forward) primers, IVT reaction mix, and RT-eMAP reaction mix are prepared in separate test tubes, and the product of the IVT reaction is added to the RT-eMAP mix. That is, IVT, preferably using T7 RNA polymerase, is carried out first, by incubating an aliquot of the reaction mix in a test tube or on a BeadChip, and incubating at 37° C. for 30 minutes. Next, the RT-eMAP reaction, preferably using SuperScript III reverse transcriptase, is carried out by adding the RT-eMAP reaction mix to the IVT product, either in-tube or on-chip, and incubating at 50° C. for another 30 min. No washing or buffer exchange steps are required. The selected temperatures reflect optimal operating conditions for the two enzymes. In one embodiment of the protocol, the RT-eMAP reaction is carried out using M-MLV reverse transcriptase, thus permitting isothermal operation, at 37° C.

Figure 7:
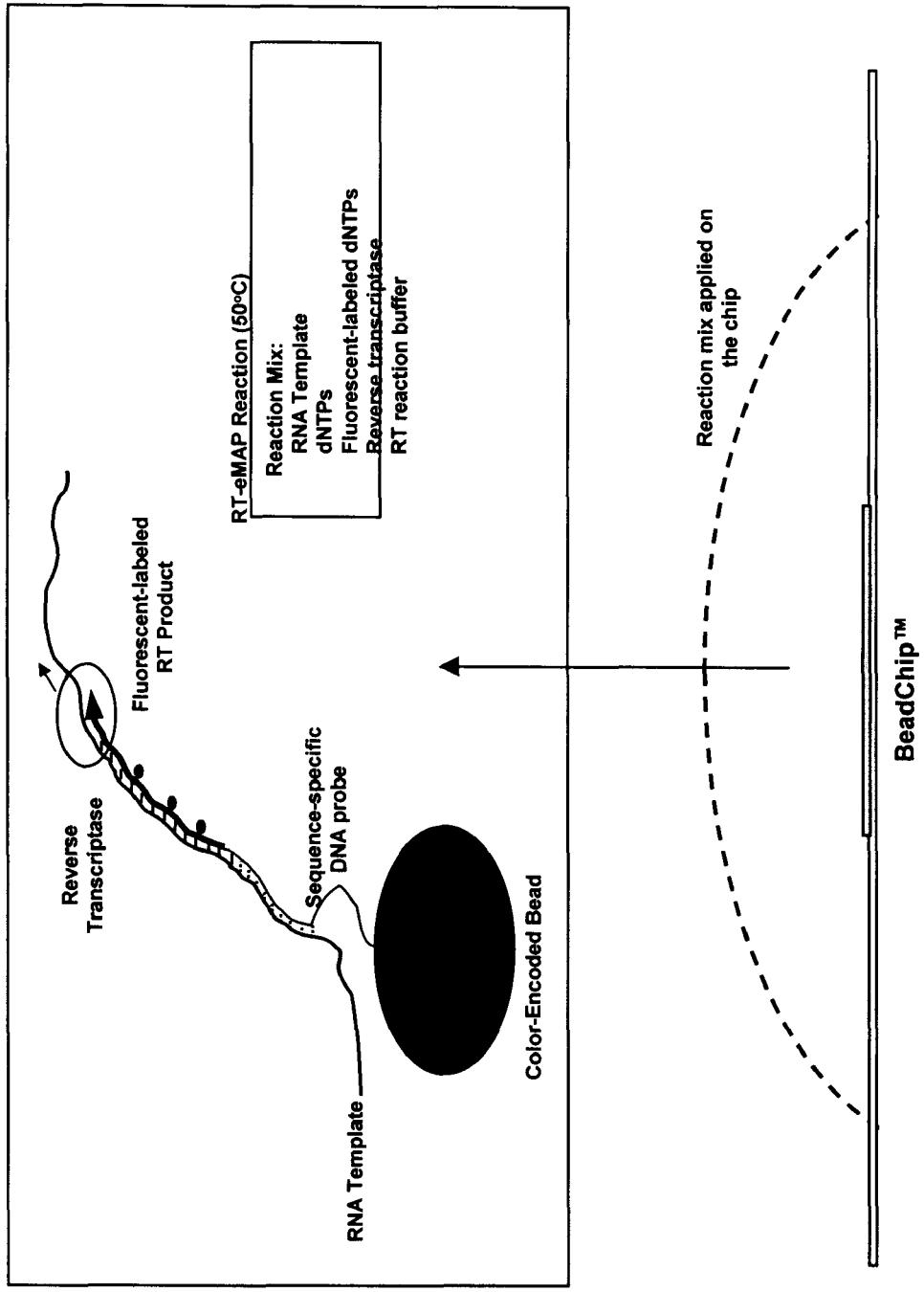
FIG. 7 depicts a one-step RT-eMAP assay, with eMAP carried out on a bead using a sequence-specific DNA probe, as shown.
Figure 8:
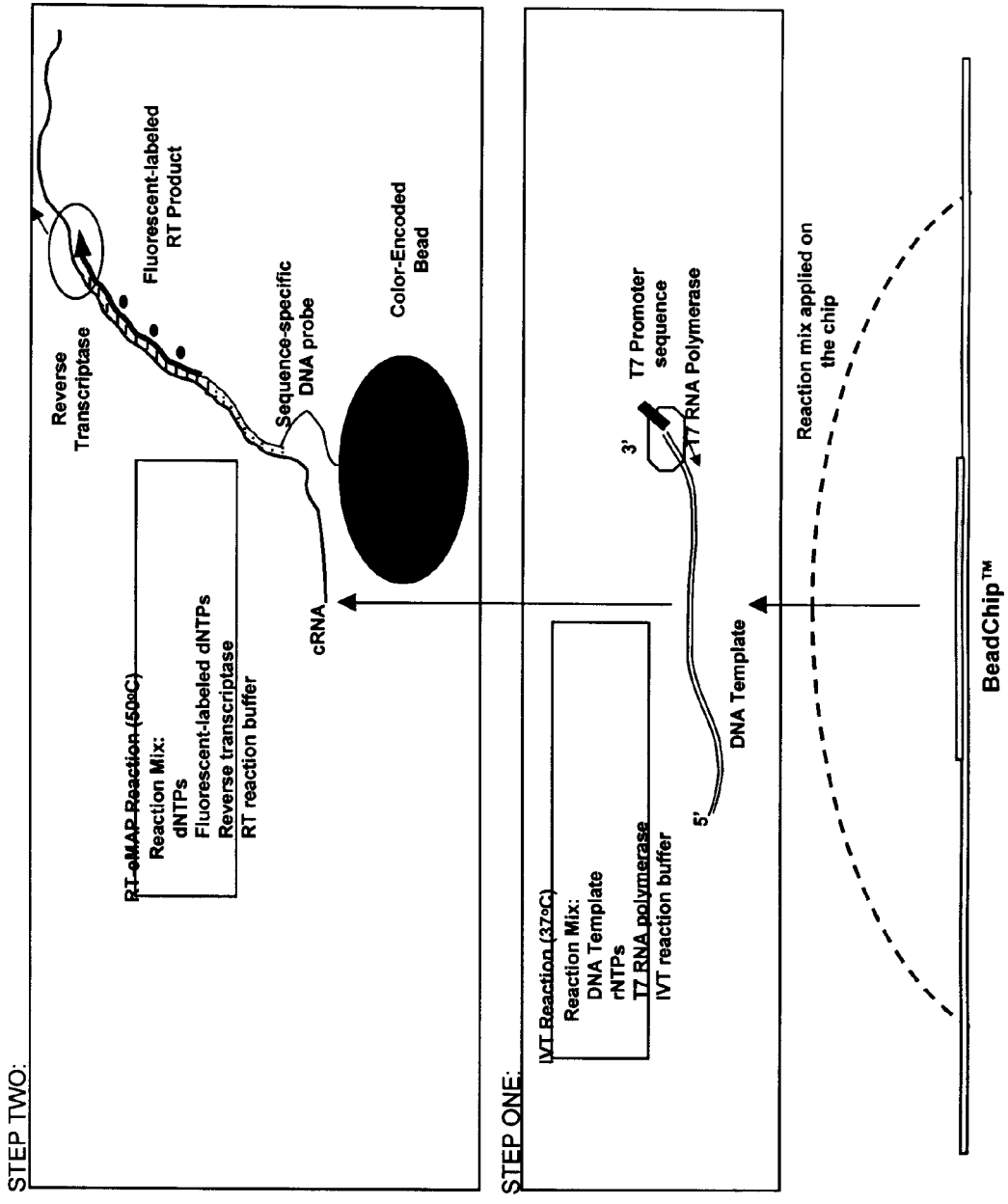
FIG. 8 depicts a two-step on-chip IVT RT-eMAP assay, where first a double-stranded DNA template is amplified with an IVT reaction, and then an RT-eMAP assay is used to quantitate the product.
Figure 9:
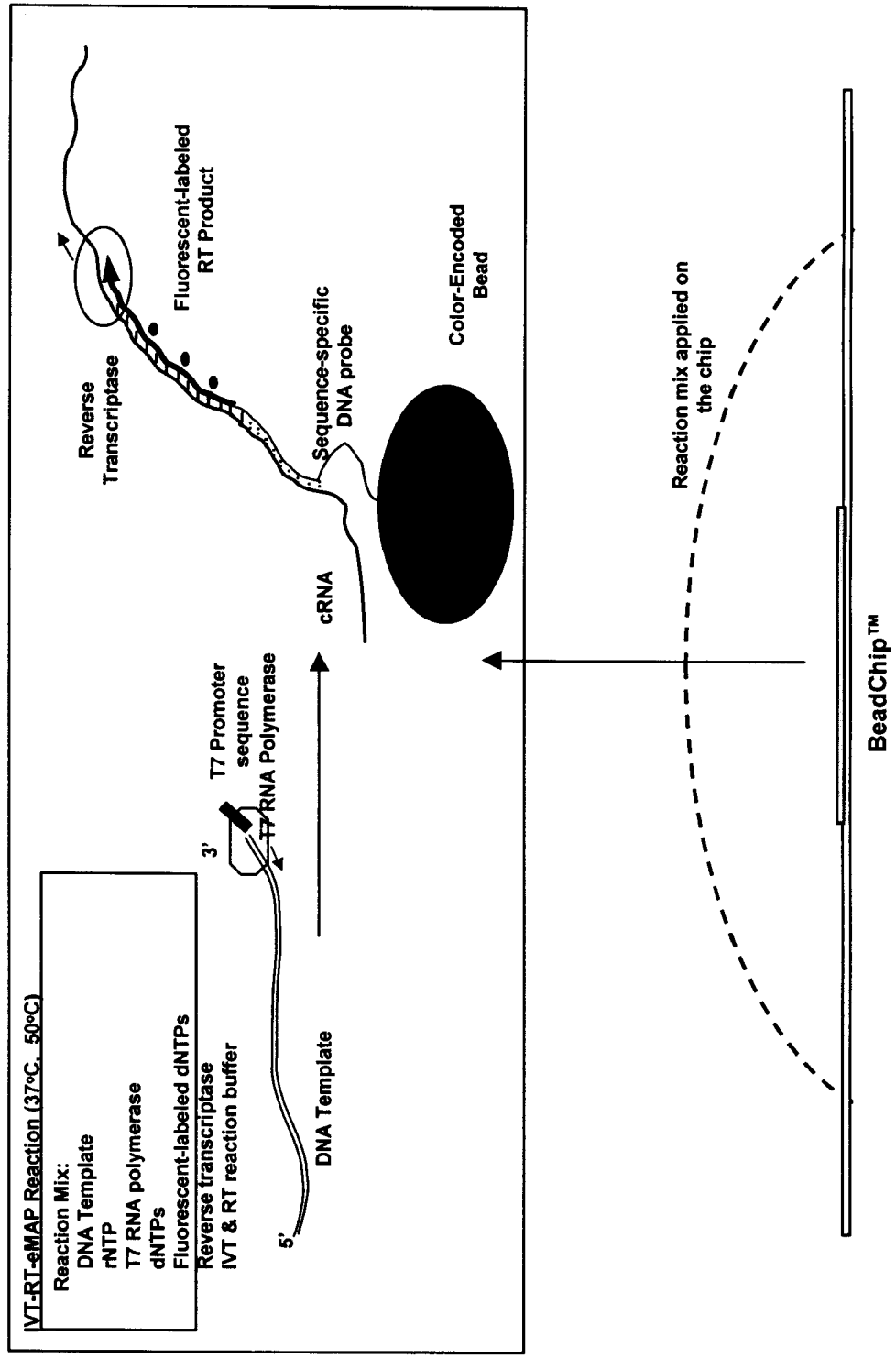
FIG. 9 depicts a depicts a homogeneous assay, i.e., a one-step on-chip IVT RT-eMAP assay, where a double-stranded DNA template is amplified with an IVT reaction, and simultaneously an RT-eMAP assay is used to quantitate the product.
Figure 10:
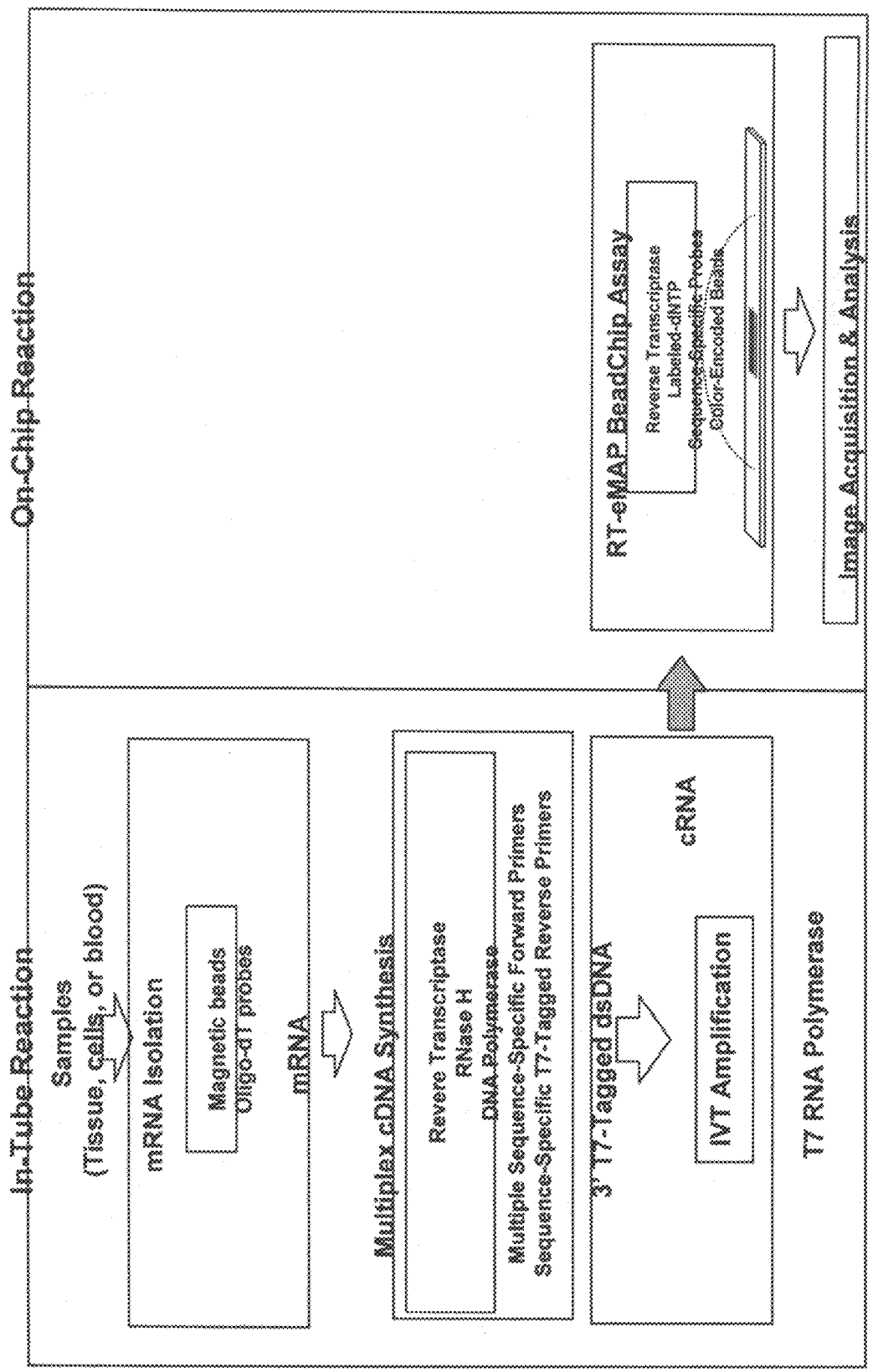
FIG. 10 depicts steps in a single tube two-step IVT RT-eMAP assay, where IVT amplification is carried out by addition of T7 RNA polymerase, following synthesis of dsDNA.
Figure 11:
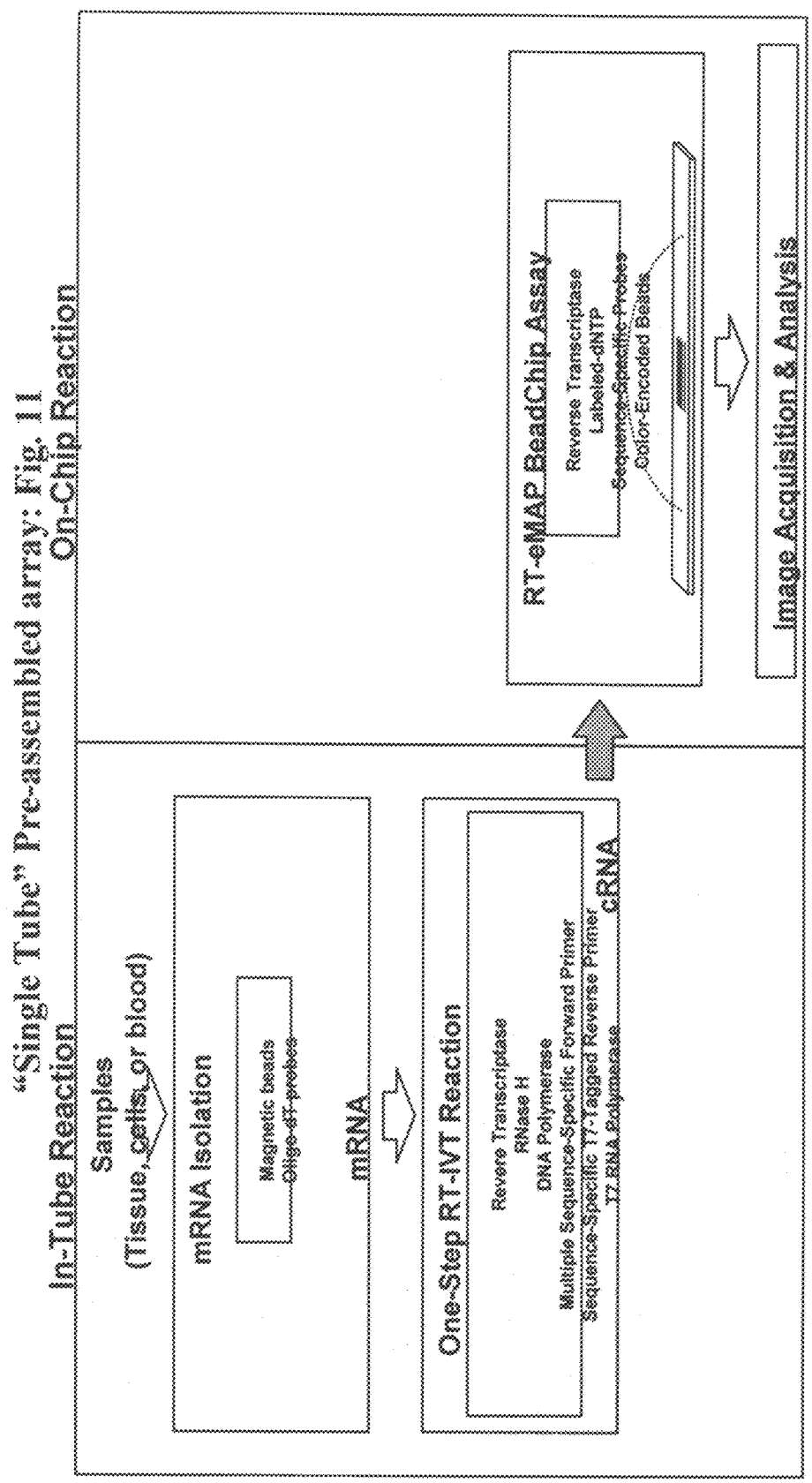
FIG. 11 depicts steps in a single tube IVT RT-eMAP assay, where IVT amplification is carried out in a single-step by including T7 RNA polymerase in the reaction mix, and then RT-eMAP is used to assay the product.
Figure 12:
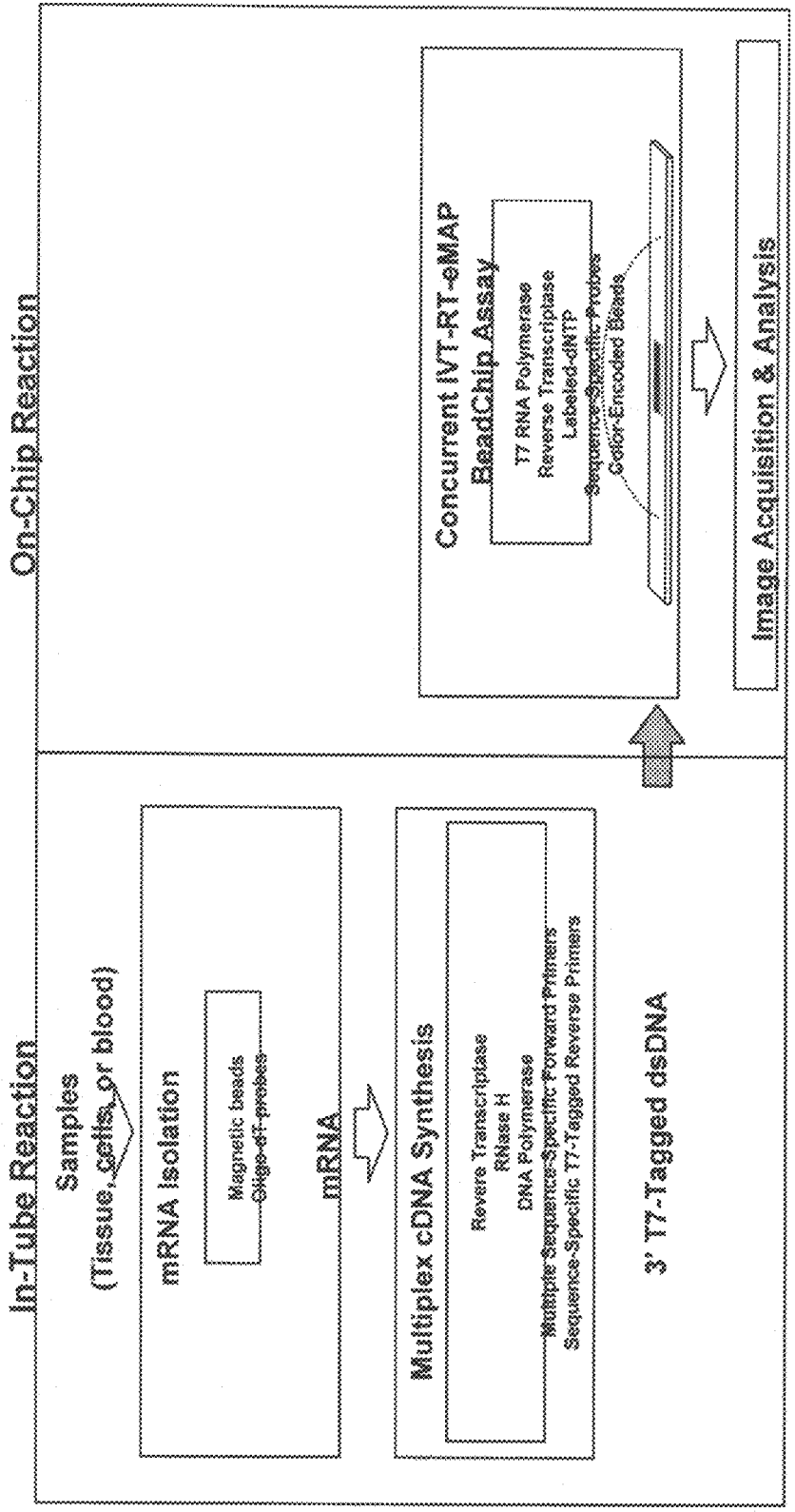
FIG. 12 depicts a homogeneous IVT RT-eMAP assay, where following generation of dsDNA, IVT amplification and eMAP are carried out concurrently.
Figure 13:
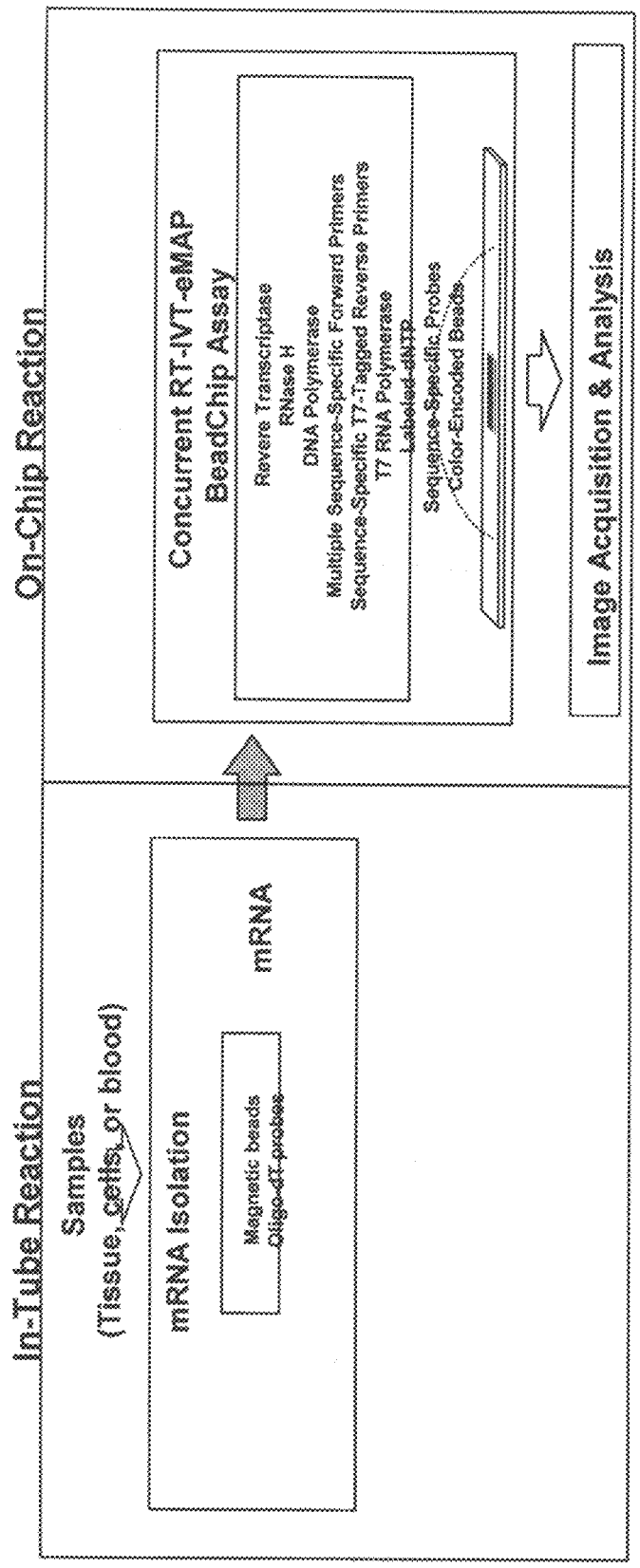
FIG. 13 depicts a homogenous single tube IVT RT-eMAP assay, where IVT amplification of RNA and eMAP are carried out concurrently.
Figure 14:
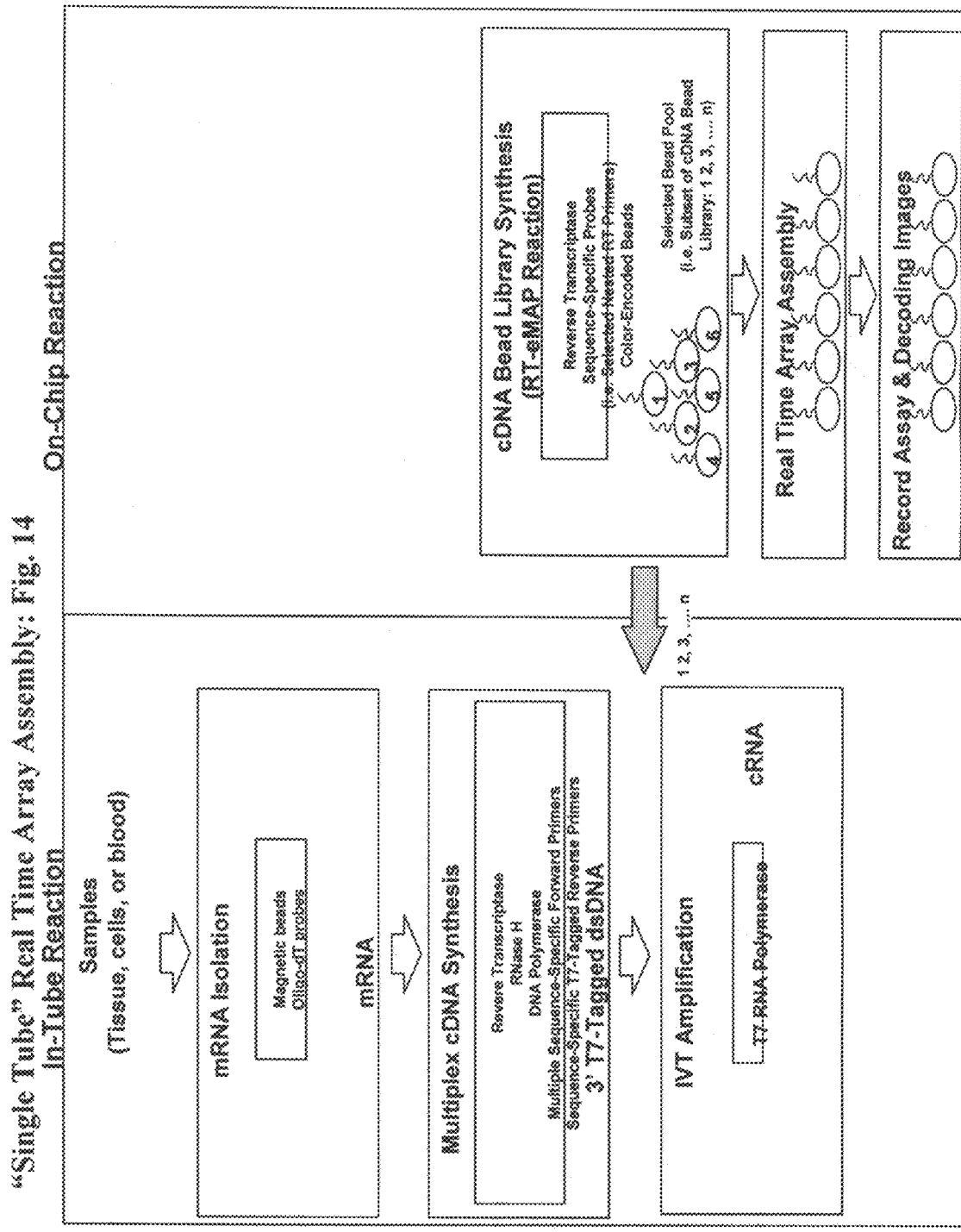
FIG. 14 depicts steps in cDNA library synthesis using RT-eMAP for synthesizing the cDNA library, following IVT amplification, and then a real time array assembly and assay using the library.
Figure 15:
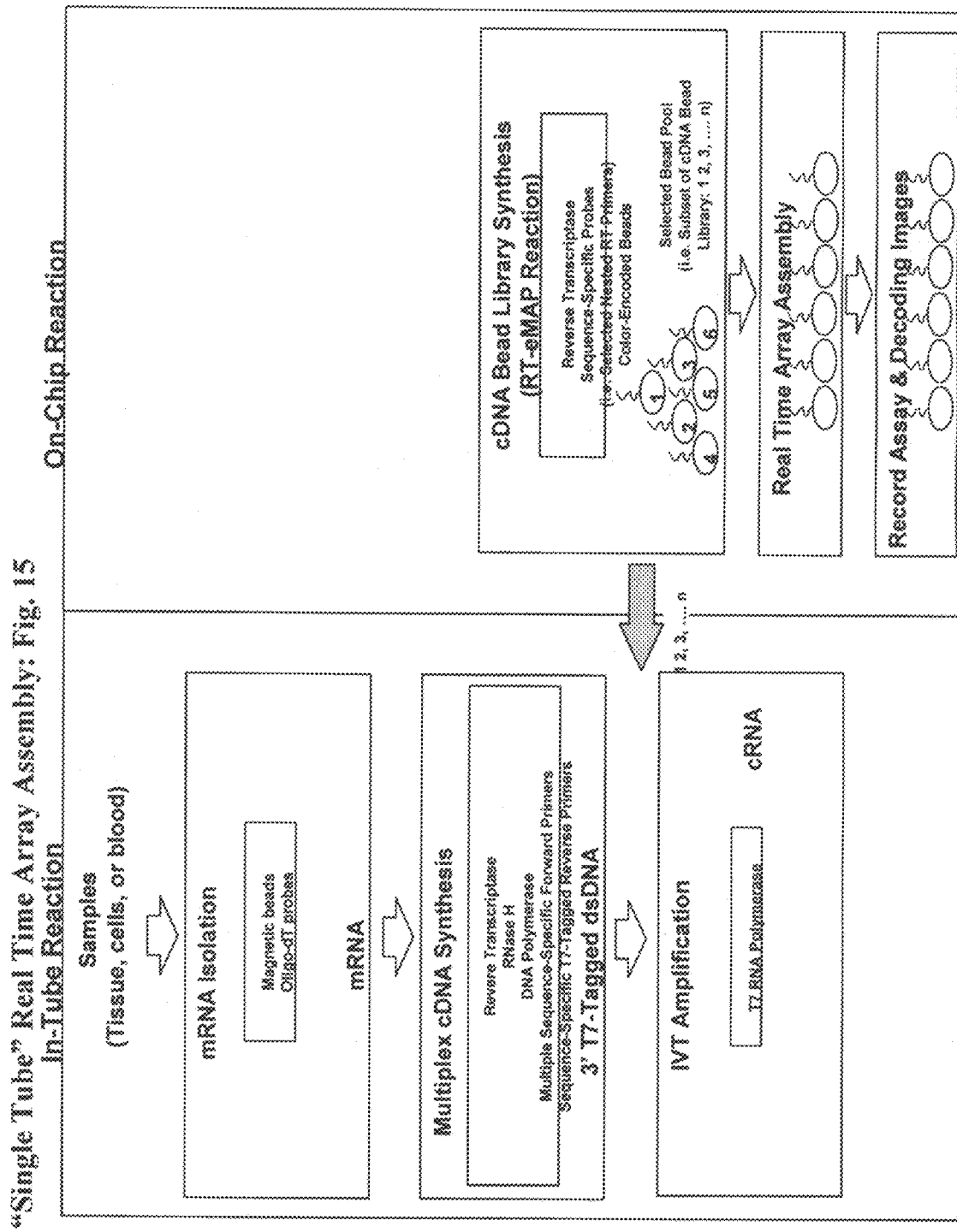
FIG. 15 depicts steps in cDNA library synthesis using RT-eMAP for synthesizing the cDNA library, following IVT amplification, and then a real time array assembly and assay using the library.
Figure 16:
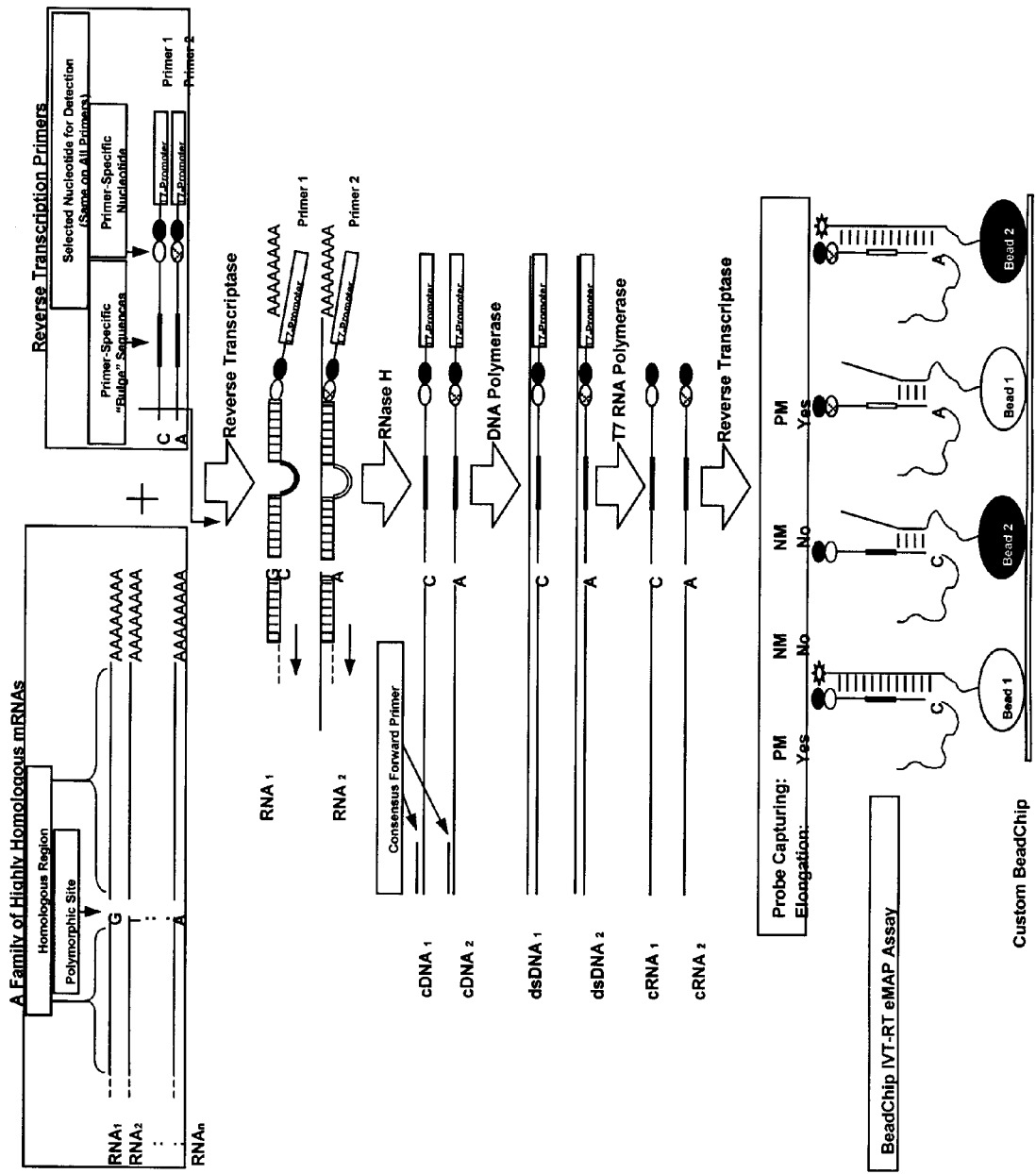
FIG. 16 depicts using an IVT RT-eMAP assay for discrimination among highly homologous mRNAs.

Details of the formats of combining IVT and RT-eMAP for multianalyte molecular analysis are described in Example I for the case of analyzing designated polymorphic sites within the highly variable human HLA-DQ locus. A multiplexed RT-eMAP assay was performed, on a pre-assembled custom bead array ("BeadChip™"), composed of color-encoded beads displaying RT primers directed to specific subsequences of the RNA target of interest (see FIGS. 7 & 9; FIG. 8 illustrating a two-step, two temperature protocol), in accordance with the protocol described above, namely, on-chip RT at 50° C. using an RNA template formed in a separate IVT reaction.

2.1.2 Allele-Specific Strand Selection: IVT Following Nested PCR Amplification

Figure 42:
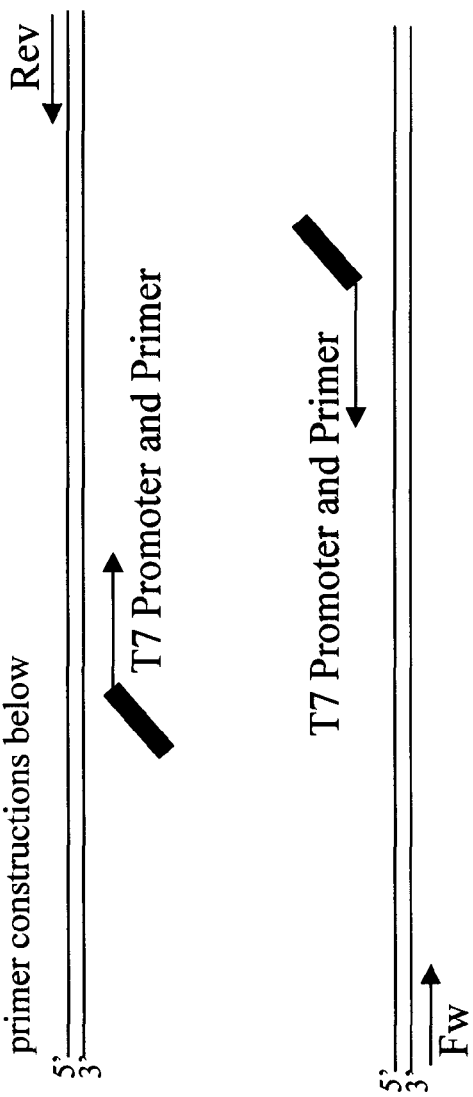
FIG. 42 depicts the steps in selecting one strand from double-stranded DNA using PCR and an IVT reaction.

Also disclosed is a method of allele-specific strand selection mediated with IVT. The design of two allele-specific primers for nested PCR amplification containing the T7 (or other) non-template (NT) promoter strands, as shown in FIG. 42, ensures the formation of different products depending on the allele configuration encountered in a given gDNA. That is, by performing PCR amplification using a pair of primers to isolate a variable site of interest within a target sequence, and using a second pair of T7-tagged, allele-specific nested primers, nested amplicons are formed which, depending on the specific allele configuration encountered.

Each of the products, incorporating the T7 (or other) promoter sequence at either the 5' end or 3'-end, serves as a templates for a subsequent IVT reaction producing RNA strands which differ in sequence and thus can be detected in a single reaction. Example VI describes the application of this design principle to the detection of a mutation in the GATA box of the gene encoding the Duffy red blood cell antigen. (M. E. Reid and C. L. Francis, "*The Blood Group Antigen Facts Book*," Academic Press, 1996).

The entire assay, including 1 h image acquisition and analysis for 96 samples, takes only 4 h 30 min, and includes just 2 enzymatic reactions, namely PCR and IVT. The elimination of purification steps makes this protocol particularly well suited for functional assay integration.

2.2 "Coupled" IVT, RT-eMAP Reactions:

TABLE I

| PROTOCOL/ FORMAT | "Coupled" IVT-RTeMAP |
|---|---|
| 2-Step | Sequential ("single tube") |
| "" | IVT @ 37° C., then RT-eMAP @ 50° C. |
| 1-Step | Concurrent ("homogeneous") Isothermal |

Formats of Combining IVT and RT-eMAP—The IVT-RT-eMAP assay can be performed in two different formats, representing increasing degrees of integration, as described in greater detail herein, and as illustrated in FIGS. 10-15, in Example I, and in Table I.

2.2.1 Sequential ("2-Step") Version—Aliquots of IVT and RT-eMAP reaction mixes, containing T7 polymerase and a reverse transcriptase, e.g., Superscript III reverse transcriptase, respectively, are combined, either in-tube or on-chip. The IVT reaction is initiated by incubating at 37° C., following which the RT is initiated by ramping the temperature to 50° C. No washing or buffer exchange steps are required.

2.2.2 Concurrent ("1-Step") Version—Aliquots of IVT and RT-eMAP reaction mixes, containing T7 polymerase and an enzyme with RNAseH activity, e.g., M-MLV, respectively, are combined, either in-tube or on-chip, and incubated at 37° C., thus permitting both reactions to occur concurrently. No washing or buffer exchange steps are required.

Details of these two formats of combining IVT and RT-eMAP for multianalyte molecular analysis in a single reaction are described in Example I: Example I.3 describes a concurrent, 2-temperature (37° C. and 50° C.) coupled IVT-RT-eMAP format and Example I.4 describes a concurrent isothermal (at 37° C.) IVT-RT-eMAP format.

The results of Example I, illustrated in FIG. 17A for IVT-mediated strand selection followed by on-chip RTeMAP, and FIGS. 17B and 17C, respectively, for the two concurrent formats, demonstrate the viability of combining IVT and RT-eMAP for multiplex analysis. In particular, the essential equivalence of the results for the homogeneous format, e.g. those in FIG. 17C, and those of the other formats, e.g. those in FIGS. 17A and 17B, establishes the viability of functional integration of amplification and multiplex detection. Factors affecting the degree of coupling between the two relevant enzymatic reactions are described in greater detail below.

It was also shown (see Example IV) that eMAP can be used to detect and analyze an entire set of single-stranded amplification products in a reaction volume as small as 30 nl and generate results comparable to those obtained in a 10 µl volume. Examples I.3 and I.4 demonstrate the viability of performing a combination of IVT and RTeMAP in a homogeneous format, requiring no sample manipulation. This homogeneous format is suitable for miniaturization using, for example, the configuration and nanoreactor design described in Example IV for eMAP. Thus, these results demonstrate proof of concept of a nano-liter scale IVT RT-eMAP assay.

The experiments described in Example I for multiplexed detection using the IVT RT-eMAP assay, also show that although lower than that for PCR, as expected, the amplification gain for the concurrent IVT reaction was at least 100-fold, the concurrent formats producing a lower gain than the strand selection format in which IVT is performed as a separate reaction under optimal conditions.

IVT, given a sufficient amount of starting material, can generate sufficient product- for detection, provided the amplification reaction is confined to a sufficiently small volume, preferably in the range of 1 to 100 nl. A sufficient amount of starting material can always be produced by PCR.

When genomic DNA is to be used as the starting material, at a typical concentration of about $10^4$ molecules/microliter to $10^5$ molecules/microliter—and PCR it not to be employed—the target can be concentrated, by a factor of 10 to 100, into a volume of 10 to 100 nl, for example by magnetic separation, in accordance with methods of the art. Once confined to such a volume, the subsequent IVT reaction (following conversion to an T7-tagged copies of the target sequences of interest) will produce an RNA concentration in the range of nanomolar that is readily detectable by RTeMAP.

Alternatively, if mRNA is the starting material for the IVT reaction, concentration of of mRNA by magnetic capture, in accordance with standard methods, would permit the application of these concurrent formats of IVT and RTeMAP for quantitative expression profiling.

Figure 3:
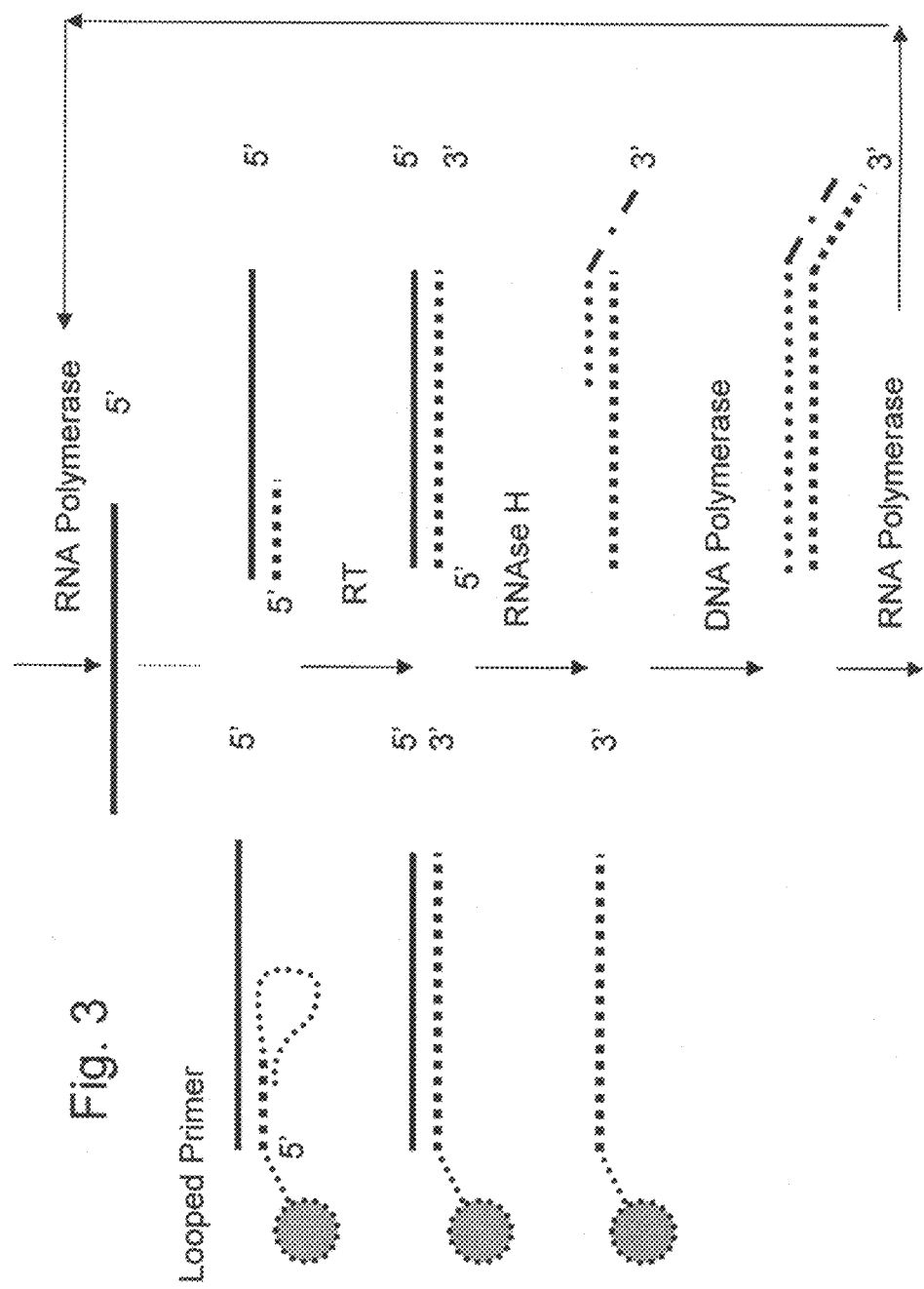
FIG. 3 depicts coupling of exponential amplification of RNA with the IVT method with detection by on-bead capture and elongation using a looped primer.

A Homogeneous format of TAS and Multiplexed Analysis—Also disclosed are assay compositions relating to a homogeneous format of exponential amplification—by one of the known versions of a TAS—and detection and analysis (for variable sites) of RNA products generated in such a reaction on encoded microparticles ("beads") using bead-displayed capture probes, preferably capture probes having a "looped" configuration. The signal intensity from the "open" configuration of looped probes can be used to determine the amount of antisense RNAs generated in the reaction mix. As shown in FIG. 3, when invoking TAS, in the presence of bead-displayed looped probes having a portion of the sequence identical to the forward primer (Step 2, FIGS. 1 & 2), a portion of the antisense RNA (formed in Step 3) can anneal to such a looped probe in a homogeneous detection format (wherein no additional materials need to be added to the initial reaction mixture).

This format permits the rapid and safe detection of infectious agents, including especially retroviral agents, in a format that is suitable for real-time monitoring, by recording signal intensities associated with captured RNA and the "open" configuration of the looped probe(s). Multiple such probes on encoded beads can be employed in this format to permit the analysis of an RNA product at multiple (variable) sites of interest, or to detect multiple RNA products. Infectious agents of interest are listed in Table II.

TABLE II

| DNA Viruses | RNA Viruses |
|---|---|
| Adenovirus | Rhinovirus |
| Epstein-Barr Virus | Respiratory Syncytial Virus |
| Hepatitis virus, HBV | Severe Acute Respiratory Syndrome (SARS) |
| Herpes Simplex Virus | Influenza A and B |
| Bacteria | Parainfluenza Types 1, 2, 3 |
| *Streptococcus pneumoniae* | Coxsackie Virus A and B |
| *Streptococcus pyogenes* | Echovirus |

TABLE II-continued

| DNA Viruses | RNA Viruses |
|---|---|
| *Staphylococcus aureus* | Hepatitis virus, HCV |
| *Chlamydia pneumoniae* | West Nile Virus |
| *Hemophilus influenza* | HIV |
| *Mycobacterium tuberculosis* | |
| *Moraxella catarrhalis* | |
| *Coxiella burnetti* | |
| *Neisseria gonorrhoeae* | |
| *Chlamydia trachomatis* | |

EXAMPLE I

Integrating IVT and RT-eMAP in Different Formats 1.1 T7-Tagged dsDNA, IVT and RT-eMAP Complementary RNA is synthesized in a separate ("uncoupled") IVT reaction using T7 RNA polymerase and T7-tagged double-stranded DNA as a template which is in turn generated from human genomic DNA in a PCR reaction using T7-tagged reverse primer. Because the forward and reverse PCR primers are specific for exon 2 of the HLA-DQB locus, the cRNA contains the antisense sequence of the DQB locus. This provides the template for the RT-mediated elongation of degenerate oligonucleotide probes designed to act as sequence-specific RT primers which are attached to encoded beads.

Preparation of T7-tagged DNA templates for in vitro transcription—Exon 2 of the HLA-DQB1 locus was amplified in a PCR reaction using human genomic DNA as a template, a generic forward primer, and a reverse primer with a T7 promoter sequence at the 5' end (FIG. 30A). Primer sequences are available at International Histocompatibility Working Group website, chapter 2C. Sequences for the T7 and SP6 promoters are available at: Ambion, Inc.'s website Aliquots of the DQB1 PCR products were separated on 1.5% agarose gel by electrophoresis followed by ethidium bromide staining. The T7-tagged DQB1 PCR product was visualized as a ~280 bp band on the gel under UV trans-illumination (FIG. 30B) As expected, the T7-tagged DQB1 PCR product is about 20 bp longer than the untagged control (FIG. 30B). The T7-tagged PCR product was purified using MicroSpin™ G-50 Columns (Amersham Pharmacia Biotech, now called "GE Bioscience"). Concentration of the purified PCR product was determined using a UV spectrophotometer at 260 nm wavelength (FIG. 30B).

IVT Reaction—Purified T7-tagged DQB1 PCR product (FIG. 30B, lane 2) was used as a template in in vitro transcription (IVT) using T7 RNA polymerase. The in vitro transcription reaction was set up in a test tube according to the well-known protocols. Aliquots of the IVT products were separated on 5% urea-polyacrylamide gel, followed by ethidium bromide staining. The amplified DQB1 exon 2 complementary RNA (cRNA) was visualized on the gel by UV trans-illumination (FIG. 30B), in accordance with the methods described in the Fermentas Life Sciences Website. The cRNA concentration of the sample was determined to be 0.224 μg/μl using a spectrophotometer at 260 nm wavelength.

RNA to dsDNA Conversion Yield in IVT: FIG. 18 shows results of cRNA titration in RT-IVT amplification detected by gel electrophoresis. Briefly, in tubes 1-5, serially diluted cRNA was used as a template for dsDNA synthesis, using T7-tagged reverse primer and specific forward primer, and M-MLV reverse transcriptase. The RT reaction was carried out at 37° C. for 30 minutes. After incubation, aliquots (3.5 μl) of the reaction products were transferred to another set of tubes for the IVT assay. As a control for the IVT reaction, 3.5 μl of a known amount of dsDNA (48.8 ng) was transferred into tube #6. The IVT reaction mix, containing T7 RNA polymerase, rNTP and the well-known IVT reaction buffer, was then added into all 6 tubes, followed by incubation at 37° C. for 30 minutes. The DNA template (Tube #6) and the intermediate DNA products (Tubes 1-5) were removed by DNase treatment (37° C., 15 min) before analysis of the amplified IVT products (i.e. cRNA) by electrophoresis on 5% Urea-Polyacrylamide Gel (FIG. 18). FIG. 18 shows the intensities of lanes indicating different abundance of RNA generated from the IVT reaction. Assuming a yield of close to 100% for the synthesis of dsDNA from RNA templates, one would expect the amount of dsDNA in tubes #1-#5 to vary from 78.4 down to 4.9 ng, considering a conversion factor of ~7 for the same nucleotide length (mass ration of dsDNA/ssRNA ~2 of same length) in a 3.5-μl volume. In fact, in lane #6, 48.8 ng dsDNA template, produced an amount of RNA with an intensity between those of tube #1 (78.4-ng expected dsDNA) and tube #2 (39.2-ng expected. dsDNA). This confirms a 1:1 conversion yield of RNA to dsDNA by DNA synthesis in the IVT reaction.

Figure 20:
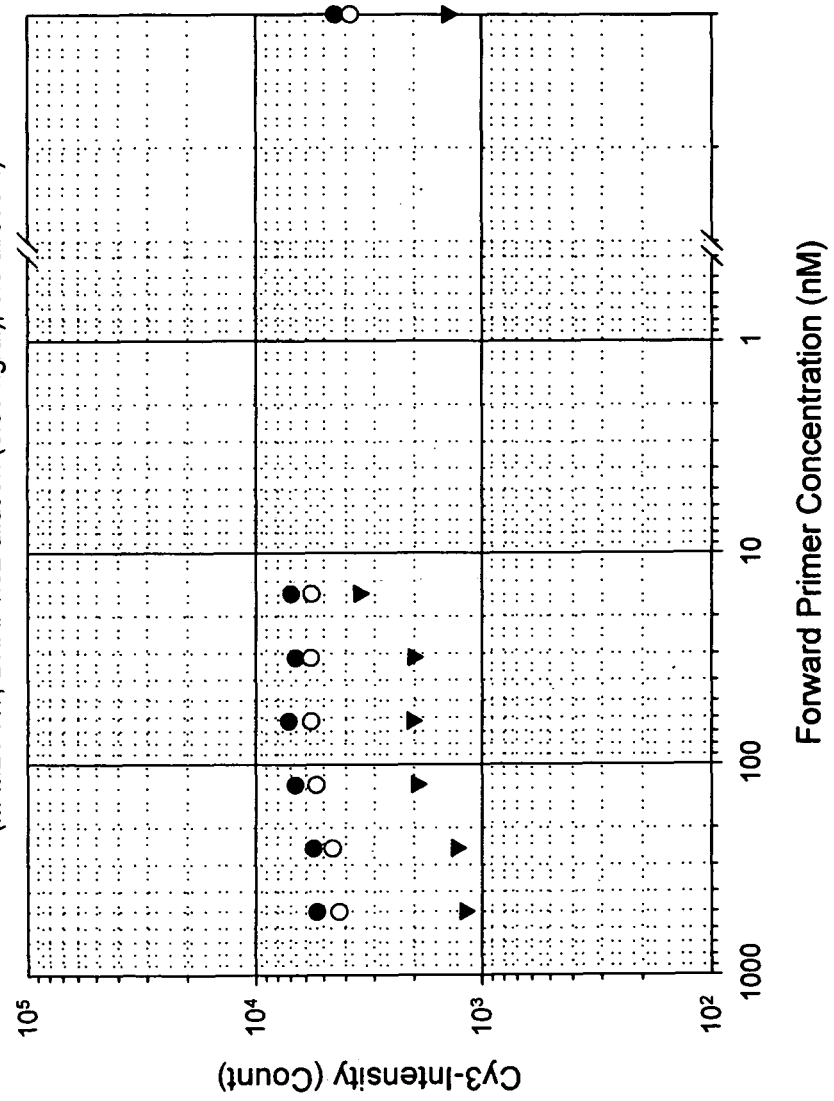
FIG. 20 shows results from a one-step on-chip IVT-RT-eMAP assay with 3 different probes, and a decreasing concentration of the forward reaction primer. The Y axis represents the quantity of RNA detected.

RT-eMAP—The purified RNA template was first serially diluted, at 1:2 ratios, with RNase-free $H_2O$ containing 1:4 diluted RNase inhibitors (Invitrogen) in 7 test tubes, 2 μl in each. The $8^{th}$ tube is a negative control, containing only RNase-free $H_2O$ without target. The serially diluted target solutions were first incubated at 65° C. for 15 minutes for denaturing the secondary structure of RNA molecules, followed by chilling on ice for 1 min. An aliquot (18 μl each) of the targets was mixed with 2 μl master mix containing 0.1 M DTT, RNase inhibitors, SuperScript III (SS-III) reverse transcriptase (Invitrogen), 10 μM dGTP, DATP, and dTTP, 10 μM Cy3-dCTP. Reaction mixes were then transferred onto HLA-DQ BeadChips from their corresponding tubes, followed by incubation at 50° C. for 30 minutes under conditions of saturated atmosphere (100% relative humidity, realized in a humidity chamber). After washing the chips with dd$H_2O$ at room temperature, chips were dried and imaged by using a fluorescence microscope. FIG. 20 illustrates the intensity of Cy3 fluorescence produced by RT-mediated elongation of RT primers, reflecting the concentration of RNA targets for probes 3, 10, and 21 of the HLA-DQ panel. For each probe, the fluorescence intensity of probes was background-corrected by subtracting a signal associated with a negative control probe included in the assay. The dose response shows linearity throughout a 2 log dynamic range from 20 ng/μl down to 0.3 ng/μl of target concentration.

Figure 23:
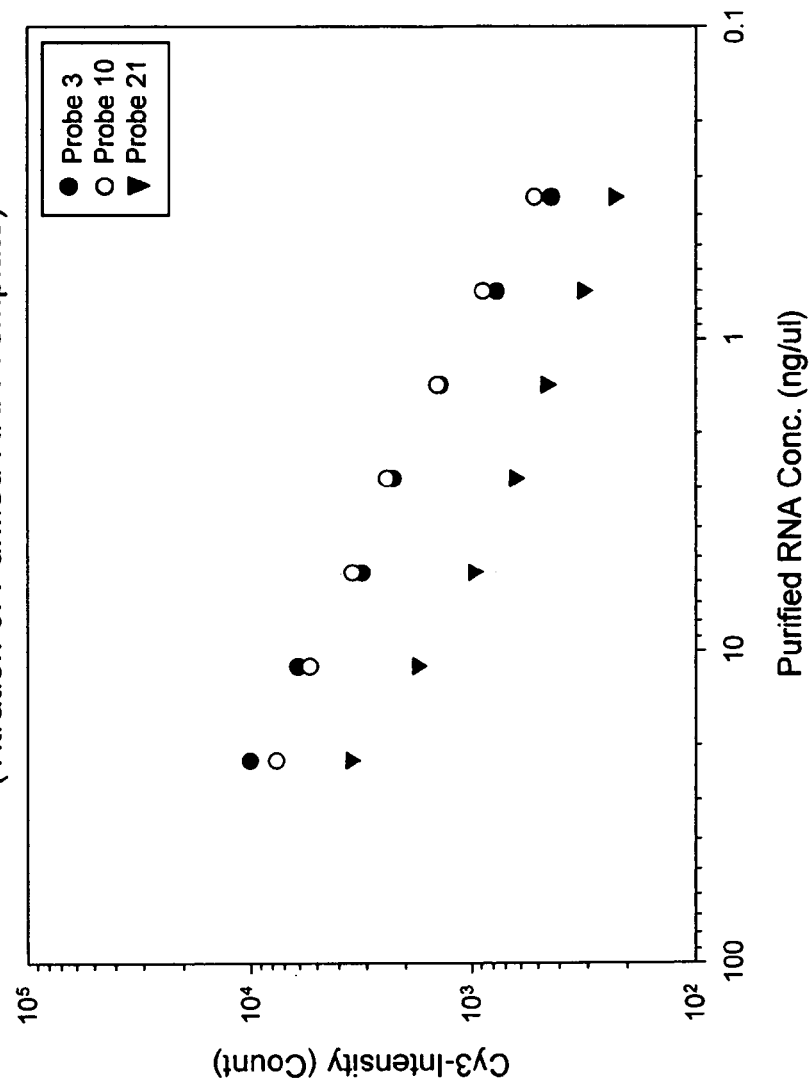
FIG. 23 shows results from a one step RT-eMAP assay with 3 probes, where the X axis shows the purified RNA concentration template for the assay in decreasing concentration.
Figure 25:
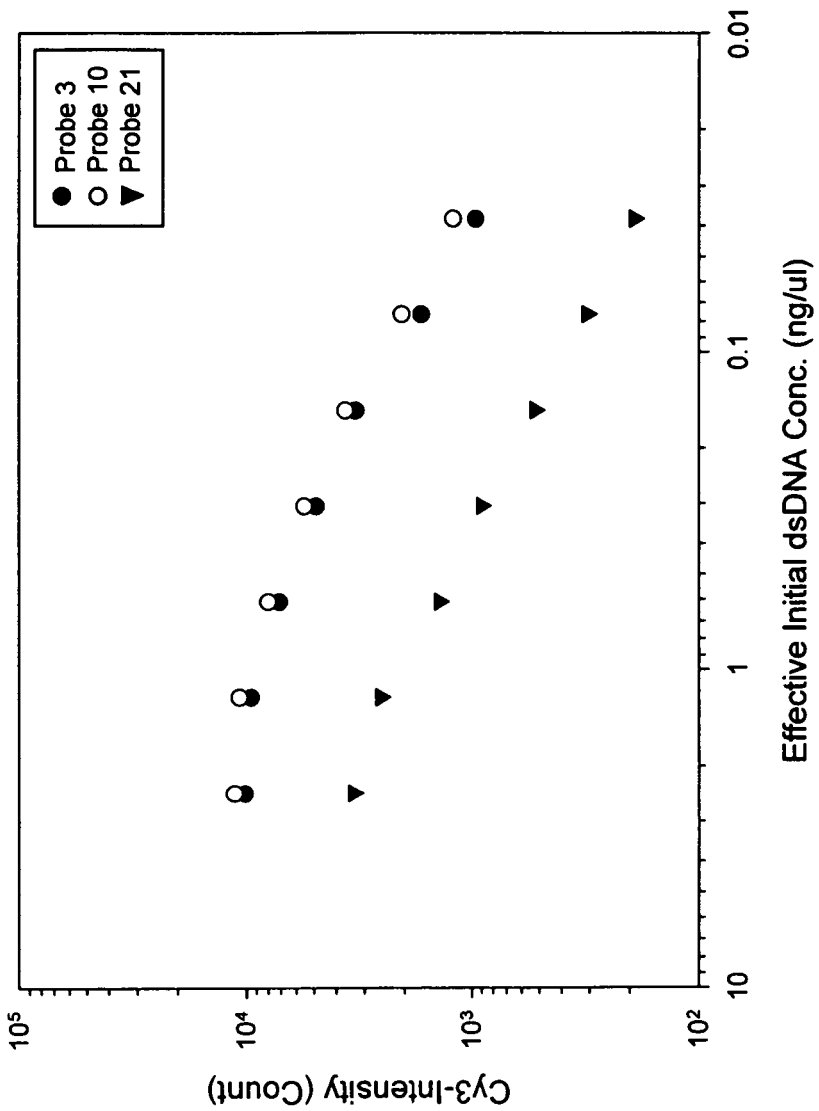
FIG. 25 shows results from a two-step reaction, with IVT and RT-eMAP carried out separately, and dsDNA is the starting material for generating an amplified RNA template for the RT-eMAP assay.

Effect of Fluorescent Dye—In a separate experiment, Cy3-dCTP was replaced by CyS-DCTP, at the same concentration—with and all other conditions the same, similar but somewhat lower sensitivity was attained. The weaker fluorescence signal intensity for Cy5 (FIG. 25) labeling relative to that for Cy3 (FIG. 23) labeling may reflect the lower quantum yield of Cy5, and/or a lower efficiency of Cy5-dCTP incorporation into the elongation products. In another separate experiment, Cy3-dCTP was replaced by TAMRA-dCTP, at the same concentration—with all other conditions the same, signal intensities are substantially lower than those observed when using Cy3-dCTP. The fluorescence signal intensities observed when using the three different dyes are shown as a function of RNA template concentration in FIGS. 26-29.

Figure 24:
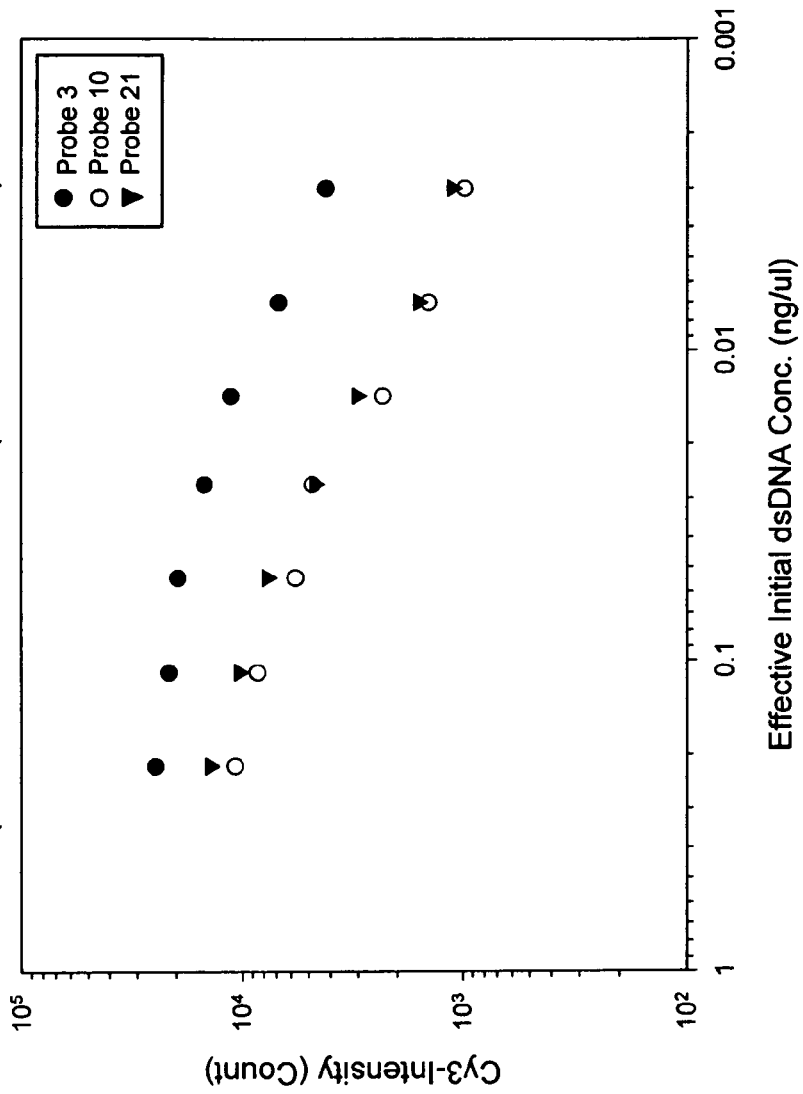
FIG. 24 shows results from a one step RT-eMAP assay with 3 probes.

1.2 Strand Selection by IVT, followed by RT-eMAP—This assay was carried out by first completing the in vitro transcription (IVT) reaction in tube using purified double stranded DNA (dsDNA; see 1.1) and then mixing an aliquot taken from the tube with reverse transcriptase enzyme buffer to proceed with the RT-eMAP reaction on a BeadChip. In this experiment, the concentration of PCR product (dsDNA) was 0.0975 μg/μl, as determined by UVNIS absorption spectrophotometry at 260 nm wavelength. An eightfold serial 1:2 dilution of the DNA template was first carried out in 8 test tubes, and aliquots (7.5-μl) of the diluted PCR product were transferred into a set of 8 fresh test tubes, each containing 12.5-μl reaction mix, i.e. T7 polymerase mix, and RNase inhibitors (Promega). The tubes were mixed by vortexing, and then incubated at 37° C. for 30 minutes for the transcription reaction. After incubation, the reaction mix was incubated at 65° C. for 15 minutes, mixed with RT-eMAP reaction mix, and transferred to carry out the RT-eMAP reaction as described above. The Cy3 intensity as a function of the initial dsDNA concentrations, plotted in FIG. 24, shows a clear dose response. The titration curves of Cy3 vs. the dsDNA template is shown in FIG. 29, which have a similar shape compared to those shown in FIG. 24, but the overall Cy3 signal is about a factor of 4 lower.

1.3 Two-step Sequence of "on-chip" IVT and RT-eMAP, using Two Temperatures—This assay was carried out by first completing the IVT reaction on a BeadChip using purified dsDNA as a template and then adding SuperScript III (SSIII) reverse transcriptase with buffer into the mixture to proceed with RT-eMAP reaction on the same chip surface. Two incubation temperatures were used, namely, 37° C. in IVT step, and 50° C. in RT-eMAP elongation step, reflecting preferred temperatures for the enzymes catalyzing the two steps, namely T7 polymerase and SSIII reverse transcriptase. In this experiment, human DQ PCR product was used as the DNA template. The dsDNA was first serially 1:2 diluted in 8 test tubes in H$_2$O starting with 97.5 ng/μl in the first tube. Then, 1-μl aliquot of the diluted DNA was mixed with a 9-μl IVT reaction mix (containing T7 polymerase mix and RNase inhibitors from Promega). The resulting 10-μl IVT reaction mix was transferred onto the BeadChips, followed by incubation at 37° C. for 30 min under humidity control, in a saturated atmosphere (100% relative humidity). After incubation, 10-μl RT-eMAP reaction mix, containing 5× reaction buffer, 0.1 M DTT, RNase inhibitors, SuperScript III reverse transcriptase, 10 μM dATP, dGTP, and dTTP, and 10 μM Cy3-dCTP, was added to the IVT mix on the BeadChip. Then, the chips were incubated at 50° C. for 30 min in the humidity chamber. Optimal reaction temperature for SuperScript III reverse transcriptase is 50° C., as indicated by the manufacturer (i.e. Invitrogen). After incubation, the chips were washed and dried for image acquisition by using a fluorescence microscope. For all of the three positive probes of the HLA-DQ panel, the Cy3 intensity as a function of initial dsDNA concentration displays a clear dose response (FIG. 29).

Figure 26:
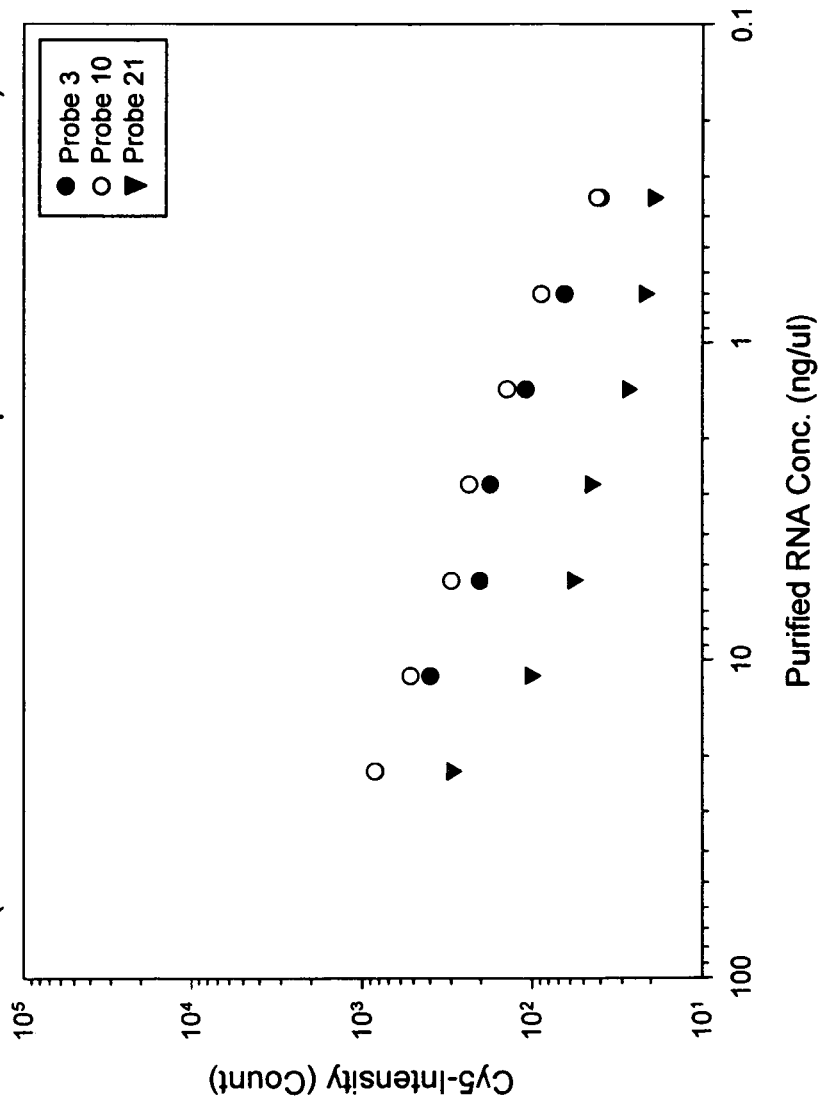
FIG. 26 shows results from a one step IVT-RT-eMAP assay with 3 probes, where dsDNA is the starting material for generating an amplified RNA template for the RT-eMAP assay, with Cy5 labeled dNTP.

1.4 Concurrent Isothermal IVT-RT-eMAP—This assay was carried out using Moloney Murine Leukemia Virus (M-MLV) reverse transcriptase. Unlike SuperScript III reverse transcriptase, M-MLV reverse transcriptase has an optimal reaction temperature of 37° C., identical to the optimal temperature for RNA polymerase in the IVT reaction. In this case, all reagents—including dsDNA templates, M-MLV reverse transcriptase, T7 RNA polymerase, and components for IVT and RT-eMAP reactions (described above)—were premixed and the reaction mix was placed in contact with a BeadChip. On-bead RT-mediated elongation thus occurred concurrently with the in vitro transcription, during incubation carried out for 30 min at 37° C. in a humidity chamber. After incubation, the chips were processed and imaged as described above. The results for one such assay are shown in FIG. 26.

Figure 19:
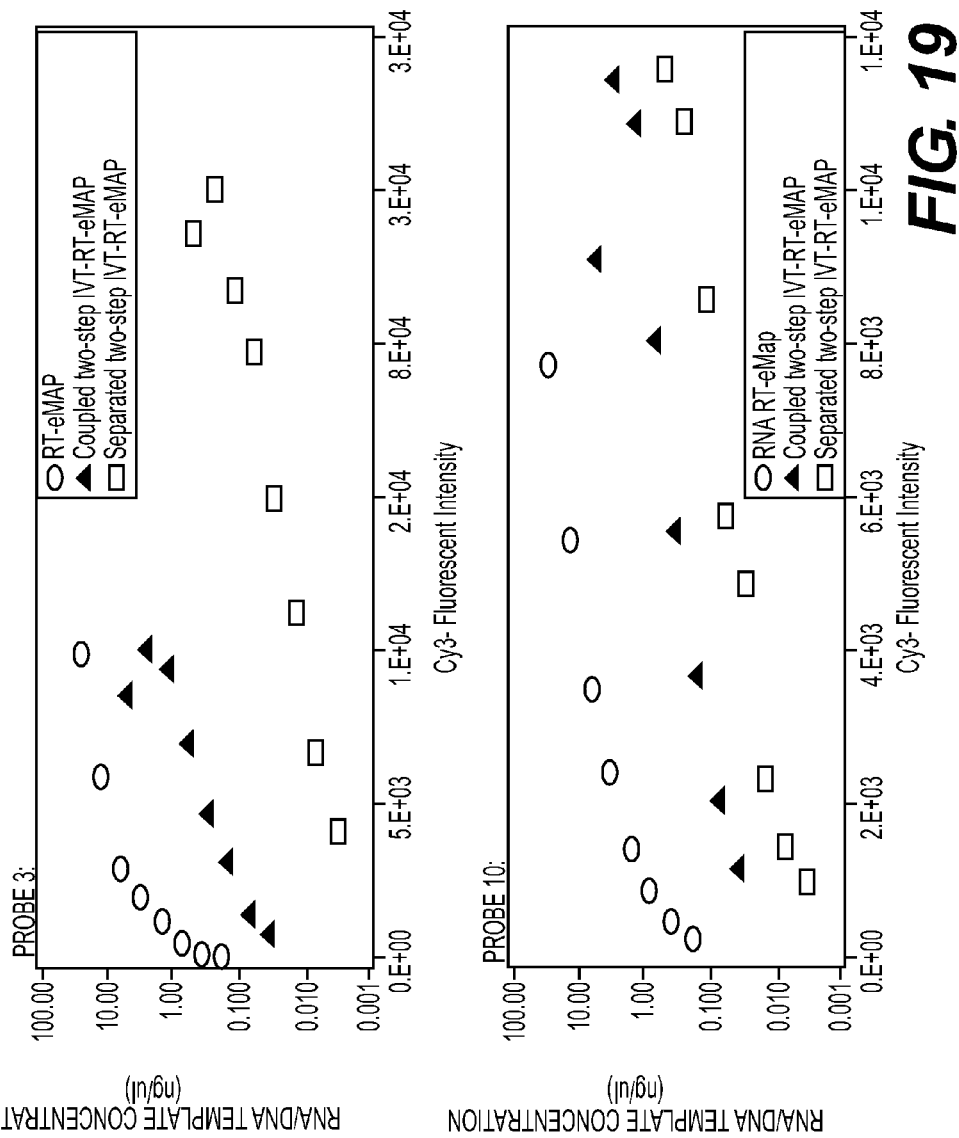
FIG. 19 shows a comparison of different assay formats of an on-chip multiplex RT-eMAP assay, including RNA-RT-eMAP and coupled and separated IVT RT-eMAP.

IVT Amplification Gain—The degree of amplification ("gain") attained in IVT can be derived by plotting initial dsDNA concentration against the Cy3 signal for uncoupled and coupled IVT and RT-eMAP assays on the same chart. FIGS. 19A and 19B shows such plots for two different sequence-specific probes (probe 3 and 10, as shown in FIGS. 17A-17C). Each plot contains signals generated in three experiments, namely, the RT-eMAP assay using purified RNA as template, the two-step (uncoupled) IVT-RT-eMAP assay, and the one-step (coupled) IVT-RT-eMAP assay. By comparing initial concentration at extrapolated intercepts of the linear portion (>3000 count on abscissa) on the ordinate, the amplification gain in IVT can be estimated as follows (Table II):

TABLE II

| Probe | Coupled | Decoupled |
|-------|---------|-----------|
| #3    | 48      | 3379      |
| #10   | 76      | 477       |

Thus, the one-step coupled IVT-RT-eMAP reaction produced a smaller amplification gain compared to the decoupled reaction. It is believed that the gain in both reactions can be improved by optimization of the respective buffer compositions.

Figure 27:
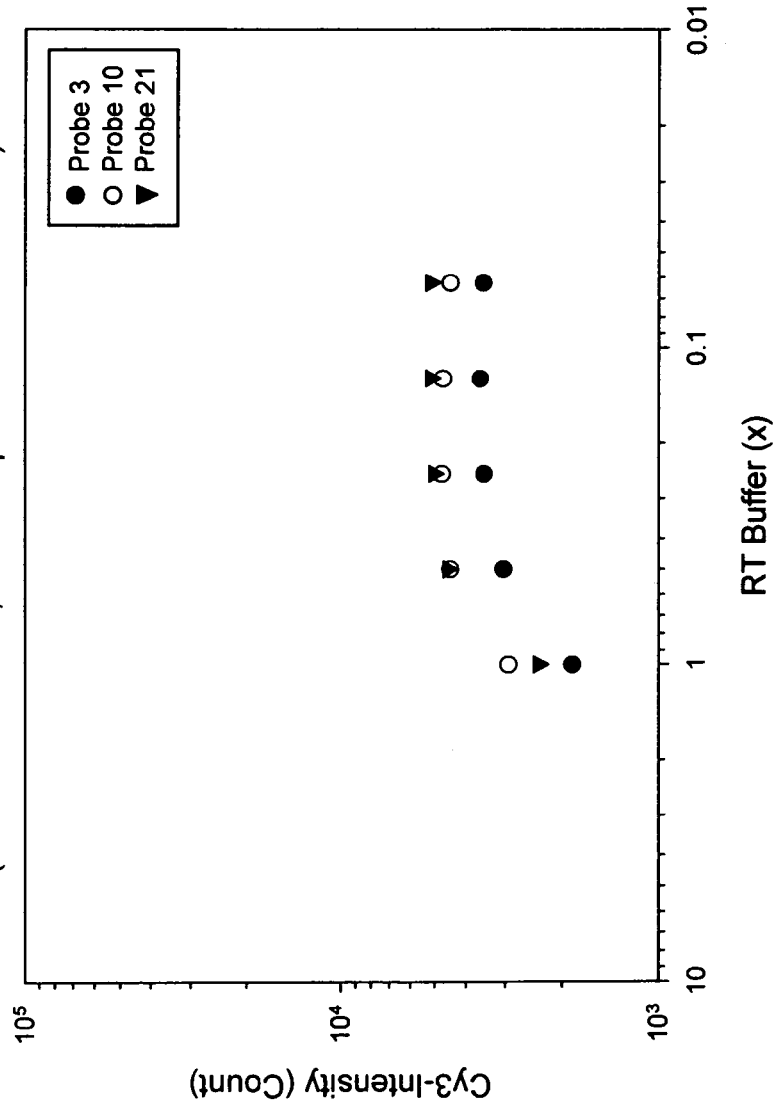
FIG. 27 shows results from a one step IVT-RT-eMAP assay with 3 probes, demonstrating one reaction mix, and an isothermal assay, using m-MLV reverse transcriptase.

Optimization—Various factors may affect the efficiency of in vitro transcription, RNA capture, and/or on-bead reverse transcriptase-catalyzed elongation. Enzyme concentration is one such factor. FIG. 27 shows the titration of M-MLV reverse transcriptase concentration for a particular dsDNA concentration in an on-chip IVT-RT-eMAP reaction. At the highest M-MLV concentration (10 u/μl), the coupled format of the assay generated similar results to the uncoupled format, where SuperSCript III (M-MLV mutant) was used, and the reactions were carried out at two different temperatures.

Figure 28:
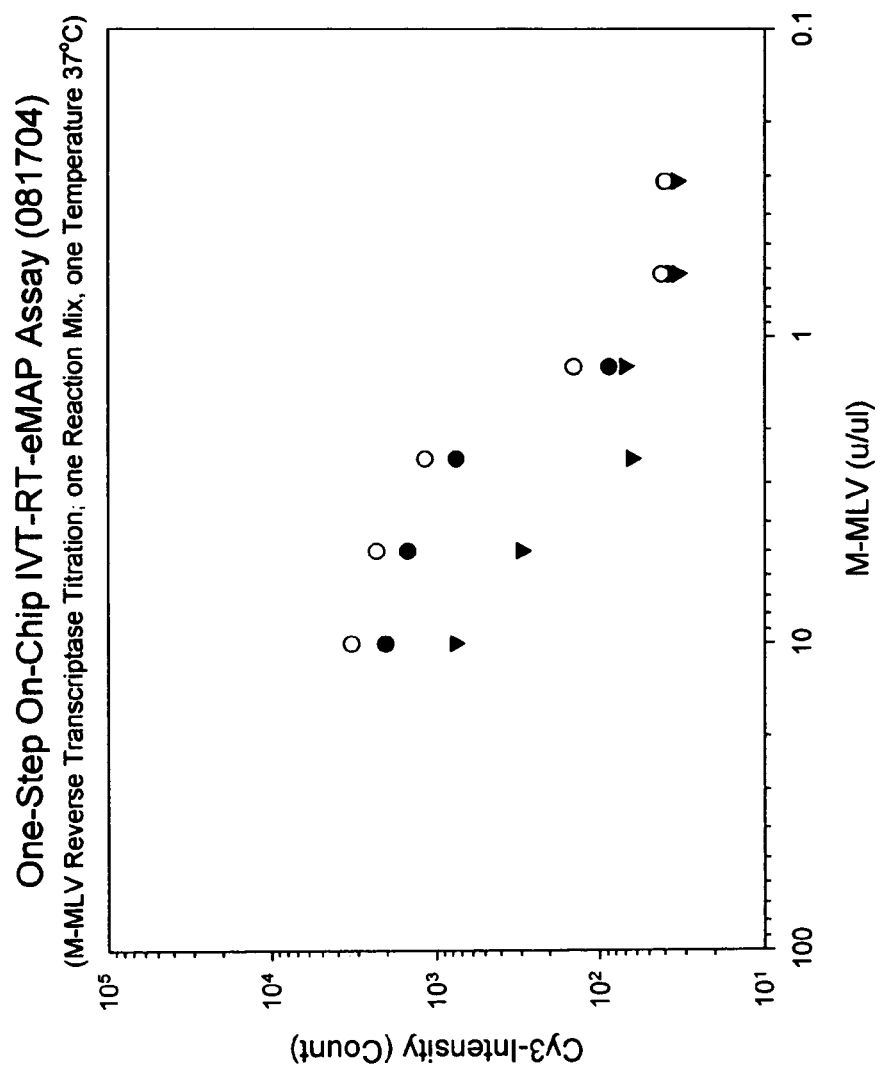
FIG. 28 shows results from a one step IVT-RT-eMAP assay with an inhibitor, and one reaction mix, in an isothermal reaction.

Buffer composition also must be optimized. Thus, in the process of optimizing conditions for the homogeneous reaction, it was determined that RT has an inhibitory effect on transcription, and the RT buffer was titrated to determine its optimal composition in the reaction mixture (FIG. 28).

Figure 21:
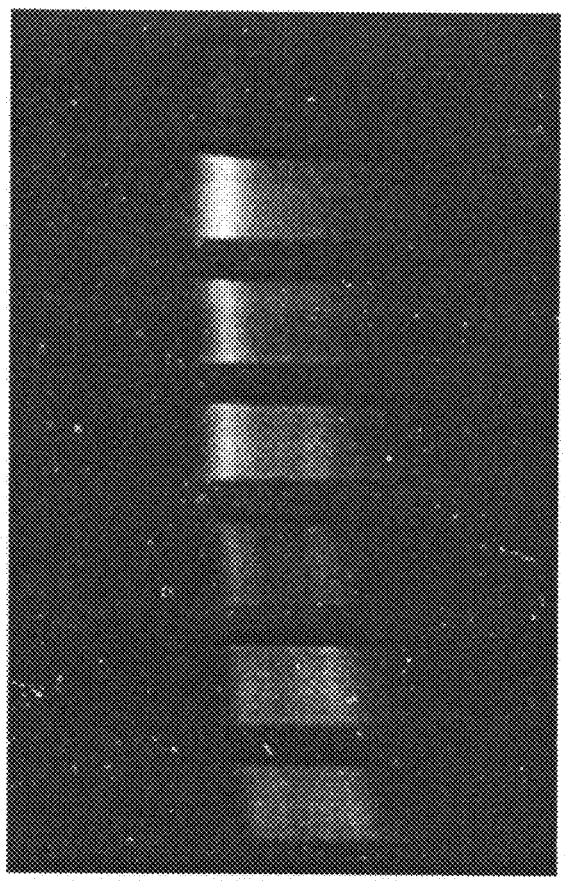
FIG. 21 is the gel from the reaction depicted in FIG. 41.

Further, the coupling efficiency in the homogeneous format of the IVT-RT-eMAP reaction generally will depend on competitive annealing of RNA produced in the IVT reaction to either the bead-displayed RT primer or forward primer in solution. To optimize it, the concentration of forward primer was varied in the presence of M-MLV reverse transcriptase, using dsDNA (97.5 ng/μl), diluted 1:32. RNA gel electrophoresis following DNA digestion indicated that the amount of RNA synthesized increased with the concentration of forward primer (FIG. 21). However, the higher the forward primer concentration, the lower the Cy3 signal produced by elongation of bead-displayed RT primers (although, under present conditions, this reduction in signal was limited to a factor of 4; see FIG. 20). Elimination of this negative influence of the forward primer can further improve the efficiency of on-bead elongation. By balancing the molar ratio of nested primer to forward primer, reducing the amount forward primer, or by increasing the number of reaction cycles, the yield of the reaction can be maximized.

EXAMPLE II:

Real-Time Detection in Homogeneous Format

In one of the assay formats described herein, the cDNA produced in the RT-eMAP reaction can be detected in real-time using fluorescently labeled "looped probes" (see, e.g., U.S. Provisional Application No. 60/628,464 "Probe Density Considerations and Elongation of Complementary Looped Probes Where Probes Are Attached to a Solid Phase" filed Nov. 16, 2004) or molecular beacons, containing a fluorescence donor at or near one terminus and a fluorescence acceptor at or near the other terminus. Looped probes or beacons are particularly preferable for real-time detection of RT-eMAP product in a homogeneous assay format comprising four steps as follows (see FIGS. 31 & 32):

Step 1: Sequence-Specific Capture.

Messenger RNA (mRNA) or cRNA is captured by annealing to a complementary oligonucleotide probe which has a complementary sequence and is attached to a color-encoded bead. The capture step can be carried out with oligonucleotide probes displayed on beads, including beads on the surface of custom BeadChips, on beads which are in suspension in a test tube or beads which are set in a nanoreactor.

Step 2: Synthesis of Complementary DNA (cDNA)

In the presence of RT reaction components, such as dNTPs, a reverse transcriptase will catalyze elongation of the oligonucleotide probes, using the captured RNAs as a template.

Step 3: RNA Cleavage

The RNA template in the RNA-cDNA heteroduplex (formed as a result of RT-eMAP complex) can be degraded by RNaseH. Certain reverse transcriptases, such as M-MLV reverse transcriptase, may contain RNaseH activity, as is known (see G. F. Gerard. J Virol. 1978 April: 26(1): 16-28). Multiple RNase H activities also are associated with mammalian type C retrovirus lysates. Otherwise, the reaction mixture may include RNaseH.

Step 4: Real-Time Labeling of Bead-Displayed cDNA Using Looped Probes

A looped probe or molecular beacon, with a predefined sequence and designed to adopt a "closed" state in solution which remains dark, can anneal to the single-stranded cDNA elongation product on the bead, adopting an "open" state which emits fluorescence. Tag-specific Looped Probes (or Beacons)—The detection of cDNA fragments amplified from a gene family, can be done using a looped probe or beacon directed to a tag that is introduced into a select subset of gene sequences, during reverse transcription of RNA or DNA. The reverse primer is designed to contain at least two portions of sequences, namely, at the 3' terminus, an oligonucleotide sequence that is specific for a gene family of interest and, at the 5' terminus, a T7 promoter sequence. Given an RNA template, reverse transcription and 2nd strand DNA synthesis using a forward primer present in the reaction are performed to generate T7-tagged double-stranded DNA. Given a DNA template, a PCR reaction can be performed using a forward primer to generate double-stranded DNA. In either case, the resulting T7-tagged double-stranded DNA products will contain a gene family-specific sequence tag at the 3' region and a T7 promoter sequence at the 3' end, while the 5' region of the double-stranded DNAs contain sequences corresponding to individual members of the gene family of interest. For example, for a gene family of N different members, there will be N different species of T7-tagged double-stranded DNA products from the reactions.

Alternatively, a sequence tag that is shared by several RNA sequences can be introduced by using an RT primer in which such a tag sequence is inserted between the sequence-specific priming sequence and the T7 promoter sequence at Ambion, Inc.'s website). The number of looped probes of different sequence required for detection is then determined by the number of different tag sequences. Since cDNA fragments are displayed on encoded beads, different looped probe sequences can share the same fluorescence signatures, yet still be decoded following detection However, in certain embodiments, it may be desirable to distinguish different cDNA sequences displayed on beads of the same color but having different tag sequences, by using looped probes of distinguishable fluorescence signatures.

The (complement of the) sequence tag which is incorporated into the elongation product can then be targeted for real-time detection of any of the RNA sequences of interest, using the same looped probe. Briefly, different types of the amplified cRNAs will be captured to probes on the beads, which are specific for individual members of the gene family. Elongation reaction on the beads results in synthesis of cDNA fragments. Each of the cDNA fragments contains the common sequence tag that is originally from reverse primer. A fluorescently-labeled molecular beacon with predefined sequences can bind to the common sequence tag, resulting in generation of fluorescent signal in the homogeneity assay (see FIG. 31).

Figure 4:
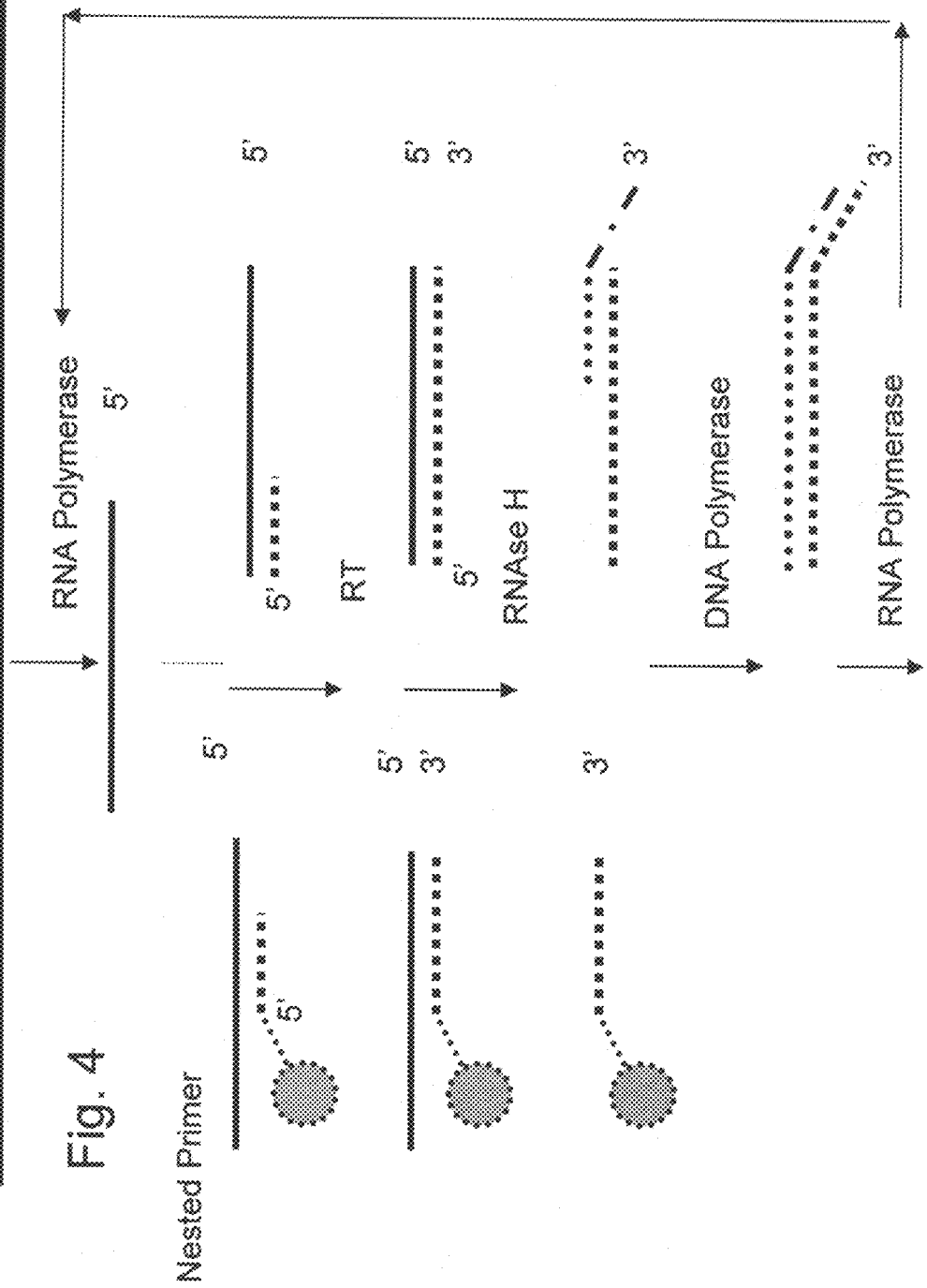
FIG. 4 depicts coupling of exponential amplification of RNA with the IVT method with detection by on-bead capture and elongation with a nested primer.
Figure 5:
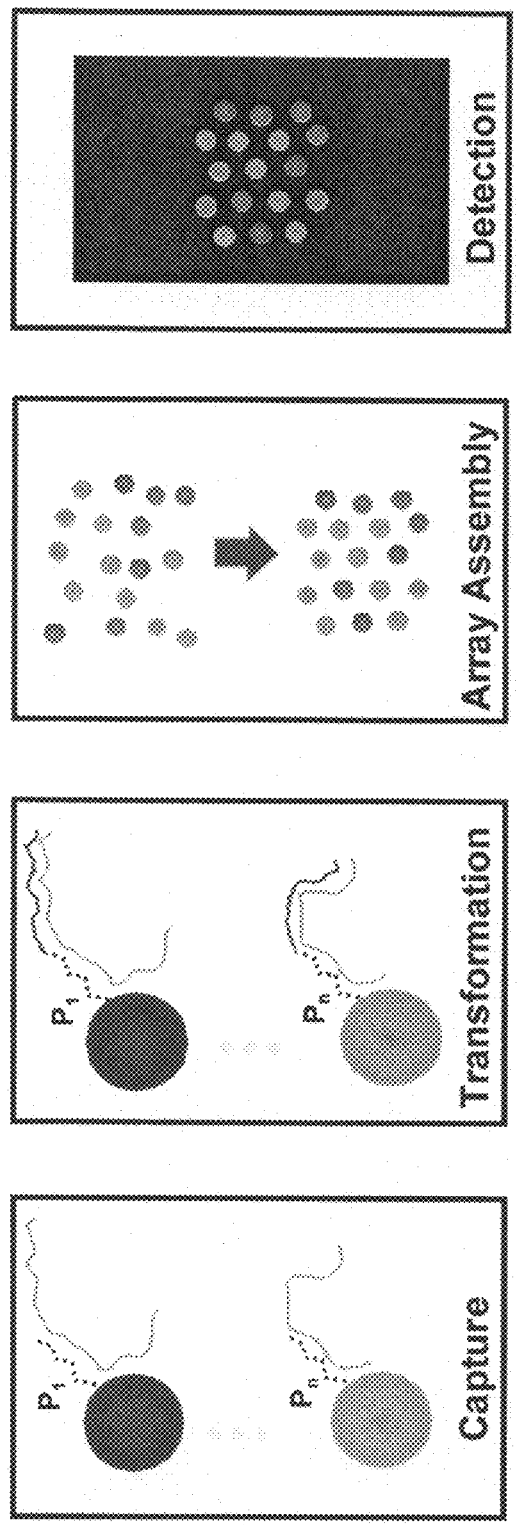
FIG. 5 shows detection of a variety of oligonucleotides and array assembly using encoded beads displaying probes.

FIG. 4 illustrates the use of "nested" primers which align with selected subsequences within the interior of the template. Nested, allele-specific primers allow discrimination among closely similar templates, based on a determination of which of the primers are elongated (see eMAP application). Nested primers directed to designated polymorphic sites within the RNA template permit discrimination of specific products of an IVT reaction, and provide accurate genotyping.

EXAMPLE III

In-Well Homogeneous Beadchip Assay Using Looped Probes

Figure 36:
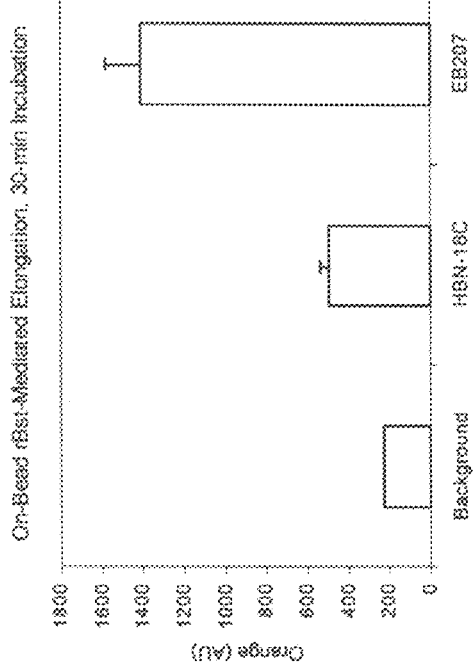
FIG. 36: Green (decoding)-Orange (assay) fluorescence signal intensities for two types of beads used to perform the eMAP reaction in nanoliter volume.

BeadChips were prepared to contain a random planar array of ~4,000 microparticles ("beads") per BeadChip, wherein the beads are color-encoded with 36 distinguishable colors (as illustrated in the exemplary bead map of FIGS. 36 and 37)on a 375-µm thick silicon substrate ("silicon chip"). Bead staining and BeadChip assembly are disclosed U.S. application Ser. No. 10/348,165 (incorporated by reference). Each bead-type is functionalized with oligonucleotide probes of a particular sequence, which are attached to the bead surface prior to assembly of the BeadChips.

Magnetizable chips were constructed by sandwiching a small magnetizable strip (preferably formed from a permalloy material such as NiFe) between two regular chips such that the arrays on both sides face outward, and can contact the reaction buffer.

This experiment was designed to run a homogeneous IVT-RT-eMAP assay in one well of a microtiter plate, in a single-tube format. Purified DQ C2-011 PCR product (a dsDNA) was used as a template. It contained a T7 promoter sequence at the 5' end. Reverse transcription (RT), in vitro transcription (IVT), and elongation (eMAP) reactions were carried out concurrently in the well. Initially, T7-tagged dsDNA templates were 1:2 serially diluted in 8 tubes with ddH$_2$O, starting with 3 ng/µl in the first tube. Then, 2-µl aliquots of the DNA templates from each tube were mixed with a 38 µl IVT-RT-eMAP reaction mix. The composition of the reaction mix is conventional and known; for example it which may contain 0.1 M DTT, RNase inhibitor, Moloney Murine Leukemia Virus (M-MLV) reverse transcriptase, 10 µM dNTP (without dCTP) and 10 µM Cy3-dCTP, and RNase-free H$_2$O.

The procedure for the assay was as follows:
1. Place the magnetizable chip in the well and pipette transfer 40 µl of the IVT-RT reaction mixture into the well.

2. Transfer 10 µl mineral oil (molecular biology grade, purchase from, Sigma Chemical Company) into the well.
3. Attract and suspend the chip to the side of the well by activating the electromagnet located at the side of the well. The chip ends up in an upright position, on one of its edges, such that the array is in contact with the reaction mix.
4. Incubate the reaction mix with the chip at 37° C. for 30 minutes.
5. Deactivate the magnetic field and activate the magnetic field at the bottom of the well, to capture the chip faces the bottom of the well.
6. Interrogate optically using an inverted fluorescence microscope.

FIG. 35 shows the assay procedure and the decoding bead map from this homogeneous assay.

EXAMPLE IV

Performing Reactions in Sub-Microliter Volume

To perform a homogenous reaction with bead suspensions in an isolated reaction volume of 1-10 nl, the following elements were provided: 1) a nano-liter reactor (FIGS. 38A and 38B) in the form of a recess in a silicon substrate, designed to be hydrophobic on the surface and less hydrophobic in the recess; 2) a process of charging and sealing the nanoreactor; and 3) sealing the nanoreactor without disturbing the reaction composition and without introducing optical artefacts.

Fabrication—To "micro-machine" a nano-liter recess, 20 ml of an etching solution was freshly prepared in a flat-bottom glass flask, by adding 10-ml of 45% wt KOH (Aldrich Chemical) to 10-ml of DI water and warming to 70° C. A silicon die (40×40 mm in size), coated with a 50 A° layer of $Si_3N_4$ on n-type 1~10 Ω·cm (100) silicon, was patterned in the center (300×300 µm in area) by removal of the $Si_3N_4$. The die was immersed in the etching solution, using a Teflon stir bar to keep the liquid mildly agitated to disperse $H_2$ bubbles. This process attacks silicon preferentially in the <100> plane, producing a "nano-reactor" with sidewalls of exposed planes 54.7° from the flat bottom. The etch rate at 70° C. is about 0.97 µm/min. The reaction time can be adjusted in order to achieve a desired depth. For instance, a 20-min reaction produced a 19-µm deep recess (1.6 nL in volume), and a 50-min reaction produced a 48-µm deep (3.5-nL) recess. After etching, the die was rinsed in DI water and blow-dried in a stream of dry $N_2$. Chlorinated polydimethylsiloxane (Aquaphobe™, Gelest) was used to react with hydroxy and silanol groups formed on the nitride by exposure to air during storage, to form a chemically bound polydimethylsiloxane surface. The coating was applied as a 1% solution in toluene. The die was immersed in the solution for 10 minutes, dried in air, and then cured at 110° C. for 20 minutes in an exhaust oven. Even though bare silicon in the recess is hydrophobic in nature, native oxide growth renders it less hydrophobic than the top surface. Repeated contact with aqueous solution helps reduce hydrophobicity as well.

The material of choice for sealing is a 200-µm-thick polydimethylsiloxane (PDMS) layer that is transparent, hydrophobic, and stable at 100° C. SYLGARD 184 silicone elastomer base and curing agent from Dow Corning was thoroughly mixed, in a ratio of 10 parts base to 1 part curing agent, by weight. The mixture was de-gassed in a vacuum of <25 inches of mercury for 30 minutes. Pre-cleaned glass slides (25×75×1 mm) (Fisher) were cleaned with acetone and wiped with Tween 20 (2%) to facilitate release. The prepolymer mixture was poured between two glass slides spaced 200-µm apart by use of Kapton spacers. The film was cured at room temperature for 24 hours and cut into a 20×20 mm square die.

Charging and Sealing the Nanoreactor—A reaction mixture was prepared, and its density adjusted to match the density of the beads suspended in it, so that during the assembly of nanoliter volume and subsequent reactions, beads remained suspended. To prepare the reaction mixture, in a 100% humidity chamber, a 2.5-µl pipette was used to pick 0.2-µl of the reaction mixture and to form a bead suspension at the tip. The liquid was placed on top of the nano-Reactor, and covered with a 200-µm-thick PDMS film prepared as described above. Gentle pressure was applied to make contact between the film and the reactor surface. Immediately, the corner of a thin 1-ply wipe (Kimberly Clark) was used to establish a continuous outflow of reaction mixture towards the edge. Since both the sealing layer and the treated reactor surface have very low surface energies, excess fluid was thereby siphoned off. Van der Waals attraction brought the sealing layer in conformal contact with the silicon surface to form a tight seal over the nano-Reactor. The decrease in separation between the two surfaces and the formation of the seal was confirmed by observation of interference fringe patterns. Because the assembly and subsequent reactions were taking place under humidity control (i.e., ~100%), the removal of aqueous content did not affect the composition of the mixture and there was no detectable deformation of PDMS sealing layer in the recess region. Optical artifacts were thereby avoided.

Performing eMAP in Nanoliter Volume—Two oligonucleotide probes, EB207 and N18, were coupled in accordance with standard methods to two types of beads, encoded with different levels of a green dye and respectively referred to as Green 3 (or G3) and Green 5 (or G5). Beads, at 1% solid content, were stored in PBST buffer. The sequence of probe EB207 is designed to be complementary to the 5' region of a 45-nucleotide synthetic DNA target (known as "T3938") while probe N18 contains a random sequence of 18 nucleotides. The encoding green fluorescence levels were G3<G5, so that following the reaction, the expected assay fluorescence (Cy 3) levels in the orange channel would be in a reverse order: $O_{EB207} > O_{N18}$.

A reaction mixture of 20 µl total volume was prepared on ice block shortly before use, containing 15 µl of 20 nM T3938 target diluted in ddH$_2$O, 2 µl of 10× Bst reaction buffer (0.2 M Tris-HCl @ Ph 8.5 at 25° C. and 50 mM MgCl$_2$) 1 µl of rBst DNA polymerase (Epicentre, San Diego. Calif.) at a concentration of 5 U/µl (stored in 50% glycerol solution containing 50 mM Tris-HCl (Ph7.5), 0.1 M NaCl. 0.1 mM EDTA, 1 mM dithiothreitol and 0.1% Triton X-100) 0.2 µl of 10 µM dNTPs without dCTP, 0.2 µl of 10 µM TAMRA-dCTP. In a separate tube, 2 µl of bead suspension from each of the tubes containing EB207-modified G3 beads, and N18-modified G5 beads, were pooled, pelleted, and re-suspended in 4 µl of the prepared reaction mixture.

Figure 37:
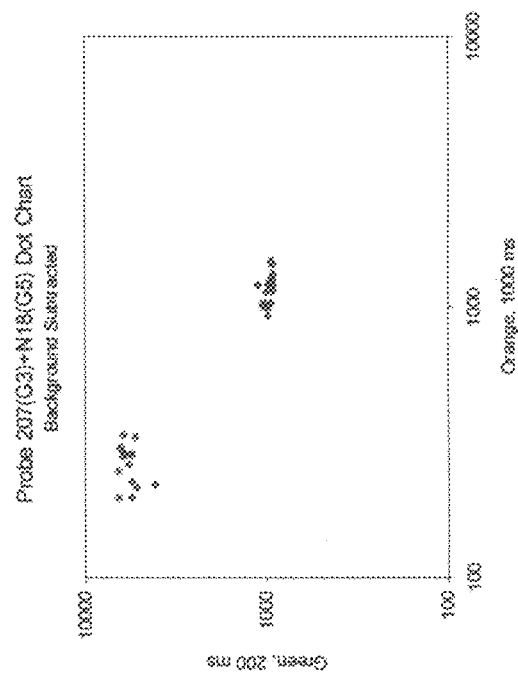
FIG. 37—Assay signal intensities recorded following an elongation performed in nanoliter volume.

A nanoreactor (1~2 nL in volume), fabricated as described above, was charged with bead suspension as described above. Chips containing the charged nanoreactor were incubated for 30 minutes in a heater (Boeke) at 65° C., the optimal temperature for rBst activity, with relative humidity controlled at 100%. Following incubation, the chip containing the nanoreactor was examined using a fluorescence microscope (Nikon Eclipse E800). Orange fluorescence emitted from TAMRA-dCTP incorporated by rBst-mediated elongation was recorded using a filter cube (Ha: Cy3. Chroma Technology) and an exposure time of 1000 ms. Green fluorescence, emitted from the encoded beads, was recorded using a filter cube (Ra: FITC; Chroma Technology) and an exposure time of 200 ms. All images were recorded using a cooled 16-bit CCD camera (Apogee Instruments Inc.). FIG. 37 shows the resulting map of green-orange fluorescence. The G3 beads displaying probe EB207 are identifiable by their lower average green encoding intensity: they display a higher average orange assay signal intensity, indicating incorporation of TAMRA-dCTP into the product in the course of the probe elongation mediated by rBst polymerase, following target capture. The net background count of 230 suggests that un-incorporated TAMRA-dCTP conjugates remained in solution. The ratio of (background-corrected) signal intensities produced by EB207 to that produced by N18 is about 5. A separate experiment (not shown here) suggested that prolonged incubation would further increase the specific signal and thus the discrimination ratio.

EXAMPLE V

DNA Polymerase-Mediated Extension in Micro- and Nano-Liter Volume

BeadChips were prepared containing a random array composed of ~4,000 color-encoded microparticles ("beads") of 50 different types, on a 375-µm thick <100> n-type silicon substrate. Color-coding was achieved by staining the beads in accordance with a solvent tuning method described in U.S. application Ser. No. 10/348,165 (incorporated by reference). Stained beads were functionalized by covalent attachment of amine-modified single-stranded DNA probes. Each probe, displayed on one type of bead, contained a ~20-nt capture sequence specific to a single-stranded target such that the base at the 3'-end is aligned with the SNP (Single Nucleotide Polymorphism) of interest. A total of 48 probes were incorporated to form a panel of HEA (Human Erythrocyte Antibody) typing. Following multiplexed PCR reaction, and Exo-Sap purification and digestion, a 10.5-µl reaction mix was obtained that contained the 6.5-µl original PCR product of all the amplicons, 2-µl of 1:10 diluted ExoSAP, and 2-µl of a λ-exonuclease mix containing λ-exonuclease enzyme at 1:1 in exonuclease buffer. Then, a mixture of 10-µl elongation mix (4-µl 1× Buffer, 2-ρl DNTP (-dCTP) @ 1 µM, 2-µl dCTP-Cy3 @ 0.2µM, 2-µl 0.32 U Thermo Sequenase in Thermo Sequenase Buffer) and 0.0125-µM beta-Actin @ 1 µM was added to make final volume of mix about 20 µl.

The mold for fabricating a nanoliter-scale recess was made in n-type 1~10 Ω·cm (100) silicon substrate by patterning with photolithography and dry etching. A 60-µm thick star-shaped post (~0.5 mm²) was generated in each die (1.75×1.75 mm² in area). A mixture of 10:1 PDMS (polydimethylsiloxane) prepolymer and curing agent (Dow-Corning Sylgard 184) was stirred thoroughly and then degassed under vacuum. Four 300-µm thick spacers were placed on the flat region of the silicon wafer piece and a clean glass slip was placed on top of the spacers. A small volume of prepolymer mixture was then transferred by pipette to contact one edge of the gap. The mixture then filled the gap by capillary force. The moderately high viscosity and large wetting angle ensured that all the air was displaced. Curing was in 70° C. for 2 hours. The replica was peeled off from the Silicon and the glass slip and sliced into 1.75×1.75 mm² dies.

On a glass slide hosting 8 HEA-panel BeadChips, chips Nos. 1~4 were used to test nL-scale reaction and Nos. 5~8 were used to test sub-µL-scale reaction. In a 100% relative humidity chamber, on each chip No. 1 to 4, a 1-µl reaction mix was picked and about 0.25 µl was dropped on the chip with about 0.75 µl on the PDMS recess. When pipetting, the liquid was stirred slightly with the pipette tip to remove air bubbles, if any, from the chip or the recess. Shortly after liquid transfer, the PDMS die was flipped and placed onto the chip. With the merged liquid in one volume, the bead array was aligned with the recess. Immediately, a corner of a thin 1-ply wiper (Kimberly Clark) was used to remove the reaction mixture from the edge. By doing so, PDMS surface can contact the chip surface and form a complete seal. A cross section of the arrangement is shown in FIG. 38A. For each chip No. 5 to 8, 0.5 µl of reaction mix containing PCR amplicons was transferred to the chip surface; the reaction volume was closed by fixing the coverslip via two PDMS pads placed onto the 500-µm spacers, and transferring 8-µl of mineral oil into the gap; capillary forces ensure that the oil quickly encircles and seals the reaction volume. FIG. 38B shows a cross section of the arrangement.

The slide was incubated in a heater (Boekel) at 53° C. for 18 minutes, with relative humidity controlled at 100%. At the end of incubation, all PDMS seals were removed from chip # 1~4. On chip # 5~8, mineral oil was first removed by wiper paper. Then, the cover slips were removed. Using vacuum, reaction mix was removed from all chip surfaces, and each chip was washed three times with 25 µl DDI $H_2O$. Finally, the slide was blown dry with pure dry nitrogen.

The slide was then examined by using a fluorescence microscope (Nikon Eclipse E800). Fluorescence (orange) emitted from the TAMRA-dCTP incorporated by Thermosequenase enzyme-mediated elongation and was determined by exposing (1500 ms) through orange filter cube (HQ: Cy3, Chroma Technology). In a proprietary software program, the orange image was processed to extract average intensities on all beads. Since each bead was previously identified by their characteristic combination of green and blue fluorescence levels using blue filter cube (HYDROX) and green filter cube (HQ: FITC/Bodipy/Fluo3 / Di O), the bar chart can be plotted to assign a Cy3 fluorescence level with its coefficient of variance to each probe. FIGS. 39 and 40 show bar charts of the response from all the probes (full HEA panel) on chip # 1~4 and chip # 5~8, respectively. The small chip-to-chip variation suggests the similarity and effectiveness of reactions under two seemingly different conditions, that is, a 30-nL volume in 60-µm gap on chip # 1~4 and a 0.5-µL volume in 125-µm gap on chip # 5~8. The liquid layer in reaction was stagnant and relative humidity was under control. Since the stringency is high (~2.5-mM salt in a temperature above corresponding $T_m$), the reaction was not limited by diffusion and participating reaction volume could be <<10 nL.

EXAMPLE VI

Figure 41:
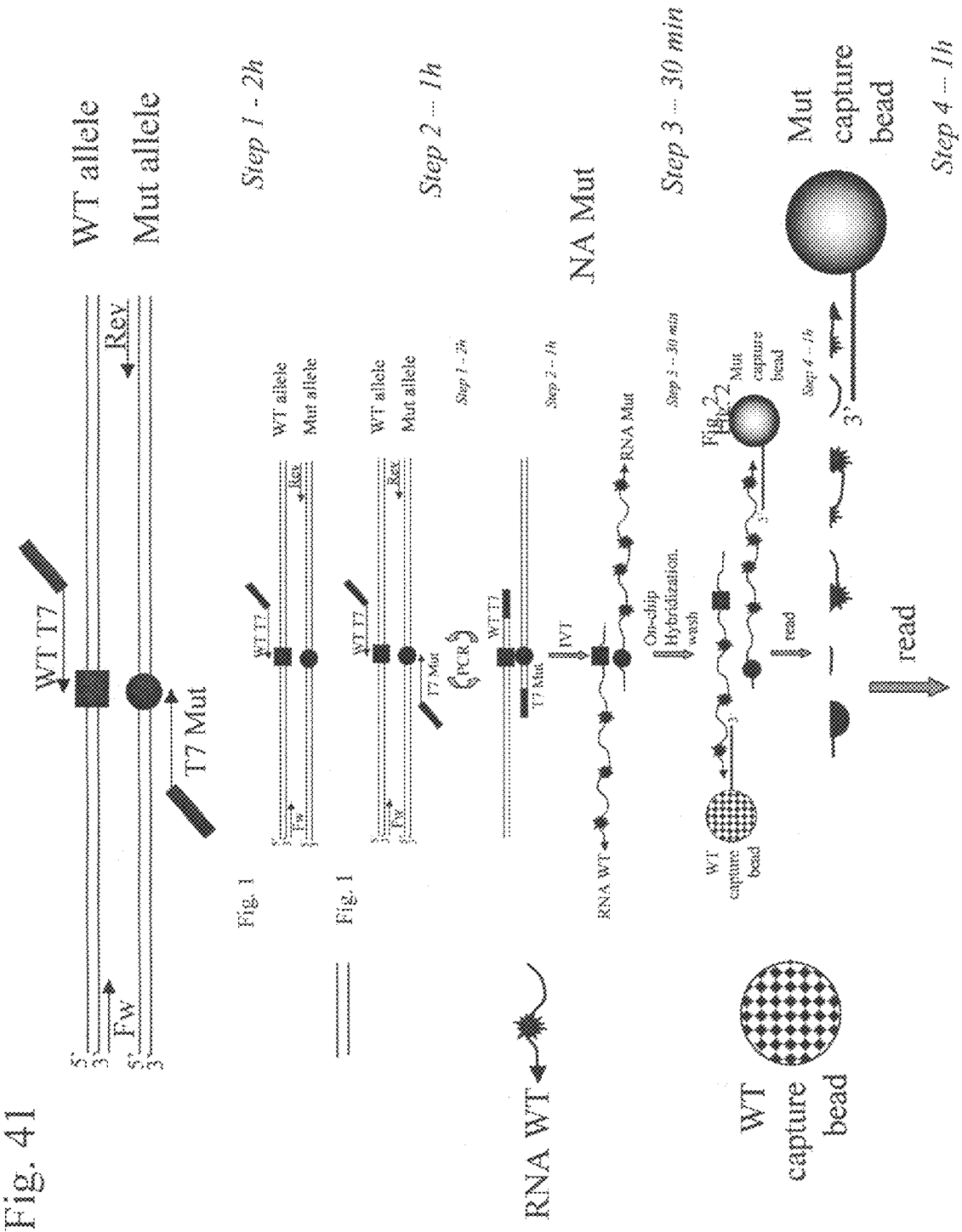
FIG. 41 depicts the steps in detecting SNPs using PCR and an IVT RT-eMAP reaction.

Strand Selection by IVT Combined with Detection of Polymorphisms by Allele-Specific PCR This example illustrates the combination of PCR-mediated target amplification and strand selection via IVT for the purpose of allele detection using a rapid and convenient 4-step protocol (FIG. 41).

DNA Extraction—Genomic DNA was purified using Qiagen purification kit (cat# 951436) from clinical samples and analyzed as follows:

Step 1—First 10 cycles of PCR reaction were perform to amplify the GATA amplicon (FIG. 2) as follows: 25 ul of PCR mixture contained 2.5 ul of 10× PCR buffer (all reagents supplied by Qiagen, cat# 203203), 3 ul of 25 mM $MgCl_2$, 1 ul of 10 mM dNTPs mix, 1 ul of 10 uM primer Fw, 1 ul of 10 uM primer Rev, 8 ul of gDNA, 1 ul of Taq HotStar DNA polymerase 5 u/ul, 2.5 ul of sterile distilled $H_2O$. Another 25 cycles were performed after addition of 1 ul of 10 uM T7/ WT primer and 1 ul of 10 uM T7/Mut primer to PCR mixture.

The following temperature profile was implemented in GeneAmp PCR System 9700 (Applied Biosystems) thermocycler:

Denaturation: 15 min 94°
35 cycles of
  Denaturation: 30 sec 94°, ramp rate 60%
  Annealing: 30 sec 60°, ramp rate 50%
  Elongation: 50 sec 72°, ramp rate 35%
Hold: 8 min 72°
Hold: 4° for ever Step 2—The PCR reaction aliquot of 1 ul was directly used in 10 ul of IVT reaction mix (MEGAshortscrip™ T7 kit, Ambion, cat# 1354, or MEGAscrip™ T7 kit, cat# 1334) using Cy3UTP:UTP ratio as 1:10. The IVT reaction lasted for 1 h at 37°

Step 3—The whole volume of 10 ul IVT reaction was mixed with 10 ul of 2×TMAC and used for on-chip hybridization, which was performed for 15° at 50° in 1× TMAC followed by 3 subsequent wash steps with 1× TMAC buffer.

Step 4—Image Acquisition and Analysis

This protocol allows simultaneously to detect presence of 1 sets of homozygous wild type, mutant, and heterozygous alleles from HEA panel, as well as from other panels in multiplex format.

While the current protocol utilizes Taq DNA polymerase, the application of other high-fidelity and high specificity polymerases also is possible, and may be preferable to ensure high fidelity in allele detection at the 3'-end of the primer. Available choices include:

Accuprime (or Platinum) Pfx DNA polymerase (Invitrogen, #11708-013 or #12344-024);
PfuUltra High Fidelity DNA polymerase(Stratagene, # 600390); or
Phusion High-Fidelity DNA polymerase (New England Biolabs, #F-530S).

It should be understood that the terms, expressions and examples used herein are exemplary only, and not limiting, and that the scope of the invention is defined only in the claims which follow, and includes all equivalents of the subject matter of the claims. Process and method steps in the claims can be carried out in any order, including the order set forth in the claims, unless otherwise specified in the claims.

What is claimed is:

1. A method of performing multiplexed nucleic acid analysis using a in-vitro transcription amplification and reverse transcription detection reaction of double stranded target nucleic acid molecules in a reaction chamber, comprising:
   (a) adding the double stranded target nucleic acid molecules and all reagents required to complete in-vitro transcription amplification and reverse transcription detection reaction to the reaction chamber, wherein said reaction chamber is not more than 500 nl in volume and includes encoded microparticles arranged in a substantially planar array, wherein differently-encoded microparticles have different DNA oligonucleotides attached thereto, and said encoded microparticles not being positioned such that particular particle types are in particular locations in the array; and
   (b) incubating the reaction chamber at a constant temperature for a period of time, whereby, said target double-stranded nucleic acid molecules are converted to antisense RNA via an in-vitro transcription reaction in the reaction chamber and said antisense RNA are captured by said DNA oligonucleotides displayed on said encoded microparticles, and wherein the different oligonucleotides are elongated by more than one nucleotide using labeled dNTPs, rNTPs or ddNTPs via a reverse transcription reaction to generate labeled cDNA, when antisense RNA strands which include RNA subsequences complementary to oligonucleotide subsequences in the different oligonucleotides, are present and anneal to the oligonucleotide subsequences; and
   wherein the reaction volume is confined through the use of oil or another water immiscible liquid such that the reaction volume is small enough such that amplification of the initial double stranded target by a factor of $10^3$ generates sufficient antisense RNA concentration such that it can be detected in step (b) above.

2. The method of claim 1 wherein an RNA polymerase is included in the chamber for the IVT reaction.

3. The method of claim 1 further including decoding the encoded microparticles to identify the labeled cDNA strands.

4. The method of claim 1 wherein the double stranded target nucleic acid molecules include a T7 promoter.

5. The method of claim 1 further including MMLV Reverse Transcriptase or SuperScript III Reverse Transcriptase for use in generating the labeled cDNA strand.

6. The method of claim 1 wherein all reagents are present in the chamber at the start of the amplifying step, for the IVT reaction.

7. The method of claim 1 wherein the encoded microparticles are color-encoded.

8. The method of claim 1 wherein detection is by imaging of fluorescence emitted by the labeled dNTPs, or ddNTPs incorporated in the cDNA.

9. The method of claim 1 wherein the cDNAs are labeled by annealing with labeled nucleic acids.

10. The method of claim 9 wherein said labeled nucleic acids are designed to form a non-fluorescent configuration when in solution and a fluorescent configuration when annealed to the cDNA.

11. The method of claim 9 wherein said labeled nucleic acids are designed to form a fluorescent configuration when in solution and a non-fluorescent configuration when annealed to the labeled cDNA.

12. The method of claim 1 wherein labeled cDNA is only generated if nucleotides at or near the 3' end of an oligonucleotide attached to encoded microparticles is complementary to nucleotides in the RNA strand which are in an aligned position with said nucleotides at or near the 3' end.

13. The method of claim 1 wherein the encoded microparticles are pre-assembled in a random planar array configuration on a substrate and transcription, capture and elongation reactions occur on the substrate.

14. The method of claim 1 wherein the encoded microparticles are suspended and assembled into a planar configuration.

15. The method of claim 10 or 11 wherein the labeled nucleic acid has subsequences which can anneal with each other, and whereupon annealing with the cDNA, the signal emitted from the labeled nucleic acid changes to either non-fluorescent or fluorescent, as applicable.

16. The method of claim 1 wherein the total reaction time for the IVT reaction is 1000 seconds or less.

17. The method of claim 1 wherein the steps in the in-vitro transcription amplification and reverse transcription detection reaction are carried out without modifying the temperature in the reaction chamber.

* * * * *